United States Patent
Grant, III et al.

(10) Patent No.: US 7,179,805 B2
(45) Date of Patent: Feb. 20, 2007

(54) 7-AMINO ALKYLIDENYL-HETEROCYCLIC QUINOLONES AND NAPHTHYRIDONES

(75) Inventors: Eugene B. Grant, III, Flemington, NJ (US); Mark J. Macielag, Branchburg, NJ (US); Xiaoqing Xu, Plainsboro, NJ (US); Steven David Paget, Hillsborough, NJ (US); Michele Ann Weidner-Wells, Hillsborough, NJ (US)

(73) Assignee: Janssen Pharmaceutica N.V., Beerse (BE)

(*) Notice: Subject to any disclaimer, the term of this patent is extended or adjusted under 35 U.S.C. 154(b) by 293 days.

(21) Appl. No.: 10/937,238

(22) Filed: Sep. 9, 2004

(65) Prior Publication Data
US 2005/0101588 A1 May 12, 2005

Related U.S. Application Data

(60) Provisional application No. 60/504,924, filed on Sep. 22, 2003.

(51) Int. Cl.
| | |
|---|---|
| A61K 31/4353 | (2006.01) |
| A61K 31/5383 | (2006.01) |
| C07D 215/14 | (2006.01) |
| C07D 471/14 | (2006.01) |
| C07D 498/04 | (2006.01) |

(52) U.S. Cl. .............. 514/230.2; 514/300; 514/312; 544/101; 546/123; 546/158

(58) Field of Classification Search ............. None
See application file for complete search history.

(56) References Cited

U.S. PATENT DOCUMENTS 5,478,841 A 12/1995 Perrin 6,329,391 B1 12/2001 Ledoussal et al.

FOREIGN PATENT DOCUMENTS

| EP | 0 241 206 A2 | 10/1987 |
|---|---|---|
| EP | 0 362 759 A1 | 4/1990 |
| WO | WO 02/085886 A2 | 10/2002 |

OTHER PUBLICATIONS

Hokuriku Seiyaku Co., Ltd., "7-Aminopyrrolidinylquinoline-3-Carboxylic Acid", Patents Abstract of Japan, vol. 018, No. 668, Dec. 16, 1994.
PCT International Search Report, dated Feb. 15, 2005, for PCt Int'l. Appln. No. PCT/US2004/029523.

*Primary Examiner*—Cecilia Tsang
*Assistant Examiner*—Lexington A. Hoffman

(57) ABSTRACT

The present invention relates to compounds having a structure according to Formula I

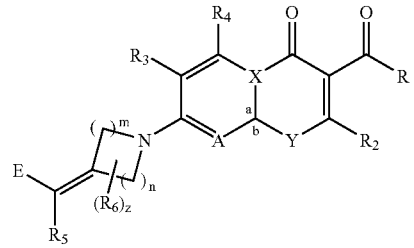

Formula I wherein n, m, z, R, $R_2$, $R_3$, $R_4$, $R_5$, $R_6$, A, E, X, Y, a and b are as defined above;
or an optical isomer, diastereomer or enantiomer thereof; a pharmaceutically acceptable salt, hydrate, or prodrug thereof.

14 Claims, No Drawings

7-AMINO ALKYLIDENYL-HETEROCYCLIC QUINOLONES AND NAPHTHYRIDONES

CROSS-REFERENCE TO RELATED APPLICATION

This application claims the benefit under 35 U.S.C. § 119(e) of provisional application Ser. No. 60/504,924, filed on Sep. 22, 2003, which is incorporated herein in its entirety.

FIELD OF INVENTION

The subject invention relates to novel antimicrobial compounds, their compositions and their uses.

BACKGROUND

The chemical and medical literature describes compounds that are said to be antimicrobial, i.e., capable of destroying or suppressing the growth or reproduction of microorganisms, such as bacteria. For example, such antibacterial agents are described in Antibiotics, Chemotherapeutics, and Antibacterial Agents for Disease Control (M. Greyson, editor, 1982), E. Gale et al., The Molecular Basis of Antibiotic Action 2d edition (1981), Recent Research Developments in Antimicrobial Agents & Chemotherapy (S. G. Pandalai, Editor, 2001), Quinolone Antimicrobial Agents (John S Wolfson., David C Hooper, Editors, 1989), and F. O'Grady, H. P. Lambert, R. G. Finch, D. Greenwood, Martin Dedicoat, "Antibiotic and Chemotherapy, 7th edn." (1997).

The mechanisms of action of these antibacterial agents vary. However, they are generally believed to function in one or more ways: by inhibiting cell wall synthesis or repair; by altering cell wall permeability; by inhibiting protein synthesis; or by inhibiting the synthesis of nucleic acids. For example, beta-lactam antibacterial agents act through inhibiting essential penicillin binding proteins (PBPs) in bacteria, which are responsible for cell wall synthesis. As another example, quinolones act, at least in part by inhibiting synthesis of DNA, thus preventing the cell from replicating.

The pharmacological characteristics of antimicrobial agents, and their suitability for any given clinical use, vary. For example, the classes of antimicrobial agents (and members within a class) may vary in 1) their relative efficacy against different types of microorganisms, 2) their susceptibility to development of microbial resistance and 3) their pharmacological characteristics such as their bioavailability and biodistribution. Accordingly, selection of an appropriate antimicrobial agent in a given clinical situation requires analysis of many factors, including the type of organism involved, the desired method of administration, the location of the infection to be treated and other considerations.

However, many such attempts to produce improved antimicrobial agents yield equivocal results. Indeed, few antimicrobial agents are produced that are truly clinically acceptable in terms of their spectrum of antimicrobial activity, avoidance of microbial resistance, and pharmacology. Thus there is a continuing need for broad-spectrum antimicrobial agents, which are effective against resistant microbes.

Some 1,4-dihydroquinolone, naphthyridine or related heterocyclic moieties are known in the art to have antimicrobial activity and are described in the following references: R. Albrecht Prog. Drug Research, Vol. 21, p. 9 (1977); J. Wolfson et al., "The Fluoroquinolones: Structures, Mechanisms of Action and Resistance, and Spectra of Activity In Vitro", Antimicrob. Agents and Chemother., Vol. 28, p. 581 (1985); G. Klopman et al. Antimicrob. Agents and Chemother., Vol. 31, p. 1831 (1987); M. P. Wentland et al., Ann. Rep. Med. Chem., Vol. 20, p. 145 (1986); J. B. Cornett et al., Ann. Rep. Med. Chem., Vol. 21, p. 139 (1986); P. B. Fernandes et al. Ann. Rep. Med. Chem., Vol. 22, p. 117 (1987); A. Koga, et al. "Structure-Activity Relationships of Antibacterial 6,7- and 7,8-Disubstituted 1-alkyl-1,4-dihydro-4-oxoquinoline-3-carboxylic Acids" J. Med. Chem. Vol. 23, pp. 1358–1363 (1980); J. M. Domagala et al., J. Med. Chem. Vol. 31, p. 991 (1988); T. Rosen et al., J. Med. Chem. Vol. 31, p. 1598 (1988); B. Ledoussal et al., "Non 6-Fluoro Substituted Quinolone Antibacterials: Structure and Activity", J. Med. Chem. Vol. 35, p. 198–200 (1992); U.S. Pat. No. 6,329,391; A. M Emmerson et al., "The quinolones: Decades of development and use", J. Antimicrob. Chemother., Vol 51, pp 13–20 (2003); J. Ruiz, "Mechanisms of resistance to quinolones: target alterations, decreased accumulation and DNA gyrase protection" J. Antimicrob. Chemother. Vol. 51, pp 1109–1117 (2003); Y. Kuramoto et al., "A Novel Antibacterial 8-Chloroquinolone with a Distorted Orientation of the N1-(5-Amino-2,4-difluorophenyl) Group" J. Med. Chem. Vol. 46, pp 1905–1917 (2003); Japanese Patent Publication 06263754; European Patent Publication 487030; International Patent Publication WO0248138; International Patent Publication WO9914214; U.S. Patent Publication 2002/0049192; International Patent Publication WO02085886; European Patent Publication 572259; International Patent Publication WO0136408; U.S. Pat. No. 5,677,456; European Patent Publication 362759; U.S. Pat. No. 5,688,791; U.S. Pat. No. 4,894,458; European Patent Publication 677522; U.S. Pat. No. 4,822,801; U.S. Pat. No. 5,256,662; U.S. Pat. No. 5,017,581; European Patent Publication 304087; International Patent Publication WO0136408; International Patent Publication WO02085886; Japanese Patent Publication 01090184; International Patent Publication WO9209579; International Patent Publication WO0185728; European Patent Publication 343524; Japanese Patent Publication 10130241; European Patent Publication 413455; International Patent Publication WO0209758; International Patent Publication WO0350107; International Patent Publication WO9415933; International Patent Publication WO9222550; Japanese Patent Publication 07300472; International Patent Publication WO0314108; International Patent Publication WO0071541; International Patent Publication WO0031062; and U.S. Pat. No. 5,869,670.

WO03050107 describes a series of dihydroquinolone, naphthyridine and related heterocyclic antibacterial agents. Of particular interest is the disclosure of compounds of the formula,

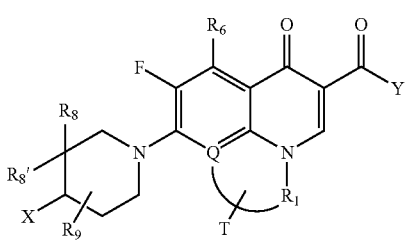

wherein $R_8$ and $R_{8'}$ are hydrogen, alkyl, substituted alkyl, alkylamino, or aralkyl, $R_9$ is hydrogen, alkyl, alkylamino, dialkylamino, aryl, aralkyl, or trihaloalkyl, and X is hydroxy, alkoxy, acyloxy, amino or substituted amino.

European Patent Publication 362759 discloses 1,4-dihydroquinolone and naphthyridine antibacterial agents of the formula,

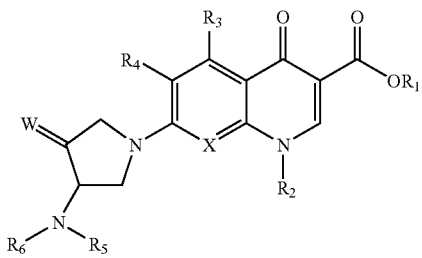

wherein W is C1–3 alkylidene and $R_5$ and $R_6$ are hydrogen or alkyl.

International Patent Publication WO 99/14214 and U.S. Pat. No. 6,329,391 disclose quinolone antibacterial agents with $C_7$-piperdinyl, $C_7$-azetidinyl, or $C_7$-pyrrolidinyl substituents of the formula,

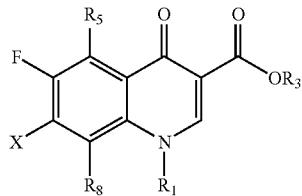

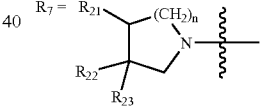

Of particular interest are those compounds wherein $R_7$ is amino, aminoalkyl, or substituted aminoalkyl and $R_9$ is selected from hydrogen, $C_1$–$C_4$ alkanyl, $C_2$–$C_6$ alkenyl, $C_2$–$C_6$ alkynyl, or a $C_3$–$C_6$ fused or spirocyclic alkyl ring. For compounds with a substituted piperidine at the 7-position of the quinolonecarboxylic acid, among the preferred subtituents are 3-amino-4-methyl, 3-amino-4,4-dimethyl, 3-amino-4-spirocyclopropyl, 3-amino-6-cyclopropyl, 3-aminomethyl, 4-aminomethyl and 3-methylamino. For compounds with a substituted pyrrolidine at the 7-position of the quinolonecarboxylic acid nucleus, preferred substituents include 3-(1-aminoethyl), 3-aminomethyl, 4-(1-aminoethyl)-2,2-dimethyl, and 2-aminomethyl. For compounds with an azetidine substituent at the 7-position of the quinolonecarboxylic acid, the compounds having the substituents, 3-amino, 3-aminomethyl and 3-(1-amino-1-methyl) ethyl, are included among the preferred examples.

European Patent Publication 241206A2 discloses compounds of the formula,

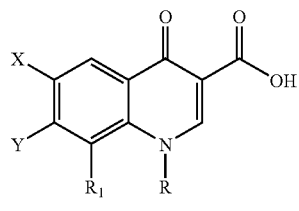

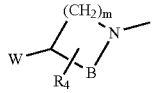

wherein B is —$CH_2$—, —$(CH_2)_2$—, or —$(CH_2)_3$—, $R_4$ is hydrogen, $C_1$–$C_3$ alkyl, hydroxy, or $C_1$–$C_3$ alkoxy, W is hydroxy, $C_1$–$C_3$ alkoxy, or a group of the formula $R_5R_6N$—$(CH_2)_n$— in which n is 0 or 1 and $R_5$ and $R_6$ are the same or different and each represents a hydrogen atom, a $C_1$–$C_3$ alkyl group or an aralkyl group, and m is 1 or 2. each symbol is as defined in the specification of the above mention publication. For the piperidine substituent at the 7-position of the quinolonecarboxylic acid, the compounds having substituents of 4-amino-3-methyl, 4-methylamino-3-methyl, 4-hydroxy-3methyl are included in the preferred examples therein.

European Patent Publication 0394553B1 discloses antiviral compounds of the formula,

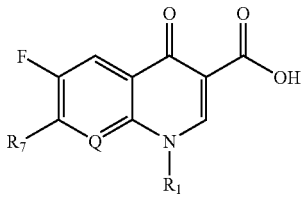

wherein $R_{21}$, $R_{22}$ and $R_{23}$ are each independently is a hydrogen atom, a halogen atom, amino, $C_1$–$C_6$ alkyl, $C_1$–$C_8$ alkoxy, or amino $C_1$–$C_8$ alkyl and two of them may be combined with each other to form a Spiro ring, and n is 1 or 2.

European Patent Publication 0572259A1 discloses antiviral compounds of the formula,

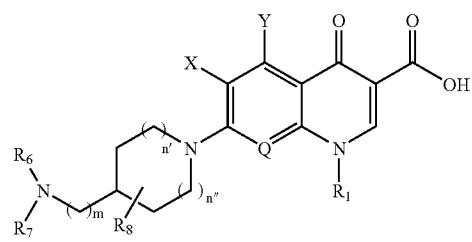

wherein $R_6$ and $R_7$ may be the same or different and each represents a hydrogen atom or a lower alkyl group, m is 0 or 1, n' is 1 or 2, n" is 1, 2, 3 or 4, and R8 is a hydrogen atom, a lower alkyl group, a hydroxy group or a lower alkoxy group.

International Patent Publication WO9324479 discloses compounds of the formula,

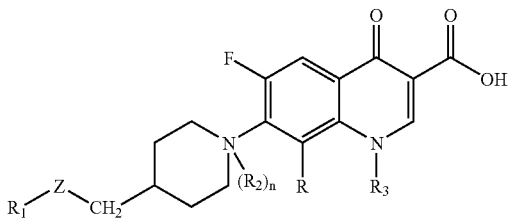

wherein Z is an amino radical, $R_1$ is hydrogen, an (optionally hydroxylated lower alkyl) radical, an acyl radical derived from a carboxylic acid, an alkyl carbonic acid or an arylsulfonic acid or an arylamino carbonyl radical, $R_2$ is an oxygen atom, and n is 0 or 1.

Examples of bacterial infections resistant to antibiotic therapy have been reported in the past; they are now a significant threat to public health in the developed world. The development of microbial resistance (perhaps as a result of the intense use of antibacterial agents over extended periods of time) is of increasing concern in medical science. "Resistance" can be defined as existence of organisms, within a population of a given microbial species, that are less susceptible to the action of a given antimicrobial agent. This resistance is of particular concern in environments such as hospitals and nursing homes, where relatively high rates of infection and intense use of antibacterial agents are common. See, e.g., W. Sanders, Jr. et al., "Inducible Beta-lactamases: Clinical and Epidemiologic Implications for the Use of Newer Cephalosporins", *Review of Infectious Diseases*, p. 830 (1988).

Pathogenic bacteria are known to acquire resistance via several distinct mechanisms including inactivation of the antibiotic by bacterial enzymes (e.g., β-lactamases hydrolyzing penicillin and cephalosporins); removal of the antibiotic using efflux pumps; modification of the target of the antibiotic via mutation and genetic recombination (e.g., penicillin-resistance in *Neiserria gonorrhoeae*); and acquisition of a readily transferable gene from an external source to create a resistant target (e.g., methicillin-resistance in *Staphylococcus aureus*). There are certain Gram-positive pathogens, such as vancomycin-resistant *Enterococcus faecium*, which are resistant to virtually all commercially available antibiotics.

Hence existing antibacterial agents have limited capacity in overcoming the threat of resistance. Thus it would be advantageous to provide new antibacterial agents that can be used against resistant microbes.

SUMMARY OF INVENTION

Applicants have found a novel series of quinolones and related compounds that are effective against resistant microbes, and provide significant activity advantages over the art. In particular, the invention relates to compounds having a structure according to Formula (I)

Formula I

[Structure of Formula I]

wherein:
n is an integer from 1 to 3;
m is an integer from 1 to 3;
z is an integer from 0 to 3;
R is selected from hydrogen, hydroxy, and alkoxy;
$R_2$ is hydrogen;
$R_3$ and $R_4$ are independently selected from hydrogen, halogen, amino, hydroxy, alkoxy, alkylthio, alkyl, alkenyl and alkynyl;
$R_5$ is selected from hydrogen, halogen, alkyl, aryl, alkoxy, and alkylthio;
$R_6$ is independently selected from alkyl, hydroxy, alkoxy, alkylthio, alkenyl, alkynyl, aryl, alkoxyimino, and halogen; or $R_5$ and $R_6$ join to form a 4- to 7-membered carbocyclic ring wherein each carbon atom of the ring can be optionally substituted with $R_{12}$, wherein $R_{12}$ is selected from the group consisting of halogen, amino, hydroxy, alkoxy, alkylthio, alkyl, alkenyl, alkynyl, oxo, alkoxyimino and hydroxyimino;
E is selected from the group consisting of:

1) 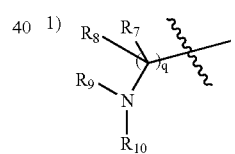

wherein
q is an integer from 1 to 3;
$R_7$ and $R_8$ are each independently selected from hydrogen and alkyl, or $R_7$ and $R_8$ join to form a 3- to 6-membered carbocyclic ring, or either of $R_7$ or $R_8$ can be joined independently to either of $R_9$ or $R_{10}$ to form a heterocyclic ring containing the nitrogen atom to which $R_9$ or $R_{10}$ are bonded, wherein
$R_9$ and $R_{10}$ are each independently selected from hydrogen, alkyl, acyl, alkoxycarbonyl, or sulfonyl, or alternatively $R_9$ and $R_{10}$ join to form a heterocyclic ring containing the nitrogen atom to which they are bonded;

2) 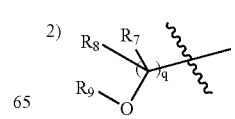

wherein, q is as defined above;

$R_7$ and $R_8$ are each independently selected from hydrogen and alkyl, or $R_7$ and $R_8$ join to form a 3- to 6-membered carbocyclic ring, and $R_9$ is selected from hydrogen, alkyl, acyl, alkoxycarbonyl, or sulfonyl; and 3) alkenyl;

A is selected from N and $C(R_{11})$, wherein $R_{11}$ is selected from hydrogen, alkyl, halogen, hydroxy, alkoxy, alkylthio, and cyano;

X is selected from C and N, where if X is C, a is a double bond and b is a single bond, and if X is N, a is a single bond and b is a double bond; and Y is selected from $N(R_1)$ and $C(R_1)$, with the proviso that when Y is $N(R_1)$, X is C and when Y is $C(R_1)$, X is N, wherein $R_1$ is selected from C3 to C6 cycloalkyl, C4 to C6 heterocycloalkyl, alkyl, alkene, a 6-membered aryl and a 6-membered heteroaryl; provided that if A is $C(R_{11})$, X is C and Y is $N(R_1)$, then $R_{11}$ and $R_1$ can join to form a 6-membered heterocyclic ring, or if A is $C(R_{11})$, X is C and Y is $N(R_1)$, then $R_2$ and $R_1$ can join to form a monocyclic or bicyclic heterocyclic ring, or if A is $C(R_{11})$, X is C and Y is $N(R_1)$, then $R_2$ and R can join to form a 5-membered heterocyclic ring;

or an optical isomer, diastereomer or enantiomer thereof; a pharmaceutically acceptable salt, hydrate, or prodrug thereof.

In addition, methods of using compounds of the invention as starting materials are also contemplated in this invention.

It has been found that the compounds of this invention, and compositions containing these compounds, are effective antimicrobial agents against a broad range of pathogenic microorganisms with advantages of activity against resistant microbes.

Accordingly, the present invention is also directed to a method of treating a subject having a condition caused by or contributed to by bacterial infection, which comprises administering to said mammal a therapeutically effective amount of the compound of Formula 1.

The present invention is further directed to a method of preventing a subject from suffering from a condition caused by or contributed to by bacterial infection, which comprises administering to the subject a prophylactically effective dose of the pharmaceutical composition of a compound of Formula 1.

DETAILED DESCRIPTION

The subject invention provides compounds of Formula (I)

Formula I

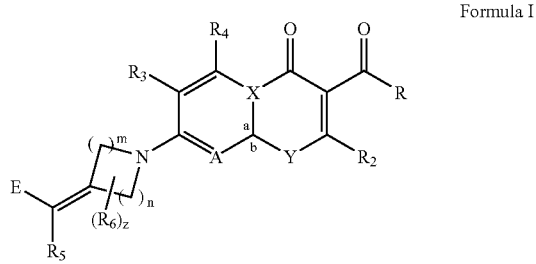

wherein:

a, b, n, m, z, R, $R_2$, $R_3$, $R_4$, $R_5$, $R_6$, A, E, X and Y are as defined in the Summary of the Invention section above.

Relative to the above description, certain definitions apply as follows.

Unless otherwise noted, under standard nomenclature used throughout this disclosure the terminal portion of the designated side chain is described first, followed by the adjacent functionality toward the point of attachment.

Unless specified otherwise, the terms "alkyl", "alkenyl", and "alkynyl," whether used alone or as part of a substituent group, include straight and branched chains having 1 to 8 carbon atoms, or any number within this range. The term "alkyl" refers to straight or branched chain hydrocarbons. "Alkenyl" refers to a straight or branched chain hydrocarbon with at least one carbon-carbon double bond. "Alkynyl" refers to a straight or branched chain hydrocarbon with at least one carbon-carbon triple bound. For example, alkyl radicals include methyl, ethyl, n-propyl, isopropyl, n-butyl, isobutyl, sec-butyl, t-butyl, n-pentyl, 3-(2-methyl)butyl, 2-pentyl, 2-methylbutyl, neopentyl, n-hexyl, 2-hexyl and 2-methylpentyl. "Alkoxy" radicals are oxygen ethers formed from the previously described straight or branched chain alkyl groups. "Cycloalkyl" groups contain 3 to 8 ring carbons and preferably 5 to 7 ring carbons. The alkyl, alkenyl, alkynyl, cycloalkyl group and alkoxy groups may be independently substituted with one or more members of the group including, but not limited to, hydroxyimino, halogen, alkyl, alkenyl, alkynyl, cycloalkyl, alkoxy, oxo, alkoxyimino aryl, heteroaryl, heterocyclo, CN, nitro, —$OCOR_{13}$, —$OR_{13}$, —$SR_{13}$, —$SOR_{13}$, —$SO_2R_{13}$, —$COOR_{13}$, —$NR_{13}R_{14}$, —$CONR_{13}R_{14}$, —$OCONR_{13}R_{14}$, —$NHCOR_{13}$, —$NHCOOR_{13}$, and —$NHCONR_{13}R_{14}$, wherein $R_{13}$ and $R_{14}$ are independently selected from hydrogen, alkyl, alkenyl, alkynyl, cycloalkyl, aryl, heteroaryl, heterocyclo, aralkyl, heteroaralkyl, and heterocycloalkyl, or alternatively $R_{14}$ and $R_{15}$ may join to form a heterocyclic ring containing the nitrogen atom to which they are attached.

The term "acyl" as used herein, whether used alone or as part of a substituent group, means an organic radical having 2 to 6 carbon atoms (branched or straight chain) derived from an organic acid by removal of the hydroxyl group. The term "Ac" as used herein, whether used alone or as part of a substituent group, means acetyl.

The term "halo" or "halogen" means fluoro, chloro, bromo or iodo. (Mono-, di-, tri-, and per-)halo-alkyl is an alkyl radical substituted by independent replacement of the hydrogen atoms thereon with halogen.

"Aryl" or "Ar," whether used alone or as part of a substituent group, is a carbocyclic aromatic radical including, but not limited to, phenyl, 1- or 2-naphthyl and the like. The carbocyclic aromatic radical may be substituted by independent replacement of 1 to 3 of the hydrogen atoms thereon with aryl, heteroaryl, halogen, OH, CN, mercapto, nitro, amino, $C_1$–$C_8$-alkyl, $C_2$–$C_8$-alkenyl, $C_1$–$C_8$-alkoxyl, $C_1$–$C_8$-alkylthio, $C_1$–$C_8$-alkyl-amino, di ($C_1$–$C_8$-alkyl) amino, (mono-, di-, tri-, and per-)halo-alkyl, formyl, carboxy, alkoxycarbonyl, $C_1$–$C_8$-alkyl-CO—O—, $C_1$–$C_8$-alkyl-CO—NH—, or carboxamide. Illustrative aryl radicals include, for example, phenyl, naphthyl, biphenyl, fluorophenyl, difluorophenyl, benzyl, benzoyloxyphenyl, carboethoxyphenyl, acetylphenyl, ethoxyphenyl, phenoxyphenyl, hydroxyphenyl, carboxyphenyl, trifluoromethylphenyl, methoxyethylphenyl, acetamidophenyl, tolyl, xylyl, dimethylcarbamylphenyl and the like. "Ph" or "PH" denotes phenyl. "Bz" denotes benzoyl.

Whether used alone or as part of a substituent group, "heteroaryl" refers to a cyclic, fully unsaturated radical having from five to ten ring atoms of which one ring atom is selected from S, O, and N; 0–2 ring atoms are additional heteroatoms independently selected from S, O, and N; and the remaining ring atoms are carbon. The radical may be joined to the rest of the molecule via any of the ring atoms. Exemplary heteroaryl groups include, for example, pyridinyl, pyrazinyl, pyrimidinyl, pyridazinyl, pyrrolyl, pyrazolyl, imidazolyl, thiazolyl, oxazolyl, isoxazolyl, thiadiazolyl, triazolyl, triazinyl, oxadiazolyl, thienyl, furanyl, quinolinyl, isoquinolinyl, indolyl, isothiazolyl, N-oxo-pyridyl, 1,1-dioxothienyl, benzothiazolyl, benzoxazolyl, benzothienyl, quinolinyl-N-oxide, benzimidazolyl, benzopyranyl, benzisothiazolyl, benzisoxazolyl, benzodiazinyl, benzofurazanyl, indazolyl, indolizinyl, benzofuryl, cinnolinyl, quinoxalinyl, pyrrolopyridinyl, furopyridinyl (such as furo[2,3-c]pyridinyl, furo[3,2-b]pyridinyl, or furo[2,3-b]pyridinyl), imidazopyridinyl (such as imidazo[4,5-b]pyridinyl or imidazo[4,5-c]pyridinyl), naphthyridinyl, phthalazinyl, purinyl, pyridopyridyl, quinazolinyl, thienofuryl, thienopyridyl, and thienothienyl. The heteroaryl group may be substituted by independent replacement of 1 to 3 of the hydrogen atoms thereon with aryl, heteroaryl, halogen, OH, CN, mercapto, nitro, amino, $C_1$–$C_8$-alkyl, $C_1$–$C_8$-alkoxyl, $C_1$–$C_8$-alkylthio, $C_1$–$C_8$-alkyl-amino, di($C_1$–$C_8$-alkyl)amino, (mono-, di-, tri-, and per-)halo-alkyl, formyl, carboxy, alkoxycarbonyl, $C_1$–$C_8$-alkyl-CO—O—, $C_1$–$C_8$-alkyl-CO—NH—, or carboxamide.

Heteroaryl may be substituted with a mono-oxo to give for example a 4-oxo-1H-quinoline.

The terms "heterocycle," "heterocyclic," and "heterocyclo" refer to an optionally substituted, fully saturated, partially saturated, or non-aromatic cyclic group which is, for example, a 4- to 7-membered monocyclic, 7- to 11-membered bicyclic, or 10- to 15-membered tricyclic ring system, which has at least one heteroatom in at least one carbon atom containing ring. Each ring of the heterocyclic group containing a heteroatom may have 1, 2, or 3 heteroatoms selected from nitrogen atoms, oxygen atoms, and sulfur atoms, where the nitrogen and sulfur heteroatoms may also optionally be oxidized. The nitrogen atoms may optionally be quaternized. The heterocyclic group may be attached at any heteroatom or carbon atom. The heterocyclic group may be substituted by independent replacement of 1 to 3 of the hydrogen atoms thereon with aryl, heteroaryl, halogen, OH, CN, mercapto, nitro, amino, $C_1$–$C_8$-alkyl, $C_1$–$C_8$-alkoxyl, $C_1$–$C_8$-alkylthio, $C_1$–$C_8$-alkyl-amino, di($C_1$–$C_8$-alkyl)amino, (mono-, di-, tri-, and per-)halo-alkyl, formyl, carboxy, alkoxycarbonyl, $C_1$–$C_8$-alkyl-CO—O—, $C_1$–$C_8$-alkyl-CO—NH—, or carboxamide.

Exemplary monocyclic heterocyclic groups include pyrrolidinyl; oxetanyl; pyrazolinyl; imidazolinyl; imidazolidinyl; oxazolinyl; oxazolidinyl; isoxazolinyl; thiazolidinyl; isothiazolidinyl; tetrahydrofuryl; piperidinyl; piperazinyl; 2oxopiperazinyl; 2-oxopiperidinyl; 2-oxopyrrolidinyl; 4-piperidonyl; tetrahydropyranyl; tetrahydrothiopyranyl; tetrahydrothiopyranyl sulfone; morpholinyl; thiomorpholinyl; thiomorpholinyl sulfoxide; thiomorpholinyl sulfone; 1,3-dioxolane; dioxanyl; thietanyl; thiiranyl; 2-oxazepinyl; azepinyl; and the like. Exemplary bicyclic heterocyclic groups include quinuclidinyl; tetrahydroisoquinolinyl; dihydroisoindolyl; dihydroquinazolinyl (such as 3,4-dihydro-4-oxo-quinazolinyl); dihydrobenzofuryl; dihydrobenzothienyl; benzothiopyranyl; dihydrobenzothiopyranyl; dihydrobenzothiopyranyl sulfone; benzopyranyl; dihydrobenzopyranyl; indolinyl; chromonyl; coumarinyl; isochromanyl; isoindolinyl; piperonyl; tetrahydroquinolinyl; and the like.

The term "carbocyclic" refers to a saturated or unsaturated, non-aromatic, monocyclic, hydrocarbon ring of 3 to 7 carbon atoms.

Substituted aryl, substituted heteroaryl, and substituted heterocycle may also be substituted with a second substituted aryl, a second substituted heteroaryl, or a second substituted heterocycle to give, for example, a 4-pyrazol-1-yl-phenyl or 4-pyridin-2-yl-phenyl.

Designated numbers of carbon atoms (e.g., $C_1$–$C_8$ or $C_{1-8}$) shall refer independently to the number of carbon atoms in an alkyl or cycloalkyl moiety or to the alkyl portion of a larger substituent in which alkyl appears as its prefix root.

Unless specified otherwise, it is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein.

The term "hydroxy protecting group" refers to groups known in the art for such purpose. Commonly used hydroxy protecting groups are disclosed, for example, in T. H. Greene and P. G. M. Wuts, Protective Groups in Organic Synthesis, 2nd edition, John Wiley & Sons, New York (1991), which is incorporated herein by reference. Illustrative hydroxyl protecting groups include but are not limited to tetrahydropyranyl; benzyl; methylthiomethyl; ethythiomethyl; pivaloyl; phenylsulfonyl; triphenylmethyl; trisubstituted silyl such as trimethylsilyl, triethylsilyl, tributylsilyl, tri-isopropylsilyl, t-butyldimethylsilyl, tri-t-butylsilyl, methyldiphenylsilyl, ethyldiphenylsilyl, t-butyldiphenylsilyl; acyl and aroyl such as acetyl, benzoyl, pivaloylbenzoyl, 4-methoxybenzoyl, 4-nitrobenzoyl and arylacyl.

Where the compounds according to this invention have at least one stereogenic center, they may accordingly exist as enantiomers. Where the compounds possess two or more stereogenic centers, they may additionally exist as diastereomers. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

Some of the compounds of the present invention may have trans and cis isomers. In addition, where the processes for the preparation of the compounds according to the invention give rise to mixture of stereoisomers, these isomers may be separated by conventional techniques such as preparative chromatography. The compounds may be prepared as a single stereoisomer or in racemic form as a mixture of some possible stereoisomers. The non-racemic forms may be obtained by either synthesis or resolution. The compounds may, for example, be resolved into their component enantiomers by standard techniques, such as the formation of diastereomeric pairs by salt formation. The compounds may also be resolved by covalent linkage to a chiral auxiliary, followed by chromatographic separation and/or crystallographic separation, and removal of the chiral auxiliary. Alternatively, the compounds may be resolved using chiral chromatography.

The phrase "a pharmaceutically acceptable salt" denotes one or more salts of the free base or free acid which possess the desired pharmacological activity of the free base or free acid as appropriate and which are neither biologically nor otherwise undesirable. These salts may be derived from inorganic or organic acids. Examples of inorganic acids are hydrochloric acid, nitric acid, hydrobromic acid, sulfuric acid, or phosphoric acid. Examples of organic acids are acetic acid, propionic acid, glycolic acid, lactic acid, pyruvic acid, malonic acid, succinic acid, malic acid, maleic acid, fumaric acid, tartaric acid, citric acid, benzoic acid, cinnamic acid, mandelic acid, methanesulfonic acid, ethanesulfonic acid, p-toluenesulfonic acid, benzenesulfonic acid, salicyclic acid and the like. Suitable salts are furthermore those of inorganic or organic bases, such as KOH, NaOH, Ca(OH)$_2$, Al(OH)$_3$, piperidine, morpholine, ethylamine, triethylamine and the like.

Included within the scope of the invention are the hydrated forms of the compounds that contain various amounts of water, for instance, the hydrate, hemihydrate, and sesquihydrate forms. The present invention also includes within its scope prodrugs of the compounds of this invention. In general, such prodrugs will be functional derivatives of the compounds that are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", ed. H. Bundgaard, Elsevier, 1985.

The term "subject" includes, without limitation, any animal or artificially modified animal. As a particular embodiment, the subject is a human.

The term "drug-resistant" or "drug-resistance" refers to the characteristics of a microbe to survive in the presence of a currently available antimicrobial agent such as an antibiotic at its routine, effective concentration.

TABLE 1

Table 1 contains a non-limiting list of preferred compounds of Formula I.

| Structure | R5 Substituent | Compound Number |
|---|---|---|
| | F | 1 |
| | CH$_3$ | 2 |
| | Cl | 3 |
| | CH$_3$CH$_2$ | 69 |
| | F | 4 |
| | F | 5 |
| | Cl | 65 |

TABLE 1-continued

Table 1 contains a non-limiting list of preferred compounds of Formula I.

| Structure | R5 Substituent | Compound Number |
|---|---|---|
| | F<br>Cl<br>CH₃<br>CH₃CH₂ | 6<br>7<br>70<br>71 |
| | F<br>CH₃ | 8<br>9 |
| | F | 10 |
| | F | 11 |
| | F | 12 |

TABLE 1-continued

Table 1 contains a non-limiting list of preferred compounds of Formula I.

| Structure | R5 Substituent | Compound Number |
|---|---|---|
| | Cl | 13 |
| | Cl | 14 |
| | Cl | 15 |
| | Cl | 72 |
| | Cl | 73 |

TABLE 1-continued

Table 1 contains a non-limiting list of preferred compounds of Formula I.

| Structure | R5 Substituent | Compound Number |
|-----------|----------------|-----------------|
| | Cl | 74 |
| | Cl | 75 |
| | Cl | 76 |
| | Cl | 77 |
| 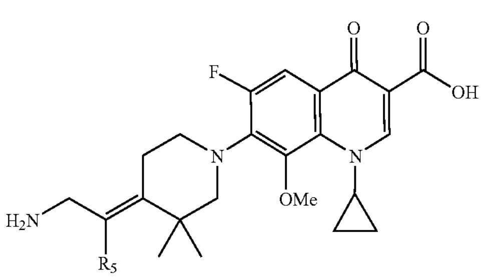 | F | 78 |

TABLE 1-continued

Table 1 contains a non-limiting list of preferred compounds of Formula I.

| Structure | R5 Substituent | Compound Number |
|---|---|---|
| (structure) | F | 79 |
| (structure) | F<br>Cl | 80<br>81 |

General Reaction Scheme for Compound Preparation

In making the compounds of the invention, the order of synthetic steps may be varied to increase the yield of desired product. In addition, the skilled artisan will also recognize the judicious choice of reactions, solvents, and temperatures are an important component in successful synthesis. While the determination of optimal conditions, etc. is routine, it will be understood that a variety of compounds can be generated in a similar fashion, using the guidance of the schemes below.

The starting materials used in preparing the compounds of the invention are known, made by published synthetic methods or available from commercial vendors.

It is recognized that the skilled artisan in the art of organic chemistry can readily carry out standard manipulations of the organic compounds without further direction; that is, it is well within the scope and practice of the skilled artisan to carry out such manipulations. These include, but are not limited to, reductions of carbonyl compounds to their corresponding alcohols, oxidations, acylations, aromatic substitutions, both electrophilic and nucleophilic, etherifications, esterification and saponification and the like. Examples of these manipulations are discussed in standard texts such as March, *Advanced Organic Chemistry* (Wiley), Carey and Sundberg, *Advanced Organic Chemistry* (Vol. 2), Feiser & Feiser, *Reagents for Organic Synthesis* (16 volumes), L. Paquette, *Encyclopedia of Reagents for Organic Synthesis* (8 volumes), Frost & Fleming, *Comprehensive Organic Synthesis* (9 volumes) and the like.

The skilled artisan will readily appreciate that certain reactions are best carried out when other functionality is masked or protected in the molecule, thus avoiding any undesirable side reactions and/or increasing the yield of the reaction. Often the skilled artisan utilizes protecting groups to accomplish such increased yields or to avoid the undesired reactions. Examples of these manipulations can be found for example in T. Greene, *Protecting Groups in Organic Synthesis*.

General procedures for preparing heterocyclic nuclei useful in making the compounds of the invention are described in the following references, all incorporated by reference herein (including articles listed within the references): U.S. Pat. No. 6,329,391, European Patent Publication 342849, International Patent Publication WO9711068, European Patent Publication 195316, European Patent Publication 1031569, U.S. Pat. No. 6,025,370, European Patent Publication 153828, European Patent Publication 191451, European Patent Publication 153163, European Patent Publication 230053, European Patent Publication 976749, International Patent Publication WO0118005, International Patent Publication WO9407873, U.S. Pat. No. 4,777,253, European Patent Publication 421668, International Patent Publication WO0248138, European Patent Publication 230295, International Patent Publication WO9914214, U.S. Patent Publication 20020049223, International Patent Publication WO9921849, International Patent Publication WO9729102, International Patent Publication WO0334980, International Patent Publication WO0209758, International Patent Publication WO9619472, German Patent Publication DE 3142854, International Patent Publication WO0334980, International Patent Publication WO0328665, European Patent Publication 47005, International Patent Publication WO0311450, and European Patent Publication 688772.

The compounds of the subject invention may be prepared in several ways. Versatile methodologies for preparation of the compounds of the invention are shown in Scheme I below, where L is a leaving group such as fluoro or chloro:

Scheme I

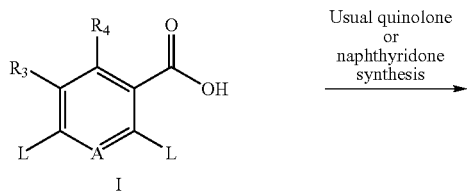

Scheme II

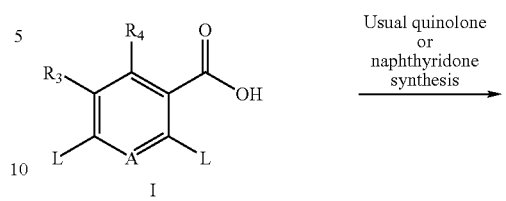

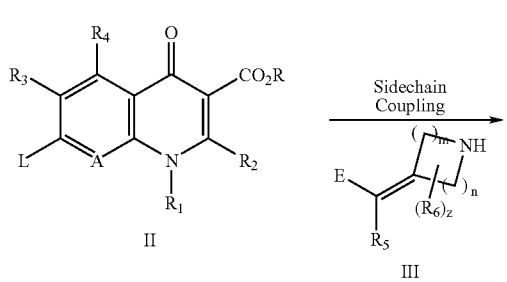

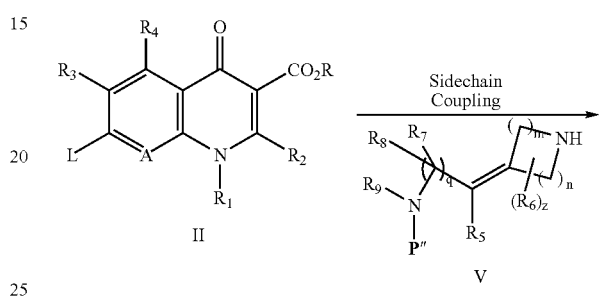

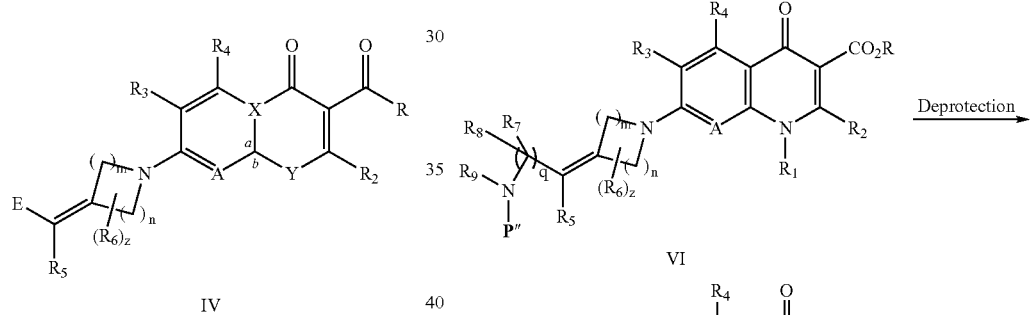

In the case where E is

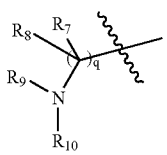

and at least one of $R_9$ and $R_{10}$ is hydrogen, it may be necessary to protect the terminal nitrogen to effect selective conversion to the desired product (Scheme II). In such case, standard amine protecting groups known to those skilled in the art, such as t-butyloxycarbonyl (Boc), benzyloxycarbonyl (Cbz), benzyl (Bn), 9-fluorenylmethoxycarbonyl (Fmoc), allyloxycarbonyl (Alloc), 2-trimethylsilylethoxycarbonyl (Teoc), N-formyl, N-acetyl, N-benzoyl, or phthalimide, may be used to mask the terminal amine, as in compound V. Following sidechain coupling, the protecting group may be removed under standard conditions known to those skilled in the art to obtain the desired product VII. VII may be further elaborated, for example by alkylation, to other compounds of the invention VIII.

P″ = protecting group

Methodologies for providing the compounds of the invention where X is N and Y is $C(R_1)$ are shown in Scheme III below:

Scheme III

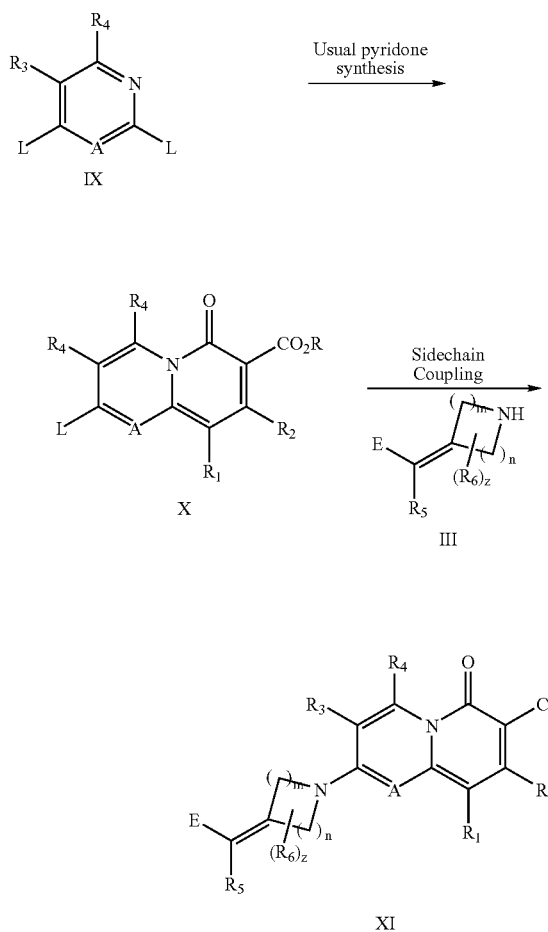

As before, where E is

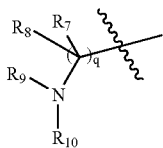

and at least one of $R_9$ and $R_{10}$ is hydrogen, it may be necessary to protect the terminal nitrogen to effect selective conversion to the desired product (Scheme IV). In such case, standard amine protecting groups known to those skilled in the art, such as t-butyloxycarbonyl (Boc), benzyloxycarbonyl (Cbz), benzyl (Bn), 9-fluorenylmethoxycarbonyl (Fmoc), allyloxycarbonyl (Alloc), 2-trimethylsilylethoxycarbonyl (Teoc), N-formyl, N-acetyl, N-benzoyl, or phthalimide, may be used to mask the terminal amine, as in compound V. Following side chain coupling, the protecting group may be removed under standard conditions known to those skilled in the art to obtain the desired product XIII. XIII may be further elaborated, for example by alkylation, to other compounds of the invention XIV.

Scheme IV

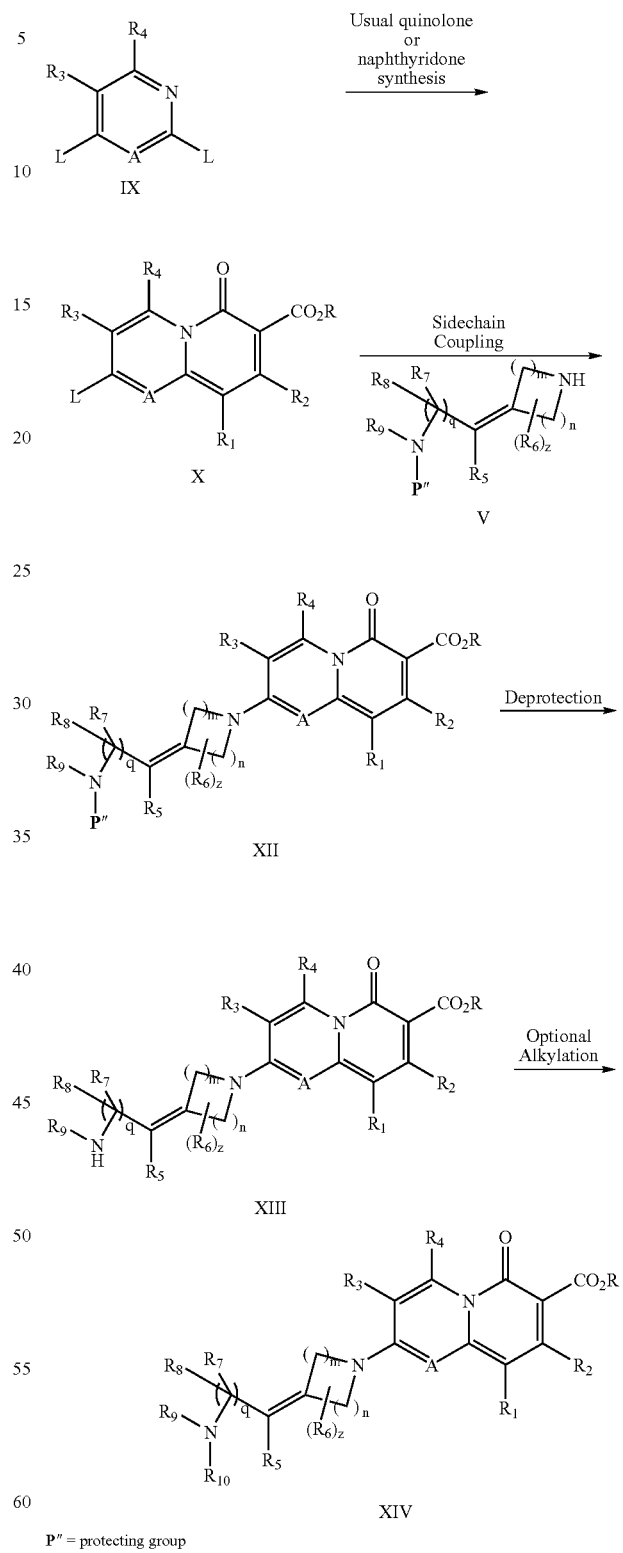

P″ = protecting group

Occasionally, side chain amines are insufficiently reactive to add efficiently to the heterocyclic nuclei (II or X) under the conditions illustrated in Schemes I–IV, particularly when A is C(R$_{11}$), wherein R$_{11}$ is alkoxy. The nucleus can be activated towards nucleophilic attack by the addition of a Lewis acid such as, but not limited to, boron trifluoride, triacetoxyborate, and lithium chloride. The preferred method of activation is described in U.S. Pat. No. 5,157,117. The quinolone nucleus is treated with triacetoxyborate, prepared in situ, in solvent such as, but not limited to, acetic acid or propionic acid and is heated for 1 to 24 h at a temperature between 60° C. and 120° C. The diacyl quinolinylborate (XV) is isolated by filtration after removal of the solvent. Scheme V illustrates this preferred method of activation.

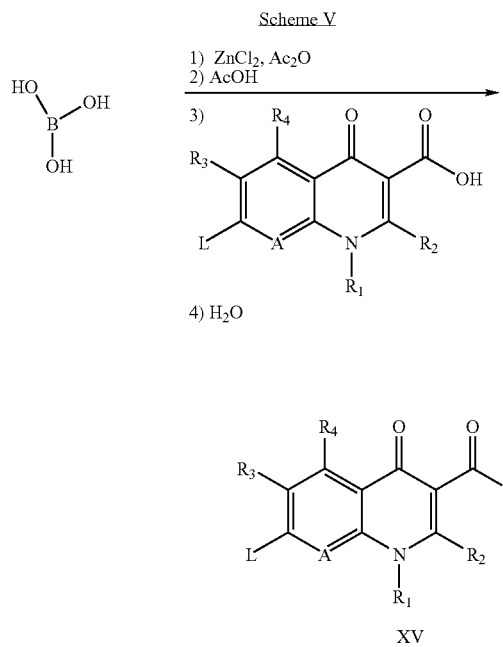

Precursor Preparation—Side Chain Amine III

Scheme VI illustrates the synthesis of the side chain amine III wherein E is

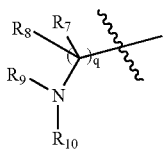

R$_7$ and R$_8$ are hydrogen, and q is 1. The trisubstituted or tetrasubstituted alkylidenes XX can be prepared by a Peterson, Wittig or Wadsworth-Horner-Emmons olefination of an appropriately substituted ketone (XVI) in a solvent such as, but not limited to, tetrahydrofuran, dimethylsulfoxide, or methylene chloride for 1 to 24 h at a temperature between −78° C. to 120° C. in the presence of a base such as, but not limited to, n-butyl lithium, sodium hydride or potassium carbonate. The resulting ester (XVII) can be reduced with a reducing agent such as, but not limited to, diisobutylaluminum hydride, lithium triethylborohydride or sodium borohydride in a solvent such as, but not limited to, toluene, methylene chloride, or tetrahydrofuran for 1 to 24 h at a temperature between 0° C. and 120° C. to afford the corresponding alcohol XVIII, where q=1. Converting the alcohol XVIII to leaving group XIX, such as, but not limited to, chloride, bromide, mesylate or tosylate under standard conditions and displacing the leaving group with an appropriately substituted amine in a solvent such as, but not limited to, dimethylformamide, dimethylsulfoxide, or tetrahydrofuran for 1 to 24 h at a temperature between 0° C. and 120° C. converts the alcohol XVIII to an amine XX. Removal of the protecting group, P, under standard conditions known to those skilled in the art affords amine III, wherein E is

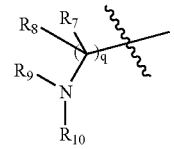

R$_7$ and R$_8$ are hydrogen, and q is 1. Alternatively, direct replacement of the alcohol XVIII can be accomplished via a Mitsunobu reaction with phthalimide and dialkyl azodicarboxylate to afford XXI. Deprotection of the phthalimide (XXI) with hydrazine in a solvent such as methanol or ethanol affords the amine (XX), wherein R$_9$ and R$_{10}$ are hydrogen. The protecting group, P, may be removed from XXI under standard conditions known to those skilled in the art to provide the amine V, wherein R$_7$ and R$_8$ are hydrogen and R$_9$ and P''' together with the nitrogen to which they are attached form a phthalimide group.

Scheme VI

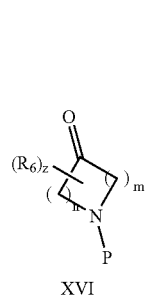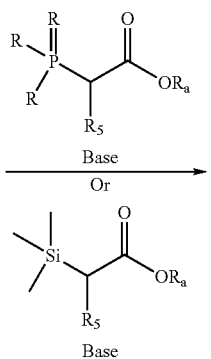

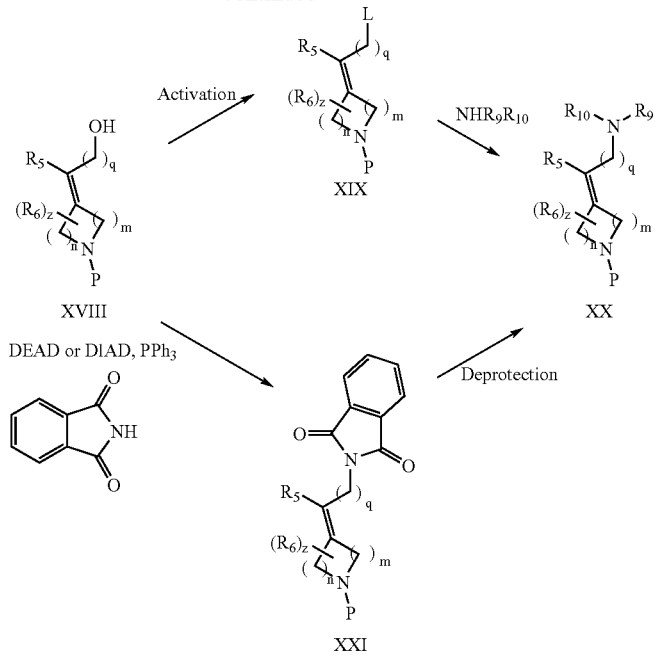

L is Leaving Group
P is Protecting Group

Scheme XXII illustrates the conversion of alcohols of formula XVIII to compounds of formula III, wherein E is alkenyl (LVIII). In addition, the Scheme outlines the synthesis of compounds of formula III, wherein E is

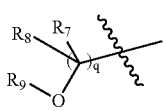

$R_7$ and $R_8$ are hydrogen and $R_9$ is acyl, alkoxycarbonyl, or sulfonyl (LX). Oxidation of alcohol XVIII with any of a number of suitable oxidizing agents, such as Dess-Martin periodinane, the Corey-Kim reagent, or the Swern reagent, affords the corresponding aldehyde (LVI). The aldehyde may be subjected to a base promoted olefination reaction, such as, but not limited to, the Wittig reaction to give LVII, wherein $R_c$ is hydrogen or alkyl. Removal of the protecting group, P, from LVII under standard conditions known to those skilled in the art affords amine III, wherein E is alkenyl (LVIII). Scheme XX also illustrates the conversion of alcohols of formula XVIII to compounds of formula III, wherein E is

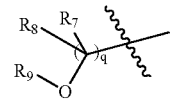

$R_7$ and $R_8$ are hydrogen, and $R_9$ is acyl, alkoxycarbonyl, or sulfonyl (LX). Reaction of alcohol XVIII with an acylating agent in the presence of an amine base, such as pyridine, in an inert solvent such as dichloromethane, tetrahydrofuran or toluene at temperatures ranging from −20° C. to 60° C. for from 1–48 hours provides compounds of formula III, wherein E is

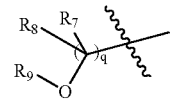

$R_7$ and $R_8$ are hydrogen and $R_9$ is acyl (LIX). Acylating agents include acid halides, acid anhydrides, and acids in the presence of an activating agent such as dicyclohexylcarbodiimide, EDCl, BOP-Cl, BOP, PyBOP, and the like. Alcohols of formula XVIII may be converted into compounds of formula III, wherein E is

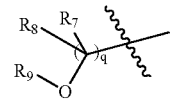

$R_7$ and $R_8$ are hydrogen and $R_9$ is alkoxycarbonyl (LIX) by reaction with a carbonylating agent in the presence of an amine base, such as pyridine, in an inert solvent such as dichloromethane, tetrahydrofuran or toluene at temperatures ranging from −20° C. to 60° C. for from 1–48 hours. Carbonylating agents include chloroformates, fluoroformates, azidoformates, and pyrocarbonates. Alcohols of formula XVIII may be converted into compounds of formula III, wherein E is

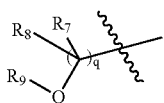

$R_7$ and $R_8$ are hydrogen and $R_9$ is sulfonyl (LIX) by reaction with a sulfonyl chloride or sulfonic anhydride in the presence of an amine base, such as pyridine, in an inert solvent such as dichloromethane, tetrahydrofuran or toluene at temperatures ranging from −20° C. to 60° C. for from 1–48 hours. Removal of the protecting group, P, from LIX under standard conditions known to those skilled in the art affords amine III, wherein E is

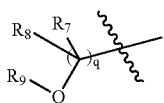

$R_7$ and $R_8$ are hydrogen, and $R_9$ is acyl, alkoxycarbonyl, or sulfonyl (LX).

Scheme VII illustrates a direct conversion of ketone XVI to olefin XX using a base promoted olefination reaction such as, but not limited to, the Wittig, Wadsworth-Horner-Emmons, or Peterson olefination procedures. Alternatively, amine XX could be prepared by an olefin metathesis procedure from terminal olefin XXII using an appropriately substituted amine XXIII. Removal of the protecting group, P, from XX under standard conditions known to those skilled in the art affords amine III, wherein E is

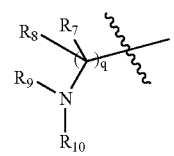

and $R_7$ and $R_8$ are hydrogen.

Scheme XXII

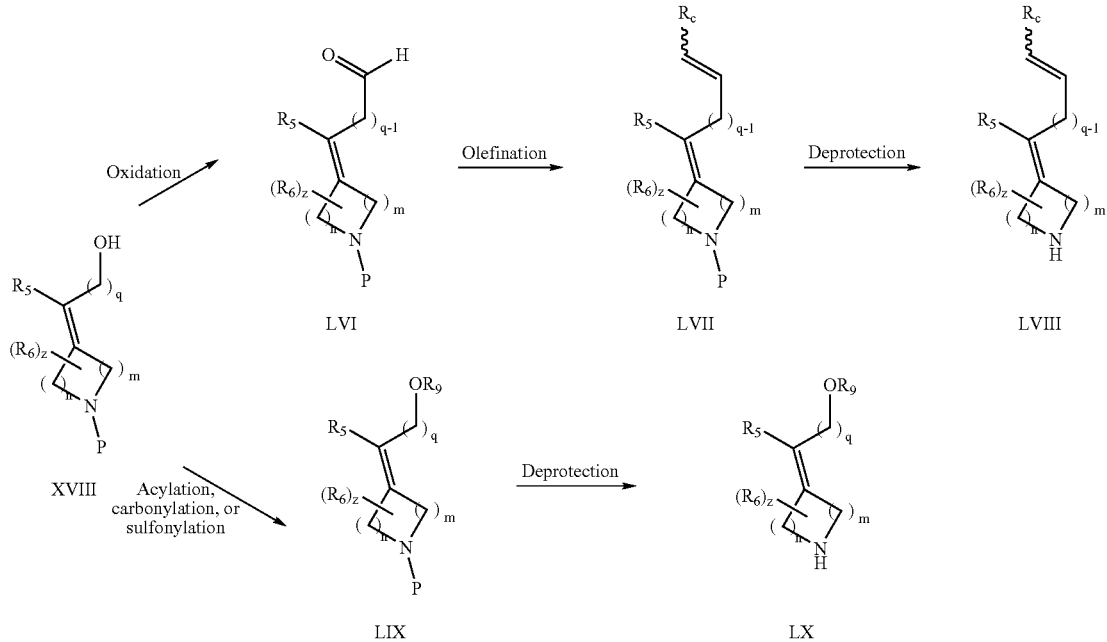

P is Protecting Group

Scheme VII

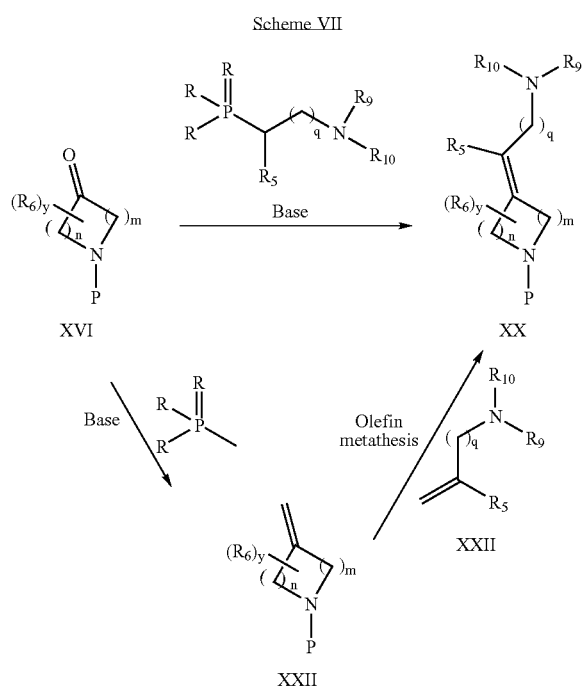

P is Protecting Group

Scheme VIII illustrates the hydroxylation of XXIV with selenium dioxide to afford the allylic alcohol XXV. The transformation is performed in a solvent such as, but not limited to, methylene chloride, toluene or tetrahydrofuran at a temperature between 25° C. and 150° C., optionally in the presence of a co-oxidant such as tert-butyl hydroperoxide. Removal of the protecting group, P, from XXV under standard conditions known to those skilled in the art affords amine III, wherein E is

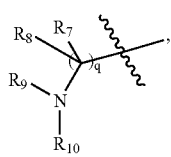

and one of $R_6$ is hydroxy.

Scheme VIII

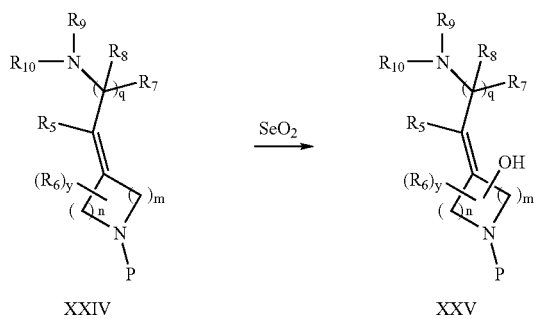

P is Protecting Group

Scheme IX illustrates the preparation of α,β-unsaturated carbonyl compound XXVI, where $R_7$ is as defined previously, using a Peterson, Wittig or Wadsworth-Horner-Emmons olefination procedure of an appropriately substituted ketone (XVI) in a solvent such as, but not limited to, tetrahydrofuran, dimethylsulfoxide, or methylene chloride for from 1 to 24 h at a temperature between −78° C. to 120° C. in the presence of a base such as, but not limited to, n-butyl lithium, sodium hydride or potassium carbonate. The resulting carbonyl compound (XXVI) can be reduced with a reducing agent such as, but not limited to, diisobutylaluminum hydride, lithium triethylborohydride or sodium borohydride in a solvent such as, but not limited to, toluene, methylene chloride, or tetrahydrofuran for from 1 to 24 h at a temperature between 0° C. and 120° C. to afford the corresponding alcohol XXVII. Alternatively, the carbonyl compound may undergo nucleophilic addition with an appropriately substituted organometallic agent ($R_8M$, wherein M is a metal), such as an organolithium species or a Grignard reagent, to afford the corresponding alcohol XXVII, where $R_8$ is alkyl. Suitable solvents for the latter transformation include, diethyl ether, tetrahydrofuran, or toluene, at temperatures ranging from −78° C. to 20° C. for from 30 minutes to 48 hours. Where one of $R_7$ or $R_8$ are hydrogen, converting the alcohol functionality in XXVII to a leaving group, such as, but not limited to, bromide, mesylate or tosylate as in XXVIII under standard conditions and displacing the leaving group with an appropriately substituted amine in a solvent such as, but not limited to, dimethylformamide, dimethylsulfoxide, or tetrahydrofuran for from 1 to 24 h at a temperature between 0° C. and 120° C. converts the alcohol XXVII to an amine XXX. Removal of the protecting group, P, from XXX under standard conditions known to those skilled in the art affords amine III, wherein E is

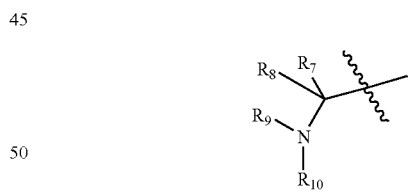

and one of $R_7$ and $R_8$ is hydrogen. Alternatively, where one of $R_7$ or $R_8$ is hydrogen, direct replacement of the alcohol XXVII can be accomplished via a Mitsunobu reaction with phthalimide and a dialkyl azodicarboxylate followed by deprotection of the phthalimide with hydrazine in a solvent such as methanol or ethanol to afford amine XXX. The protecting group, P, may be removed from XXIX under standard conditions known to those skilled in the art to provide the amine V, wherein $R_8$ is hydrogen and $R_9$ and P‴ together with the nitrogen to which they are attached form a phthalimide group.

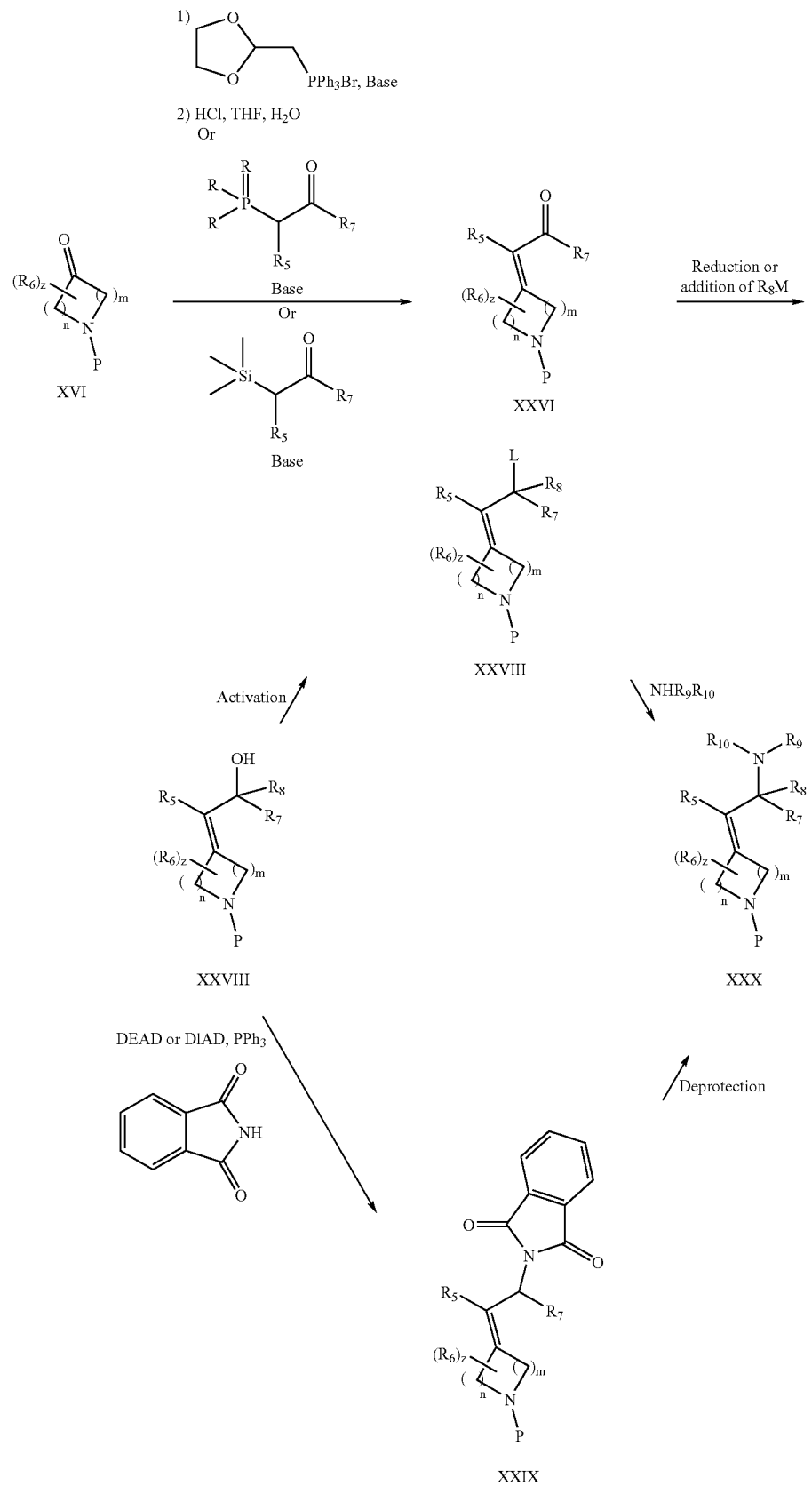
Scheme IX
L is Leaving Group
P is Protecting Group

Scheme X depicts the preparation of XXXVI, wherein $R_5$ is halogen. Alkylidenes XXXI, wherein $R_5$ is hydrogen, can be halogenated with an appropriate halogenating agent such as, but not limited to, 1-bromo-2,5-pyrrolidinedione, 1,1,1-tris(acetyloxy)-1,1-dihydro-2-benziodoxol-3(1H)-one and a tetraalkylammonium bromide, or thionyl chloride to provide XXXII. Alkylidene XXXII can be reduced with a reducing agent such as, but not limited to, diisobutylaluminum hydride, lithium triethylborohydride or sodium borohydride in a solvent such as, but not limited to, toluene, methylene chloride, or tetrahydrofuran for from 1 to 24 h at a temperature between 0° C. and 120° C. to afford the corresponding alcohol XXXIII. Alternatively, the carbonyl compound may undergo nucleophilic addition with an appropriately substituted organometallic agent, such as an organolithium species or a Grignard reagent, to afford the corresponding alcohol XXXIII, where $R_8$ is alkyl. Suitable solvents for the latter transformation include, diethyl ether, tetrahydrofuran, or toluene, at temperatures ranging from −78° C. to 20° C. for from 30 minutes to 48 hours. Where one of $R_7$ or $R_8$ is hydrogen, converting the alcohol functionality in XXXIII to a leaving group, such as, but not limited to, bromide, mesylate or tosylate as in XXXIV under standard conditions and displacing the leaving group with an appropriately substituted amine in a solvent such as, but not limited to, dimethylformamide, dimethylsulfoxide, or tetrahydrofuran for from 1 to 24 h at a temperature between 0° C. and 120° C. converts XXXIV to an amine XXXVI. Removal of the protecting group, P, from XXXVI under standard conditions known to those skilled in the art affords amine III, wherein E is

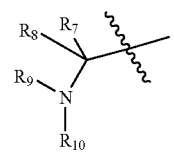

and one of $R_7$ and $R_8$ is hydrogen. Alternatively, where one of $R_7$ or $R_8$ is hydrogen, direct replacement of the alcohol XXXIII can be accomplished via a Mitsunobu reaction with phthalimide and a dialkyl azodicarboxylate followed by deprotection of the phthalimide with hydrazine in a solvent such as methanol or ethanol to afford the amine XXXVI. The protecting group, P, may be removed from XXXV under standard conditions known to those skilled in the art to provide the amine V, wherein $R_8$ is hydrogen and $R_9$ and P‴ together with the nitrogen to which they are attached form a phthalimide group.

Scheme X

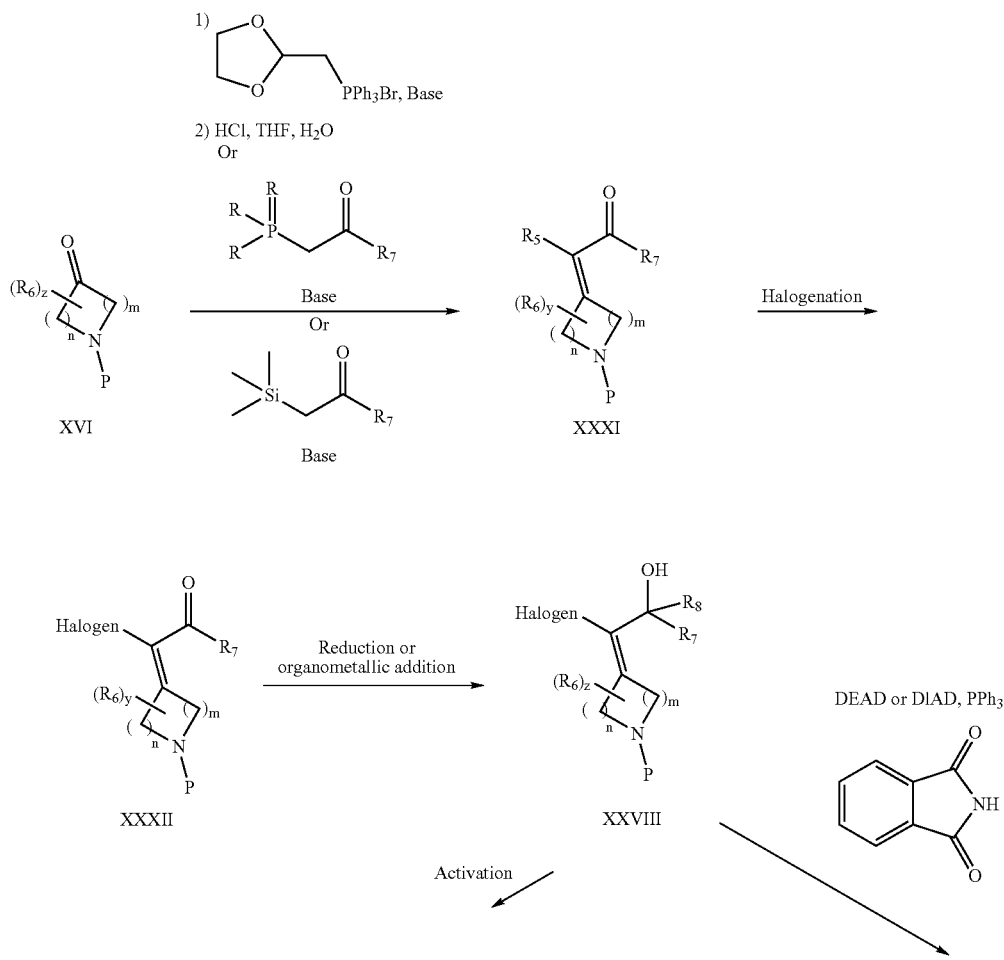

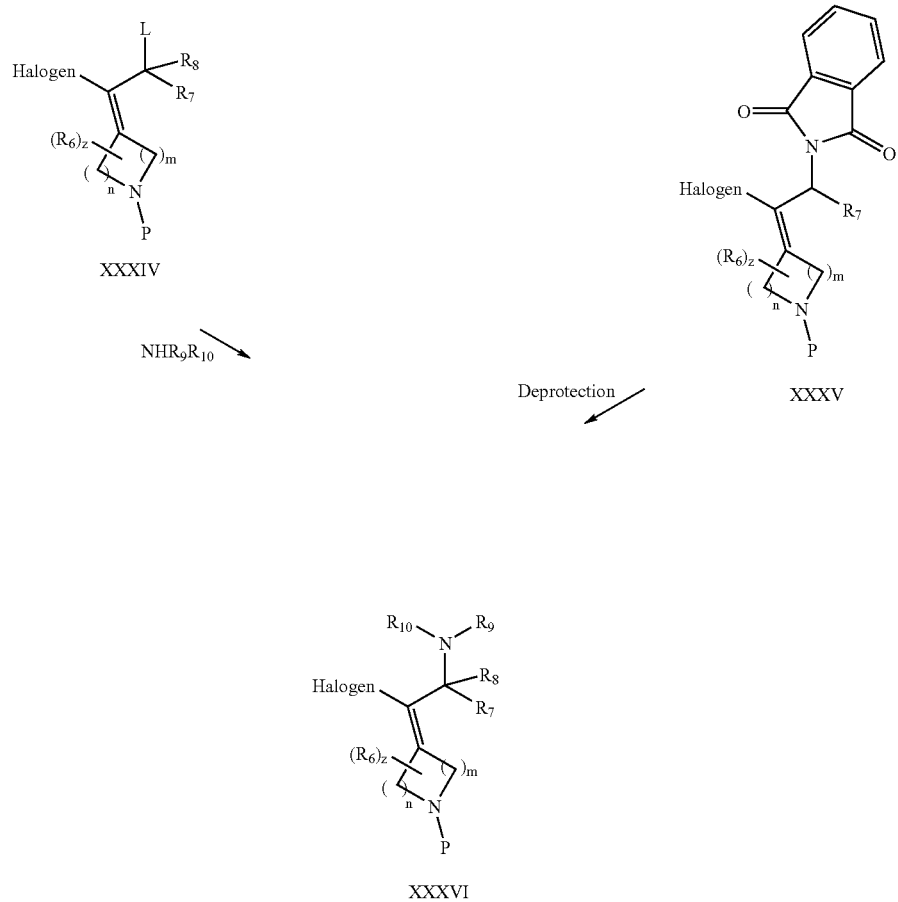

L is Leaving Group
P is Protecting Group

Scheme XI illustrates the synthesis of the side chain amine III wherein E is

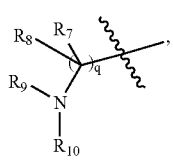

$R_7$ and $R_8$ are hydrogen and $R_5$ is substituted or branched-chain alkyl.

In Scheme XI, halogenated carbonyl compound XXXVII, wherein $R_a$ is hydrogen or alkyl, may be prepared in a similar fashion as halogenated carbonyl compound XXXII. Carbonyl compound XXXVII, wherein Ra is hydrogen or alkyl, may be reduced with a reducing agent such as, but not limited to, diisobutylaluminum hydride, lithium triethylborohydride or sodium borohydride in a solvent such as, but not limited to, toluene, methylene chloride, or tetrahydrofuran for from 1 to 24 h at a temperature between 0° C. and 120° C. to afford the corresponding alcohol XXXVIII where $R_a$ is hydrogen or alkyl, one of $R_b$ is hydrogen, and the other $R_b$ is hydroxyl. Alternatively, the carbonyl compound XXXVII, wherein $R_a$ is alkyl, may undergo nucleophilic addition with an appropriately substituted organometallic agent, such as an organolithium species or a Grignard reagent, to afford the corresponding alcohol XXXVIII where $R_a$ is alkyl, one of $R_b$ is alkyl, and the other $R_b$ is hydroxyl. Finally, carbonyl compound XXXVII, wherein $R_a$ is hydrogen or alkyl, or alcohol XXXVIII, wherein $R_a$ is hydrogen or alkyl, one of $R_b$ is hydrogen, and the other $R_b$ is hydroxyl, may be fluorinated using a nucleophilic fluorinating reagent, such as but not limited to, (N-ethylethanaminato)trifluorosulfur (DAST) or bis(2-methoxyethyl)aminosulfur trifluoride (Deoxofluor), in a suitable solvent, such as methylene chloride, for from 1 to 24 h at a temperature between 0° C. and 60° C. to afford XXXVIII, where in the case of the carbonyl compound XXXVII as substrate, $R_a$ is hydrogen or alkyl and $R_b$ is fluorine, and where in the case of the alcohol XXXVIII as substrate, $R_a$ is hydrogen or alkyl, one of $R_b$ is hydrogen, and the other $R_b$ is fluorine. Halogenated alkylidene XXXVIII may be carbonylated in the presence of a transition metal catalyst, such as but not limited to palladium acetate, dicarbonylbis(triphenylphosphine)nickel, or tetrakis (triphenylphosphine)palladium, under an atmosphere of carbon monoxide in the presence of a second additive such as methanol, optionally as solvent, or in a solvent such as, but not limited to, dimethylsulfoxide or tetrahydrofuran, for 1 to 24 h at a temperature between 0° C. and 120° C. to afford ester XXXIX. XXXIX may be reduced with a reducing agent such as, but not limited to, diisobutylaluminum hydride, lithium triethylborohydride or sodium borohydride in a solvent such as, but not limited to, toluene, methylene chloride, or tetrahydrofuran for 1 to 24 h at a temperature between 0° C. and 120° C. to afford the corresponding alcohol XL, where q=1. Converting the alcohol XL to leaving group XLI, such as, but not limited to, bromide, mesylate or tosylate, under standard conditions and displacing the leaving group with an appropriately substituted amine in a solvent such as, but not limited to, dimethylformamide, dimethylsulfoxide, or tetrahydrofuran for from 1 to 24 h at a temperature between 0° C. and 120° C. converts the alcohol XL to an amine XLIII. Removal of the protecting group, P, from XLIII under standard conditions known to those skilled in the art affords amine III, wherein E is

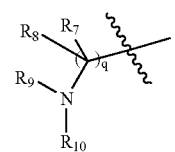

$R_7$ and $R_8$ are hydrogen and $R_5$ is $CR_aR_aR_b$. Alternatively, direct replacement of the alcohol XL may be accomplished via a Mitsunobu reaction with phthalimide and dialkyl azodicarboxylate to afford XLII. Deprotection of the phthalimide XLII with hydrazine in a solvent such as methanol or ethanol affords the amine XLIII. The protecting group, P, may be removed from XLII under standard conditions known to those skilled in the art to provide the amine V, wherein $R_7$ and $R_8$ are hydrogen, $R_9$ and P'" together with the nitrogen to which they are attached form a phthalimide group, and $R_5$ is $CR_aR_aR_b$.

Scheme XI

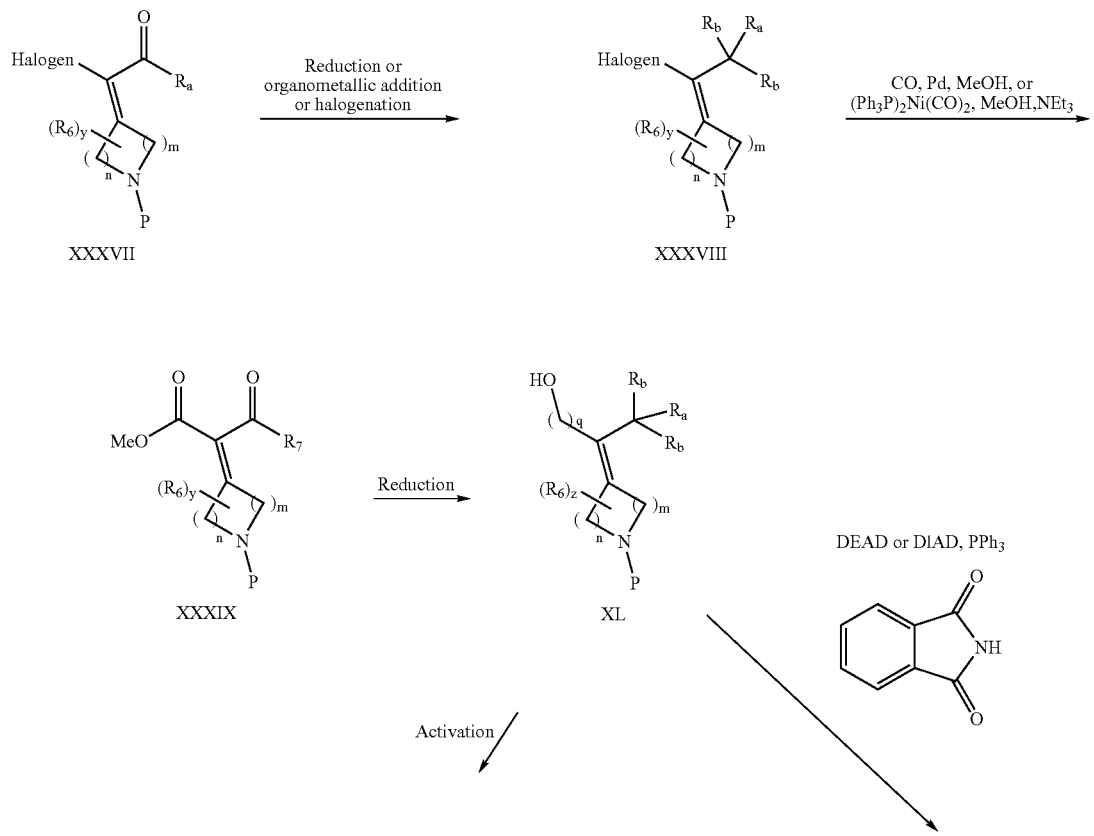

-continued

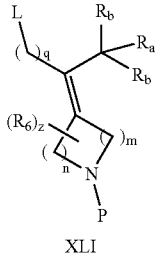

XLI

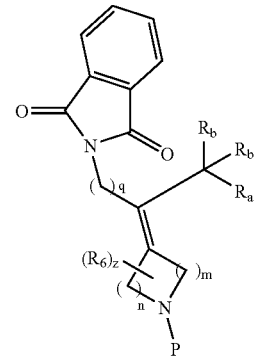

XLIII

NHR₉R₁₀ ↘    Deprotection ↙

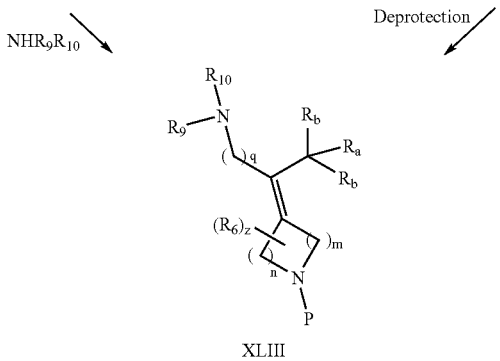

XLIII

L is Leaving Group
P is Protecting Group

Scheme XII illustrates the synthesis of the side chain amine III wherein E is

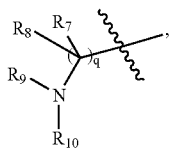

one of $R_7$ or $R_8$ is hydrogen and the other is alkyl, $R_5$ is substituted or branched-chain alkyl, and q is 1. Compound XXXVIII, prepared as described above, may be carbonylated in the presence of a transition metal catalyst, such as but not limited to palladium acetate, dicarbonylbis(triphenylphosphine)nickel, or tetrakis (triphenylphosphine)palladium, under an atmosphere of carbon monoxide in the presence of an organometallic reagent $R_7M$, wherein $R_7$ is defined previously and includes reagents such as tributyltinhydride or alkyl indium agents (Organic Letters 2003, 5(7), 1103–1106), in a solvent such as, but not limited to, methanol, dimethylsulfoxide, or tetrahydrofuran for 1 to 24 h at a temperature between 0° C. and 120° C. to afford XLIV, where $R_7$ is as previously defined. Carbonyl compound XLIV may be reduced with a reducing agent such as, but not limited to, diisobutylaluminum hydride, lithium triethylborohydride or sodium borohydride in a solvent such as, but not limited to, toluene, methylene chloride, or tetrahydrofuran for from 1 to 24 h at a temperature between 0° C. and 120° C. to afford the corresponding alcohol XLV. Alternatively, the carbonyl compound may undergo nucleophilic addition with an appropriately substituted organometallic reagent, such as an organolithium species or a Grignard reagent, to afford the corresponding alcohol XLV, where $R_8$ is alkyl. Suitable solvents for the latter transformation include, diethyl ether, tetrahydrofuran, or toluene, at temperatures ranging from −78° C. to 20° C. for from 30 minutes to 48 hours. Where one of $R_7$ or $R_8$ are hydrogen, converting the alcohol functionality in XLV to a leaving group, such as, but not limited to, bromide, mesylate or tosylate as in XLVI under standard conditions and displacing the leaving group with an appropriately substituted amine in a solvent such as, but not limited to, dimethylformamide, dimethylsulfoxide, or tetrahydrofuran for from 1 to 24 h at a temperature between 0° C. and 120° C. converts the alcohol XLV to an amine XLVIII. Removal of the protecting group, P, from XLVIII under standard conditions known to those skilled in the art affords amine III, wherein E is

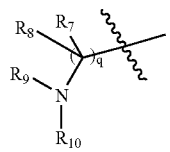

one of $R_7$ and $R_8$ is hydrogen and the other is alkyl, $R_5$ is substituted or branched-chain alkyl, and q is 1. Alternatively, where one of $R_7$ or $R_8$ is hydrogen, direct replacement of the alcohol XLV can be accomplished via a Mitsunobu reaction with phthalimide and a dialkyl azodicarboxylate followed by deprotection of the phthalimide with hydrazine in a solvent such as methanol or ethanol to afford amine XLVIII. The protecting group, P, may be removed from XLVIII under standard conditions known to those skilled in the art to provide the amine V, wherein one of $R_7$ and $R_8$ is hydrogen and the other is alkyl, $R_9$ and P'' together with the nitrogen to which they are attached form a phthalimide group, $R_5$ is substituted or branched-chain alkyl, and q is 1.

Scheme XIII illustrates the conversion of ketone XVIa to olefin LII using a base promoted Stork-Jung vinylsilane Robinson annulation protocol (Tetrahedron Letters, 2001, 42, 9123). Condensation of ketone XVIa with allyl iodide

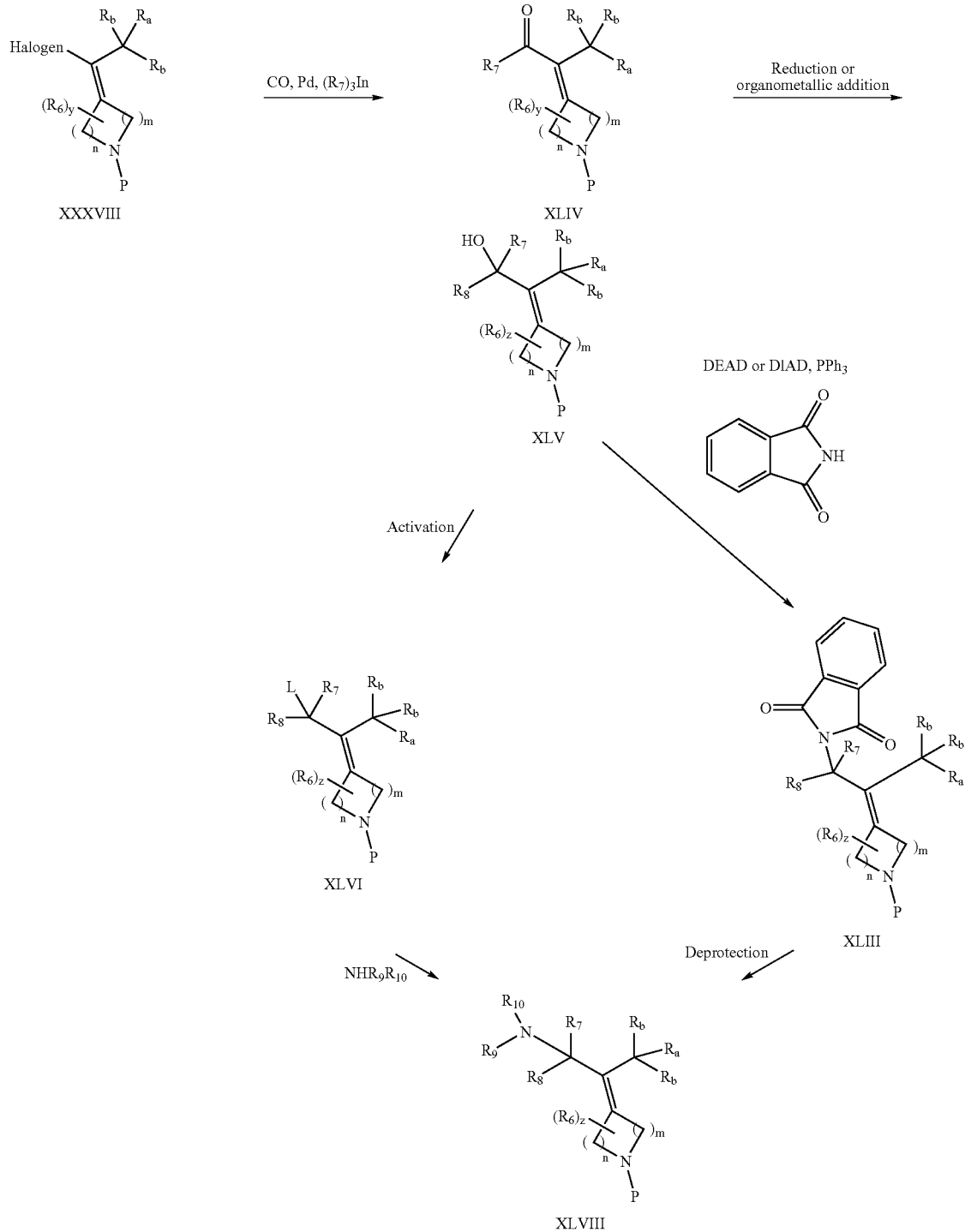

L is Leaving Group
P is Protecting Group

XLIX, wherein $R_c$ is an alkyl group and P' is a hydroxy protecting group, (Tetrahedron Letters, 2001, 42, 9123) affords alkylated ketone L. Epoxidation of ketone L with epoxidizing agents such as, but not limited to, dimethyl dioxirane or m-chloroperbenzoic acid, affords oxirane LI. Protodesilylation of LI with agents such as, but not limited to, tetra-n-butylammonium fluoride or pyridinium poly(hydrogen fluoride) and aqueous acid, with concomitant epoxide ring opening affords ketone LII. Ring annulation of LII may be accomplished by treatment of LII with a base, such as but not limited to, sodium methoxide to afford LIII. α,β-Unsaturated ketone LIII may be reduced with a reducing agent such as, but not limited to, diisobutylaluminum hydride, lithium triethylborohydride or sodium borohydride in a solvent such as, but not limited to, toluene, methylene chloride, or tetrahydrofuran for from 1 to 24 h at a temperature between 0° C. and 120° C. to afford, following removal of the hydroxy protecting group, the corresponding alcohol LIV, wherein one of $R_{12}$ is hydrogen and the other $R_{12}$ is hydroxy. Alternatively, LIII may undergo nucleophilic addition with an appropriately substituted organometallic reagent, such as an organolithium species or a Grignard reagent, to afford, following removal of the hydroxy protecting group, the corresponding alcohol LIV, where one of $R_{12}$ is alkyl and the other $R_{12}$ is hydroxy. Suitable solvents for the latter transformation include, diethyl ether, tetrahydrofuran, or toluene, at temperatures ranging from −78° C. to 20° C. for from 30 minutes to 48 hours. Finally, carbonyl compound LIII, may be fluorinated using a nucleophilic fluorinating reagent, such as but not limited to, (N-ethylethanaminato)trifluorosulfur (DAST) or bis(2-methoxyethyl)aminosulfur trifluoride (Deoxofluor), in a suitable solvent, such as methylene chloride, for from 1 to 24 h at a temperature between 0° C. and 60° C. to afford, following removal of the hydroxy protecting group, alcohol LIV, where $R_{12}$ is fluorine.

Scheme XIII

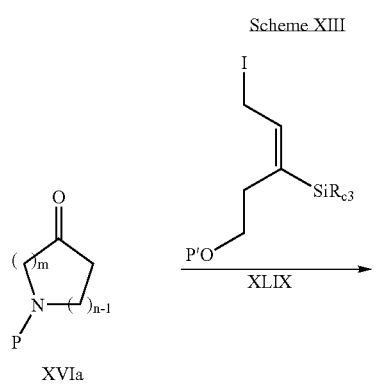

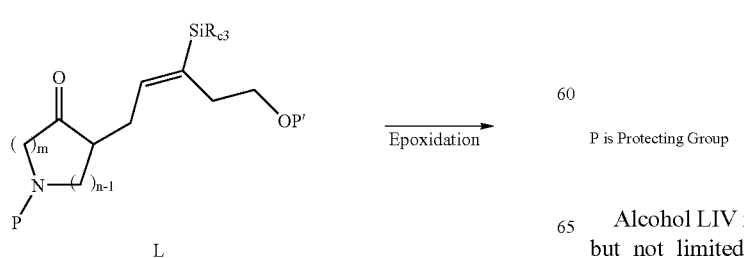

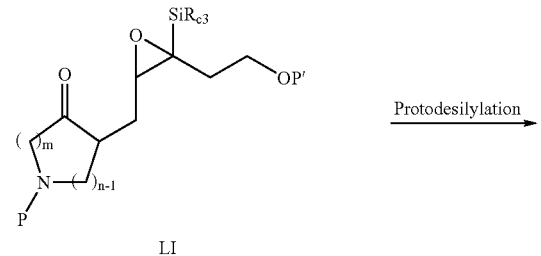

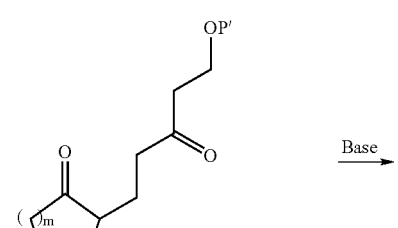

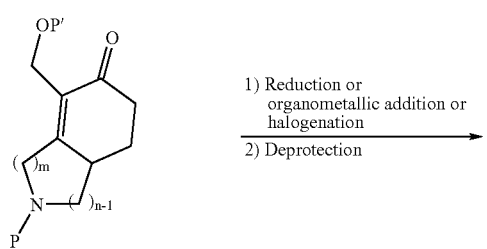

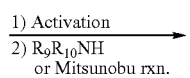

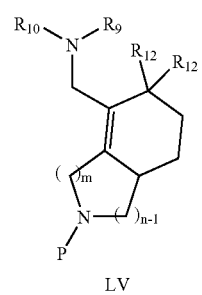

P is Protecting Group

Alcohol LIV may be converted to leaving group, such as, but not limited to, bromide, mesylate or tosylate under standard conditions. Displacement of the leaving group with an appropriately substituted amine in a solvent such as, but not limited to, dimethylformamide, dimethylsulfoxide, or tetrahydrofuran for from 1 to 24 h at a temperature between 0° C. and 120° C. converts LIV to amine LV. Removal of the protecting group, P, from LV under standard conditions known to those skilled in the art affords the corresponding secondary amine III, wherein E is

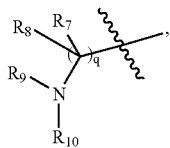

$R_7$ and $R_8$ are hydrogen, and $R_5$ and $R_6$ join to form a 6-membered carbocyclic ring, and q is 1.

Alternatively, direct replacement of the hydroxyl group of alcohol LIV can be accomplished via a Mitsunobu reaction with phthalimide and a dialkyl azodicarboxylate, followed by deprotection of the phthalimide with hydrazine in a solvent such as methanol or ethanol, to afford the amine LV, wherein $R_9$ and $R_{10}$ are hydrogen.

Experimental Section

Precursor Preparation—Heterocyclic Nuclei

All heterocyclic nuclei such as 1-cyclopropyl-1,4-dihydro-6,7-difluoro-8-methoxy-4-oxo-quinoline-3-carboxylic acid, 7-chloro-1-cyclopropyl-6-fluoro-4-oxo-1,4-dihydro-naphthpyridine-3-carboxylic acid, 9,10-difluoro-2,3-dihydro-3-methyl-7-oxo-7H-pyrido[1,2,3-de]-1,4-benzoxazine-6-carboxylic acid, 1-cyclopropyl-1,4-dihydro-6,7-difluoro-4-oxo-quinoline-3-carboxylic acid, 7-chloro-1-(2,4-difluorophenyl)-6-fluoro-4-oxo-1,4-dihydro-naphthyridine-3-carboxylic acid and 1-cyclopropyl-1,4-dihydro-7-fluoro-8-methoxy-4-oxo-quinoline-3-carboxylic acid were prepared according to literature methods (see above discussion about general procedures for preparing heterocyclic nuclei) or were purchased from commercial sources.

Precursor Preparation A—Preparation of Diacyl Quinolinyl Borates

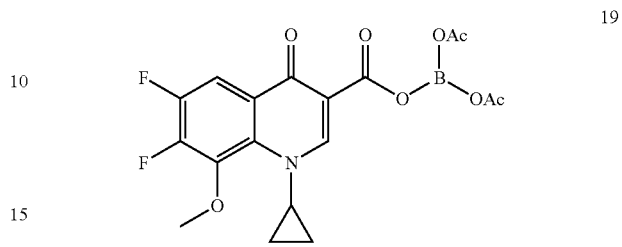

Compound 19 (Formula XV: L=F, A=C—OMe, $R_1$=Cyclopropyl, $R_2$=H, $R_3$=F, $R_4$=H)

The diacyl quinolinyl borates were prepared by the procedure reported in U.S. Pat. No. 5,157,117. A mixture of boric acid (2.4 g, 38.7 mmol), acetic anhydride (13.8 mL, 146 mmol) and zinc chloride (52 mg, 0.38 mmol) was warmed to 110° C. for 1.5 h, treated with acetic acid (51 mL) and was allowed to stir an additional hour at 110° C. The resulting mixture was allowed to cool to 60° C., treated with 1-cyclopropyl-1,4-dihydro-6,7-difluoro-8-methoxy-4-oxo-quinoline-3-carboxylic acid (18) (7.3 g, 25.9 mmol) and acetic acid (26 mL). The resulting solution was warmed to 60° C. for 5 h, cooled to room temperature, and was concentrated in vacuo. The residue was treated with water (50 mL) and the solid was collected by filtration. The resulting solid was washed with water (3×50 mL), and dried to afford the title compound as a white solid, which was used as such in the next reaction.

The same procedure as above was used to convert each of the respective heterocyclic carboxylic acids listed in Table 2 to the corresponding diacylborate derivative (17, 21, 23, and 83).

TABLE 2

| Compound | Quinolone | Compound | Diacyl Quinonyl Borate |
|---|---|---|---|
| 16 | ![structure] | 17 | ![structure] |
| 20 | ![structure] | 21 | ![structure] |

TABLE 2-continued
| Compound | Quinolone | Compound | Diacyl Quinonyl Borate |
|---|---|---|---|
| 22 | | 23 | |
| 82 | | 83 | |
Precursor Preparation B—Side Chain III
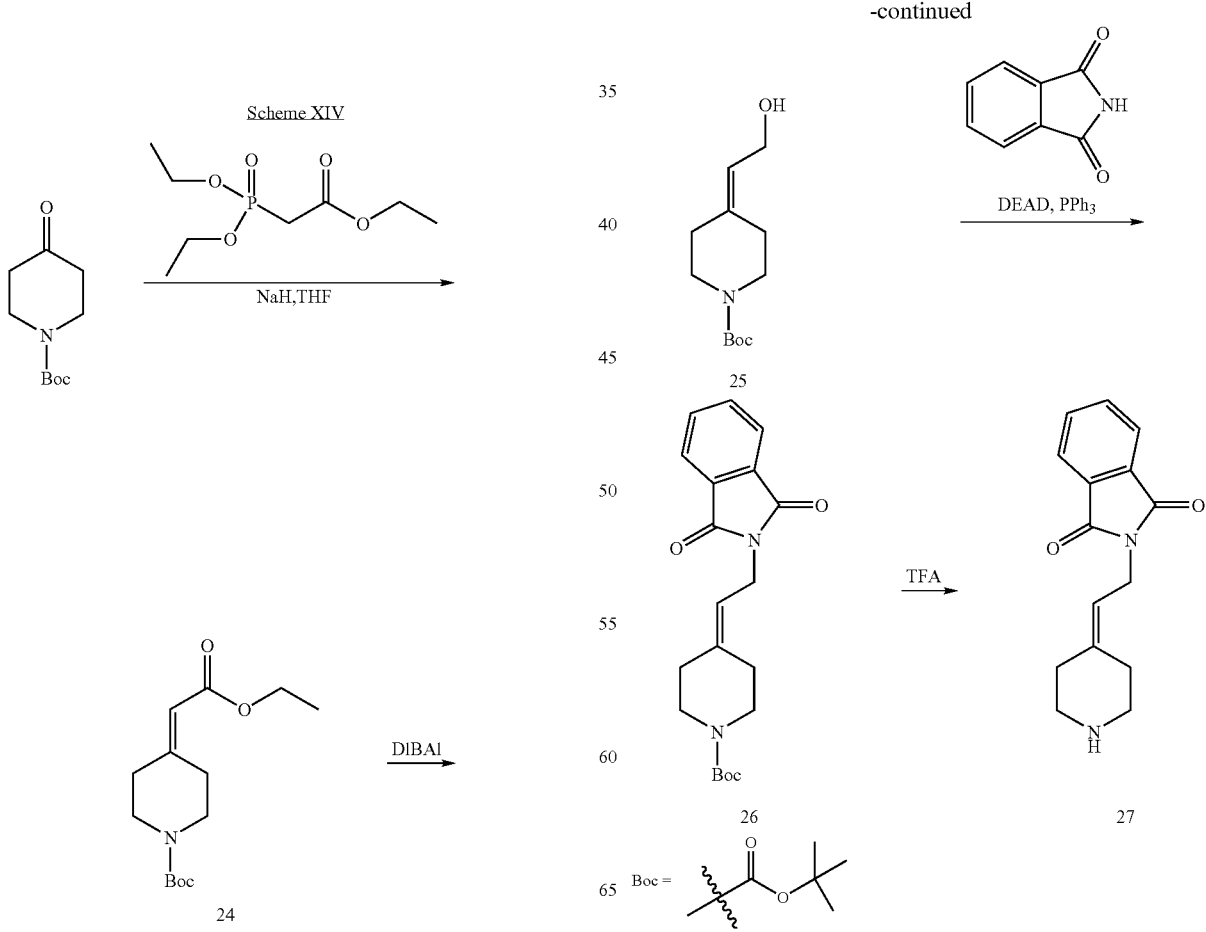

Compound 27 of Scheme XIV:

t-Butyl 4-(2-Ethoxy-2-oxoethylidene)piperidinyl-1-carboxylate (24) was prepared according the procedure described in Sato et al. *Heterocycles,* 2001, 54, 747.

t-Butyl 4-(2-Hydroxyethylidene)piperidinyl-1-carboxylate (25) was prepared according the procedure described in Sato et. al *Heterocycles,* 2001, 54, 747.

t-Butyl 4-[2-(1,3-Dihydro-1,3-dioxo-2H-isoindol-2-yl)ethylidene]-piperidinyl-1-carboxylate (26) was prepared by a procedure adapted from *Synthesis* 1995, 756. A solution of 25 (250 mg, 1.10 mmol), phthalimide (208 mg, 1.40 mmol), and triphenylphosphine (366 mg, 1.40 mmol) in dry THF (10 mL) was treated with diethyl azodicarboxylate (0.25 mL, 1.40 mmol) added via syringe in the dark under nitrogen. After 5 h, the reaction mixture was treated with water (10 mL), diluted with ethyl acetate (50 mL), washed with 10% aqueous sodium bicarbonate (2×25 mL), and dried (MgSO$_4$). Purification by flash chromatography (0–30% ethyl acetate/hexanes) afforded the title compound (389 mg, 78%) as a white foam. MS 357 (M+H).

4-[2-(1,3-dihydro-1,3-dioxo-2H-isoindol-2-yl)ethylidene]-1-piperidine trifluoroacetate (27). A solution of 26 (380 mg, 1.03 mmol) was dissolved in CH$_2$Cl$_2$ (50 mL) and was treated with trifluoroacetic acid (1 mL) at room temperature. After 1 h, the reaction mixture was concentrated in vacuo to afford the title compound 27 (363 mg, 100%) as an oil. MS 257 (M+H).

1-(tert-Butoxycarbonyl)-4-piperidinone was reacted with each of the respective phosphonoacetates listed in Table 3, and the products subjected to analogous procedures as in the synthesis of 27, to prepare the corresponding alcohols (28–30, 84) and the derived amines (31–33, 85).

TABLE 3

| Phosphonoacetates | Compound | Alcohols | (M + H) | Compound | Amines | (M + H) |
|---|---|---|---|---|---|---|
| (phosphonoacetate with F) | 28 | (alcohol with F) | 246 | 31 | (phthalimide amine with F) | 275 |
| (phosphonoacetate with Me) | 29 | (alcohol with Me) | 242 | 32 | (phthalimide amine with Me) | 271 |

TABLE 3-continued

| Phosphonoacetates | Compound | Alcohols | (M + H) | Compound | Amines | (M + H) |
|---|---|---|---|---|---|---|
| (structure) | 30 | (structure) | 262 | 33 | (structure) | 291 |
| (structure) | 84 | (structure) | 256 | 85 | (structure) | 285 |

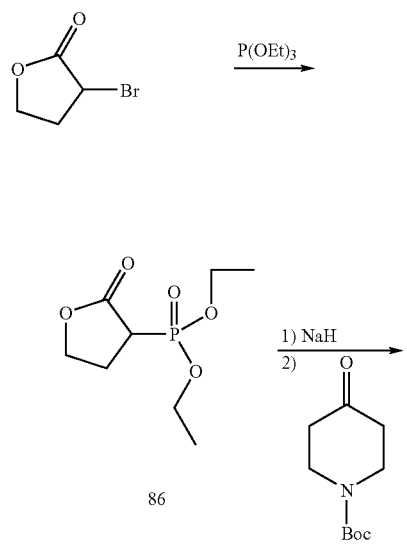

(2-Oxo-tetrahydro-furan-3-yl)-phosphonic acid diethyl ester (86; Scheme XXIII) was prepared according the procedure described in Murphy et al. *Chemical Communications* 1996, 6, 737–8.

4-(2-Oxo-dihydrofuran-3-ylidene)piperidine-1-carboxylic acid tert-butyl ester (87; Scheme XXIII) was prepared by an analogous procedure to that described in Sato et al. *Heterocycles*, 2001, 54, 747; MS=267 (M+H).

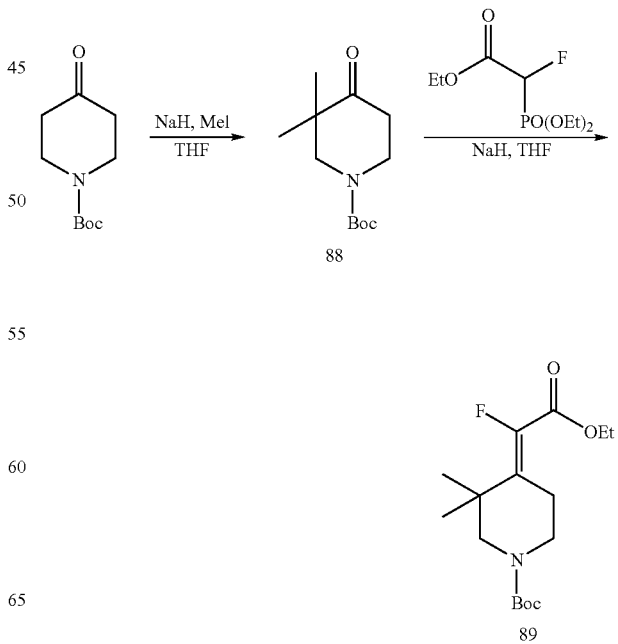

3,3-Dimethyl-4-oxo-piperidine-1-carboxylic acid tert-butyl ester (88; Scheme XXIV) was prepared according the procedure described in Vice et al. *J. Org. Chem.* 2001, 66, 2487–2492.

4-(2-Ethoxy-1-fluoro-2-oxoethylidene)-3,3-dimethylpiperidine-1-carboxylic acid tert-butyl ester (89; Scheme XXIV) was prepared by a procedure analogous to that described in Sato et al. *Heterocycles,* 2001, 54, 747.

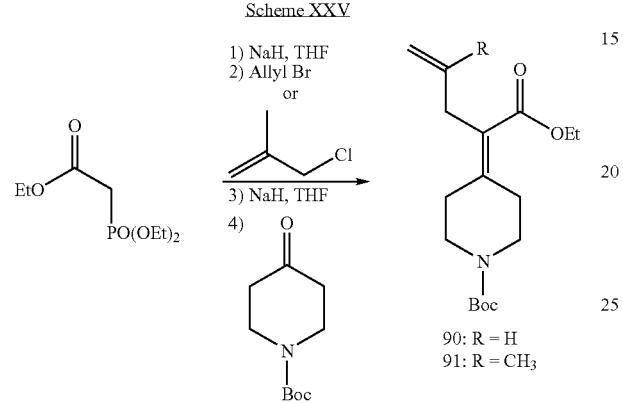

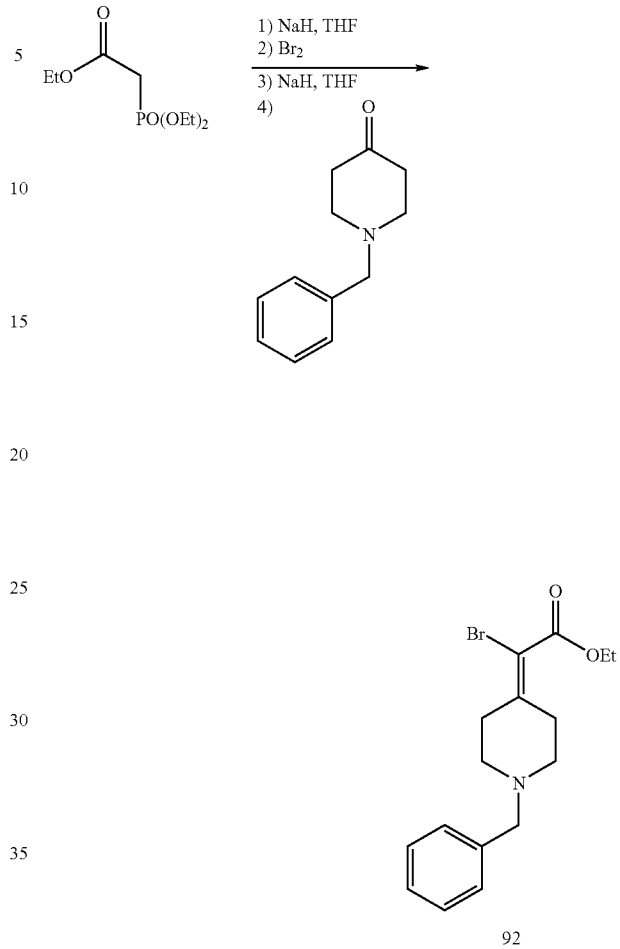

4-(1-Ethoxycarbonyl-but-3-enylidene) piperidine-1-carboxylic acid tert-butyl ester (90; Scheme XXV). A slurry of sodium hydride (1.50 g, 37.6 mmol) in THF (100 mL) at 0° C. under nitrogen was carefully treated with triethyl phosphonoacetate (8.12 mL, 37.6 mmol) via a syringe. After 30 min, the reaction mixture was treated with allyl bromide (3.3 mL, 37.6 mmol) and the resulting mixture was allowed to warm to 25° C. over 12 h. The resulting mixture was recooled to 0° C., treated with sodium hydride (1.50 g, 37.6 mmol), and the resulting slurry was allowed to stir for 30 min at 0° C. A solution of 1-(tert-butoxycarbonyl)-4-piperidinone (5.0 g, 25 mmol) in THF (50 mL) was added via a cannula over 10 min and the resulting solution was allowed to warm to 25° C. over 12 h. The reaction was quenched by the addition of 15% aqueous sodium bicarbonate (50 mL) and the resulting mixture was diluted with ethyl acetate (100 mL), washed with 15% aqueous sodium bicarbonate (2×100 mL), and concentrated in vacuo. Purification by chromatography (0–50% EtOAc/hexanes) afforded title compound (1.93 g, 25%) as a yellow oil: MS (M+H)=310.

4-(1-Ethoxycarbonyl-3-methyl-but-3-enylidene)piperidine-1-carboxylic acid tert-butyl ester (91; Scheme XXV) was prepared according to the procedure described for 90 except methylallyl chloride was used instead of allyl bromide.

(1-Benzyl-piperidin-4-ylidene)bromoacetic acid ethyl ester (92; Scheme XXVI). A slurry of sodium hydride (1.50 g, 37.6 mmol) in THF (100 mL) at 0° C. under nitrogen was carefully treated with triethyl phosphonoacetate (8.12 mL, 37.6 mmol) via a syringe. After 30 min, the reaction mixture was treated with bromine (1.95 mL, 37.6 mmol) via a dropping funnel over 10 min and the resulting mixture was allowed to stir for 3 h. The reaction mixture was treated with sodium hydride (1.50 g, 37.6 mmol) and the resulting slurry was allowed to stir for 30 min at 0° C. A solution of 1-benzylpiperidin-4-one (5.0 g, 25 mmol) in THF (50 mL) was added via a cannula over 10 min and the resulting solution was allowed to warm to 25° C. over 12 h. The reaction was quenched by the addition of 15% aqueous sodium bicarbonate (50 mL) and the resulting mixture was diluted with ethyl acetate (100 mL), washed with 15% aqueous sodium bicarbonate (2×100 mL), and concentrated in vacuo. Purification by chromatography (0–50% EtOAc/hexanes) afforded the title compound (6.35 g, 74%) as a red-orange oil: MS (M+=H)=339.

The alcohols listed in Table 6 were prepared in a similar fashion as described for t-butyl 4-(2-hydroxyethylidene) piperidinyl-1-carboxylate (25), except the corresponding ethylidene carboxylate was used instead of t-butyl 4-(2-ethoxy-2-oxoethylidene)piperidinyl-1-carboxylate (24).

TABLE 6

| Ethylidine Carboxylate | Alcohols | Compound | (M + H) |
|---|---|---|---|
| 93 | | 94 | 272 |
| 95 | | 96 | 274 |
| 97 | | 98 | 268 |
| 99 | | 100 | 282 |

TABLE 6-continued

| Ethylidine Carboxylate | Alcohols | Compound | (M + H) |
|---|---|---|---|
| 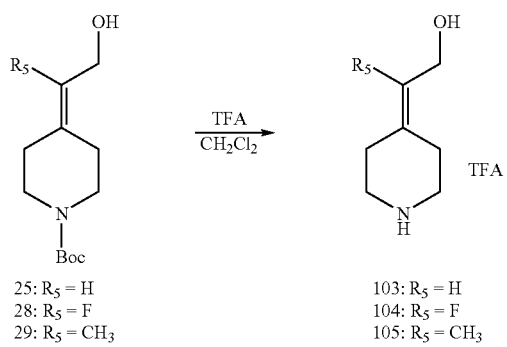 | | 102 | 297 |
| 101 | | | |

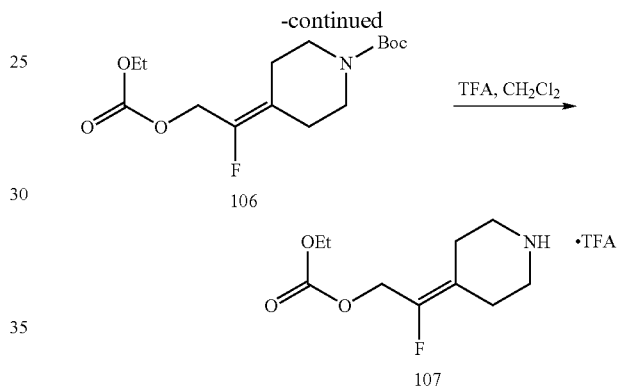

2-Piperidin-4-ylidene-ethanol trifluoroacetate (103; Scheme XXVII). A solution of 25 (191 mg, 0.5 mmol) was dissolved in $CH_2Cl_2$ (10 mL) and was treated with trifluoroacetic acid (0.5 mL) at room temperature. After 1 h, the reaction mixture was concentrated in vacuo to afford the title compound (64 mg, 100%) as an oil. MS 129 (M+H).

2-Piperidin-4-ylidene-propan-1-ol trifluoroacetate (105; Scheme XXVII) was prepared according the procedure described for 103 except 29 was used. MS 142 (M+H).

2-Fluoro-2-piperidin-4-ylidene-ethanol trifluoroacetate (104; Scheme XXVII) was prepared according the procedure described for 103 except 28 was used. MS 146 (M+H).

t-Butyl 4-(2-ethoxycarbonyloxy-1-fluoroethylidene)piperidine-1-carboxylate (106; Scheme XXVIII). To alcohol 28 (0.5064 g, 2.064 mmols) in $CH_2Cl_2$ (10 mL) at RT was added pyridine (0.23 mL, 2.8 mmols) and then ethyl chloroformate (0.22 mL, 2.2 mmols). After stirring overnight, sat. aq. $NH_4Cl$ (10 mL) was added and the mixture extracted with $CH_2Cl_2$ (5×10 mL), dried over $Na_2SO_4$, concentrated and chromatographed on silica (20% EtOAc/hexane as eluent) to provide the title compound 106 (0.4546 g, 69%) as a clear oil. MS 318 (M+H).

4-(2-Ethoxycarbonyloxy-1-fluoro-ethylidene)-piperidine (107; Scheme XXVIII). To compound 106 (0.1787 g, 0.5631 mmol) in $CH_2Cl_2$ (3 mL) was added TFA (0.56 mL, 7.3 mmols) and the mixture stirred for 3 hrs whereupon all volatile materials were removed in vacuo to provide the crude title compound, which was used without further purification. MS 218 (M+H).

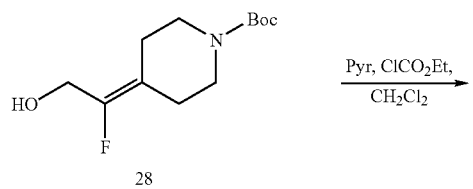

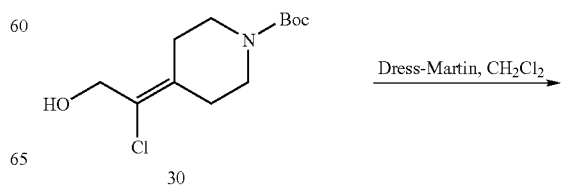

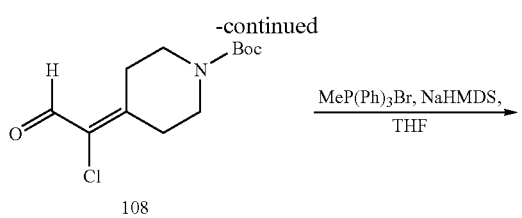

t-Butyl 4-(1-chloro-2-oxoethylidene)-piperidine-1-carboxylate (108; Scheme XXIX) To alcohol 30 (6.01 g, 23.0 mmols) in $CH_2Cl_2$ at RT and open to the air was added the Dess-Martin reagent (21.17 g, 49.9 mmols) and the reaction mixture stirred overnight whereupon the mixture was washed with sat. aq. $Na_2S_2O_3$ (60 mL) and sat. aq. $NaHCO_3$ (3×30 mL). The organic layer was dried over $Na_2SO_4$, concentrated and chromatographed on silica (25% EtOAc/Hexane as eluent) to provide the title compound 108 (5.22 g, 88%) as a white crystalline solid. MS 260 (M+H).

t-Butyl 4-(1-Chloro-2-propenylidene)piperidine-1-carboxylate (109; Scheme XXIX) Methyltriphenylphosphonium bromide (5.51 g, 15.4 mmols) in THF (40 mL) at 0° C. was treated with sodium bis(trimethylsilyl)amide (15.4 mL, 1.0 M in THF) and stirred for 20 min whereupon compound 108 (2.05 g, 7.89 mmols) in THF (15 mL) was added via cannula and the mixture stirred for 3 hrs, warming to RT. The mixture was quenched by adding sat. aq. $NH_4Cl$ (20 mL) and the aqueous layer was extracted with EtOAc (6×20 mL). The combined organic layers were dried over $Na_2SO_4$, concentrated and chromatographed on silica (gradient elution with 0–10% $MeOH/CH_2Cl_2$) to provide the title compound 109 (1.94 g, 96%) as a white crystalline solid. MS 258 (M+H).

4-(1-Chloro-2-propenylidene)piperidine TFA salt (110; Scheme XXIX) To compound 109 (0.1415 g, 0.5489 mmol) in $CH_2Cl_2$ (5 mL) was added TFA (0.55 mL, 7.1 mmols) and the mixture stirred for 3 hrs whereupon all volatile materials were removed in vacuo. The crude title compound so obtained was used without further purification. MS 158 (M+H).

The protected amines listed in Table 7 were prepared in a similar fashion as described for t-butyl 4-[2-(1,3-dihydro-1,3-dioxo-2H-isoindol-2-yl)ethylidene]-piperidinyl-1-carboxylate (26), except the corresponding alcohol was used instead of t-butyl 4-(2-hydroxyethylidene)piperidinyl-1-carboxylate (25).

TABLE 7

| Alcohol | Protected Amine | Compound | (M + H) |
|---------|-----------------|----------|---------|
| 94 | | 111 | 401 |
| 96 | | 112 | 403 |
| 98 | | 113 | 397 |

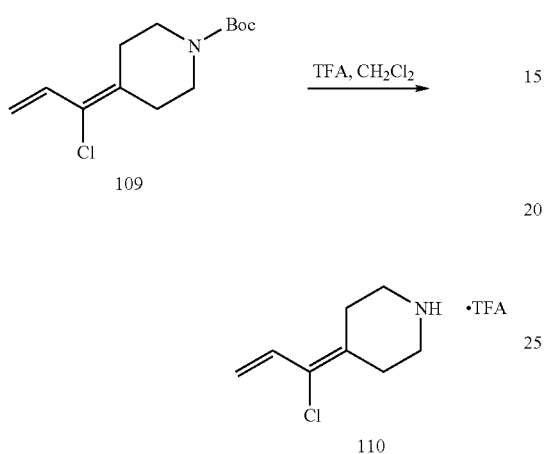

TABLE 7-continued

| Alcohol | Protected Amine | Compound | (M + H) |
|---|---|---|---|
| 100 | (structure) | 114 | 411 |
| 102 | (structure) | 115 | 426 |

The amines listed in Table 8 were prepared in a similar fashion as described for 4-[2-(1,3-dihydro-1,3-dioxo-2H-isoindol-2-yl)ethylidene]-1-piperidine trifluoroacetate (27), except the corresponding protected amine was used instead of t-butyl 4-[2-(1,3-dihydro-1.3-dioxo-2H-isoindol-2-yl) ethylidene]-piperidinyl-1-carboxylate (26).

TABLE 8

| Protected Amine | Amine | Compound | (M + H) |
|---|---|---|---|
| 111 | (structure) | 116 | 301 |
| 112 | (structure) | 117 | 303 |
| 113 | (structure) | 118 | 297 |
| 114 | (structure) | 119 | 311 |

Scheme XXX

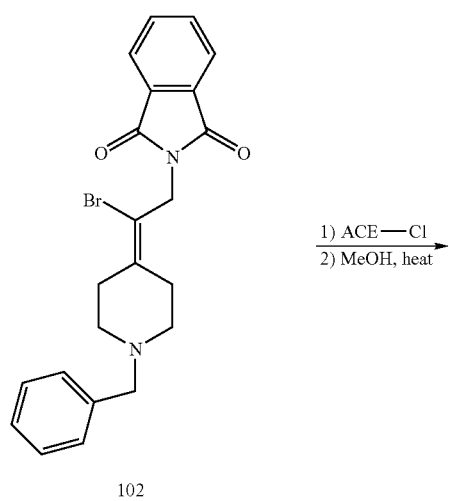

2-(2-Bromo-2-piperidin-4-ylidenylethyl)isoindole-1,3-dione hydrochloride (120: Scheme XXX). A mixture of 102 (0.50 g, 1.17 mmol) and 1-chloroethyl chloroformate (0.7 mL, 6.2 mmol) in dichloroethane (10 mL) was warmed to reflux temperature for 2 h. The resulting solution was allowed to cool to room temperature and concentrated in vacuo. The residue was dissolved in methanol (50 mL) and warmed to reflux temperature for 2 h. The reaction mixture was allowed to cool to room temperature and concentrated in vacuo to afford a white solid. The residue was washed with diethyl ether (2×) and dried to afford title compound (432 mg, 100%) as an orange oil. MS 336 (M+H).

Compounds Z-37 and E-37 of Scheme XV:

(E/Z)-Ethyl chloro(1-benzyl-3-pyrrolidinylidene)acetate (34). Prepared by the same procedure as in the synthesis of 24 except that 1-benzyl-pyrrolidin-3-one was used in place of 1-(tert-butoxycarbonyl)-4-piperidinone and triethyl 2-chlorophosphonoacetate was used in place of triethyl phosphonoacetate. MS 280 (M+H).

(E/Z)-2-(1-Benzyl-3-pyrrolidinylidene)-2-chloroethanol (35). Prepared by the same procedure as in the synthesis of 25 except that 34 was used in place of 24. MS 283 (M+H).

Scheme XV

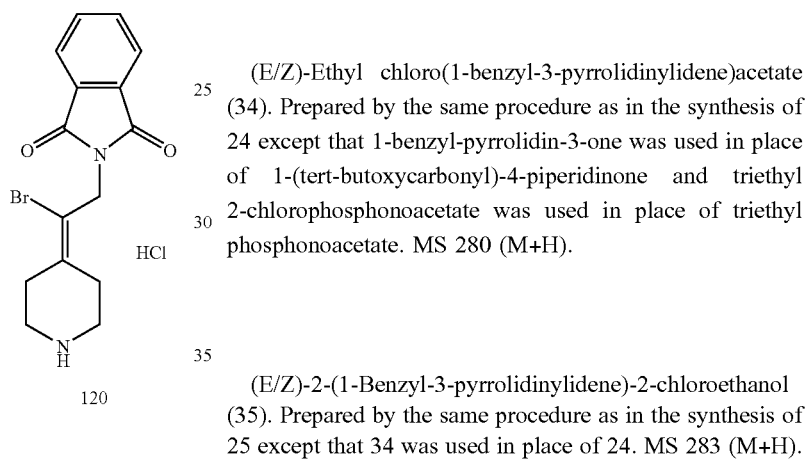

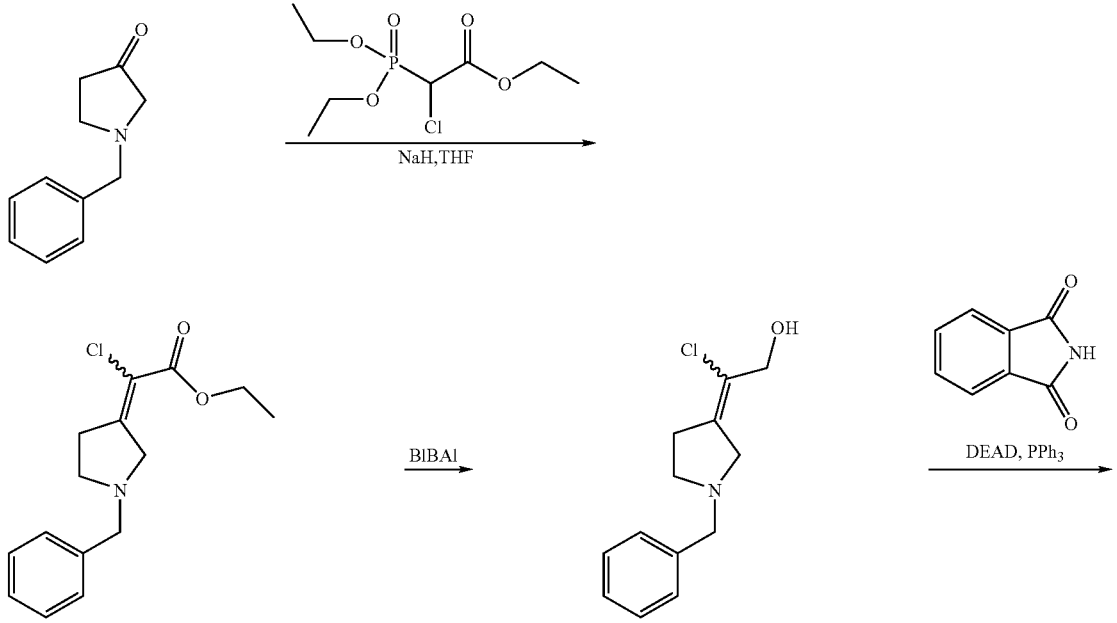

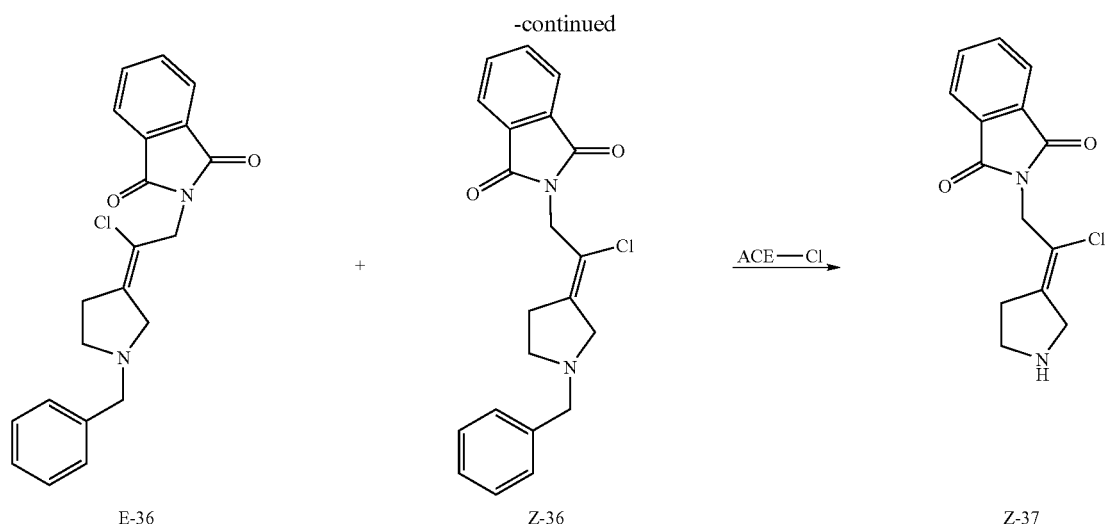

E-36          Z-36          Z-37

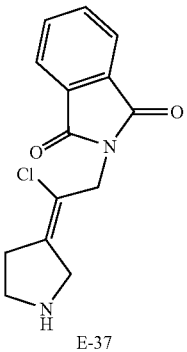

E-37

(E/Z)-2-[2-(1-Benzyl-3-pyrrolidinylidene)-2-chloroethyl]-1H-isoindole-1,3(2H)-dione (E-36 and Z-36). Prepared by the same procedure as in the synthesis of 26 except that 35 (1.58 g) was used in place of 25. The E/Z isomers were separated by MPLC (0–45% ethyl acetate/hexanes) to afford Z-36 (430 mg, MS 367 (M+H)) as a reddish oil and E-36 (420 mg, MS 367 (M+H)) as a reddish oil.

(E)-2-[2-Chloro-2-(3-pyrrolidinylidene)ethyl]-1H-isoindole-1,3(2H)-dione hydrochloride (E-37). A mixture of E-36 (0.430 g, 1.45 mmol) and 1-chloroethyl chloroformate (0.7 mL, 6.2 mmol) in dichloroethane (10 mL) was warmed to reflux temperature for 2 h. The resulting solution was allowed to cool to room temperature, and concentrated in vacuo. The residue was dissolved in methanol (50 mL) and warmed to reflux temperature for 2 h. The reaction mixture was allowed to cool to room temperature and concentrated in vacuo to afford a white solid. The residue was washed with diethyl ether (2×) and dried to afford E-37 (200 mg, 50%) as a brown oil. MS 277 (M+H).

(Z)-2-[2-Chloro-2-(3-pyrrolidinylidene)ethyl]-1H-isoindole-1,3(2H)-dione hydrochloride (Z-37). Prepared by the same procedure as in the synthesis of E-37 except that Z-36 was used in place of E-36. MS 277 (M+H).

Scheme XVI

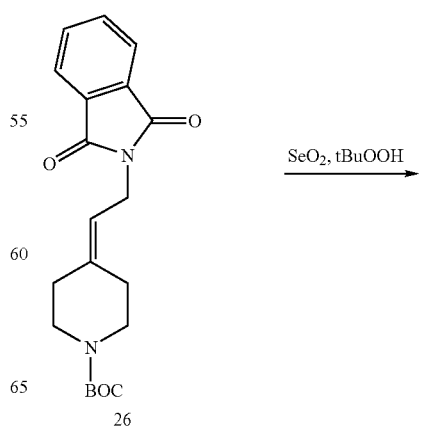

26

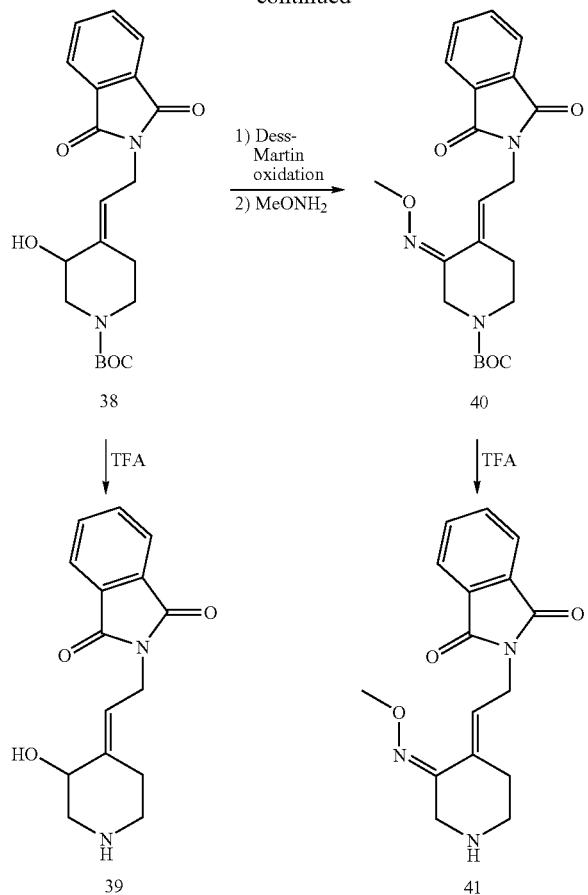

38 → 40

39 41

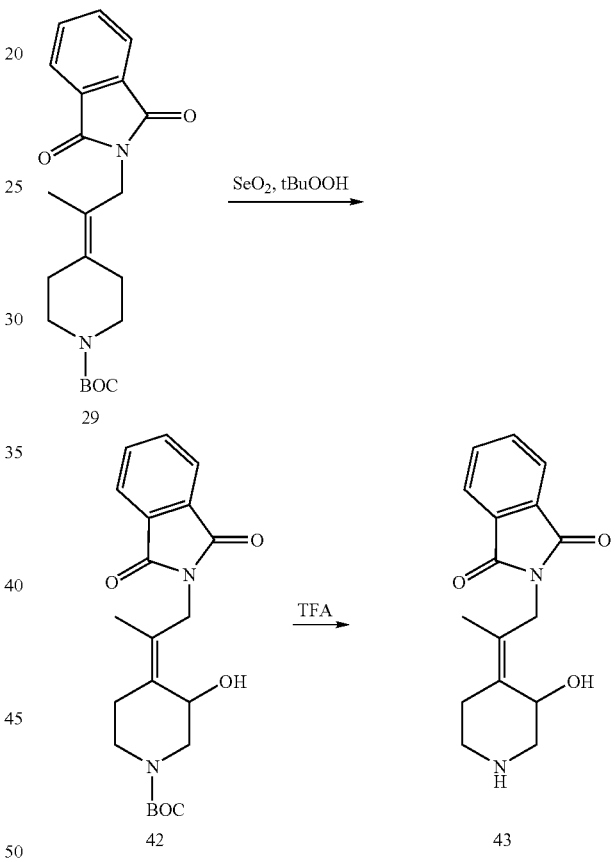

Scheme XVII

29

42 → 43 trated in vacuo. The residue was used in the next step without further purification. A solution of the residue in pyridine (6 mL) in methanol (36 mL) at 25° C. was treated with methoxyamine hydrochloride (0.835 g, 6.0 mmol). After 2 min, the reaction mixture was warmed to reflux for 5 h, diluted with ethyl acetate (25 mL), washed with 10% aqueous NaHCO$_3$ (3×25 mL), dried (MgSO$_4$), filtered and concentrated in vacuo to afford 40 (230 mg, 42%) as an orange residue. The residue was used in the next step without further purification. MS 400 (M+H).

(E)-4-[2-(1,3-dioxo-1,3-dihydro-2H-isoindol-2-yl)eth-ylidene]-3-methoxyimino-piperidine (41). Prepared by the same procedure as in the synthesis of 27 except that 40 was used in place of 26. MS 300 (M+H).

Compounds 39 and 41 of Scheme XVI:

t-Butyl (E)-4-[2-(1,3-dioxo-1,3-dihydro-2H-isoindol-2-yl)ethylidene]-3-hydroxy-piperidinyl-1-carboxylate (38). A slurry of SeO$_2$ (0.5 g, 6.06 mmol) in CH$_2$Cl$_2$ (5 mL) at 0° C. was treated with tert-butyl hydroperoxide (2.5 mL, 9.09 mmol, 5–6 M, 10% in undecane) via a syringe. After 20 min, the reaction mixture was treated with a solution of eth-ylidene 26 (1.44 g, 4.04 mmol) in CH$_2$Cl$_2$ (15 mL) and the resulting mixture was allowed to stir for 12 h at room temperature. The reaction was carefully quenched by the addition of 15% aqueous sodium thiosulfate (15 mL), and the reaction mixture was diluted with CH$_2$Cl$_2$ (25 mL). The layers are separated, and the organic layer was washed with 15% aqueous sodium thiosulfate (15 mL), dried (MgSO$_4$), filtered and concentrated in vacuo. Purification by flash chromatography (silica gel, 0–75% ethyl acetate/hexanes) afforded the title compound 38 (0.51 g, 33%) as a white solid. MS 373 (M+H).

(E)-4-[2-(1,3-dioxo-1,3-dihydro-2H-isoindol-2-yl)eth-ylidene]-3-hydroxypiperidine (39). Prepared by the same procedure as in the synthesis of 27 except that 38 was used in place of 26. MS 273 (M+H).

E)-t-Butyl 4-[2-(1,3-dioxo-1,3-dihydro-2H-isoindol-2-yl) ethylidene]-3-methoxyimino-piperidinyl-1-carboxylate (40). A solution of 38 (0.51 g, 1.37 mmol) in CH$_2$Cl$_2$ (15 mL) at 25° C. was treated with Dess-Martin periodinane (0.254 g, 0.60 mmol). After 1 h, the reaction mixture was diluted with CH$_2$Cl$_2$ (25 mL), washed with 10% aqueous NaHCO$_3$ (3×25 mL), dried (MgSO$_4$), filtered and concen- Compound 43 of Scheme XVII:

(Z)-t-Butyl 4-[2-(1,3-dioxo-1,3-dihydro-2H-isoindol-2-yl)-1-methylethylidene]-3-hydroxy-piperidinyl-1-carboxy-late (42). A slurry of SeO$_2$ (1.3 g, 11.4 mmol) in CH$_2$Cl$_2$ (15 mL) at 0° C. was treated with tert-butyl hydroperoxide (4 mL, 22 mmol, 5–6 M, 10% in undecane) via a syringe. After 20 min, the reaction mixture was treated with a solution of ethylidene 29 (3.4 g, 9.1 mmol) in CH$_2$Cl$_2$ (15 mL) and the resulting mixture was allowed to stir for 12 h at room temperature. The reaction was carefully quenched by the addition of 15% aqueous sodium thiosulfate (15 mL), and the reaction mixture was diluted with CH$_2$Cl$_2$ (25 mL). The layers were separated, and the organic layer was washed with 15% aqueous sodium thiosulfate (15 mL), dried (MgSO$_4$), filtered and concentrated in vacuo. Purification by flash chromatography (silica gel, 0–75% ethyl acetate/hexanes) afforded the title compound 42 (1.2 g, 34%) as a white solid. MS 387 (M+H).

(Z)-4-[2-(1,3-dioxo-1,3-dihydro-2H-isoindol-2-yl)1-methyl-ethylidene]-3-hydroxy-piperidine (43). Prepared by the same procedure as in the synthesis of 27 except that 42 was used in place of 26. MS 287 (M+H).

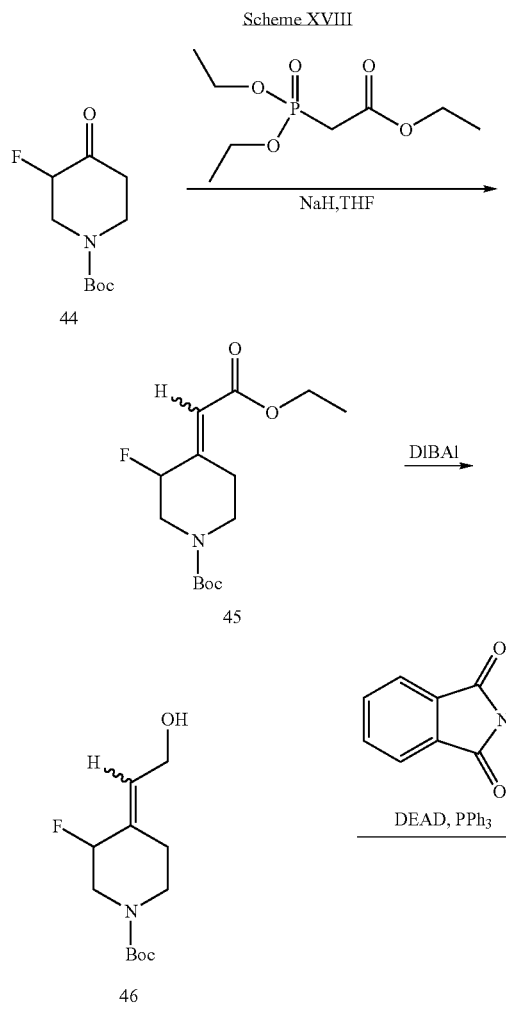

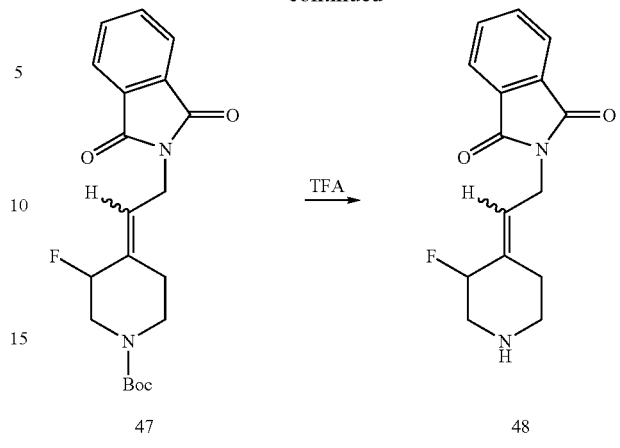

Compound 48 of Scheme XVIII:

t-Butyl-3-fluoro-4-oxopiperidinyl-1-carboxylate (44) was prepared according to U.S. Pat. No. 5,837,715.

(E/Z)-t-Butyl 4-(2-ethoxy-2-oxoethylidene)-3-fluoropiperidinyl-1-carboxylate (45) Prepared by the same procedure as in the synthesis of 24 except that 44 was used in place of 1-(tert-butoxycarbonyl)-4-piperidinone. MS 288 (M+H).

(E/Z)-t-Butyl 4-(2-hydroxyethylidene)-3-fluoropiperidinyl-1-carboxylate (46) Prepared by the same procedure as in the synthesis of 25 except that 45 was used in place of 24. MS 246 (M+H).

(E/Z)-t-Butyl 4-[2-(1,3-dihydro-1,3-dioxo-2H-isoindol-2-yl)ethylidene]-3-fluoro-piperidinyl-1-carboxylate (47) Prepared by the same procedure as in the synthesis of 26 except that 46 was used in place of 25. MS 375 (M+H).

(E/Z)-4-[2-(1,3-dihydro-1,3-dioxo-2H-isoindol-2-yl)ethylidene]-3-fluoropiperidine trifluoroacetate (48). Prepared by the same procedure as in the synthesis of 27 except 47 was used in place of 26. MS 275 (M+H).

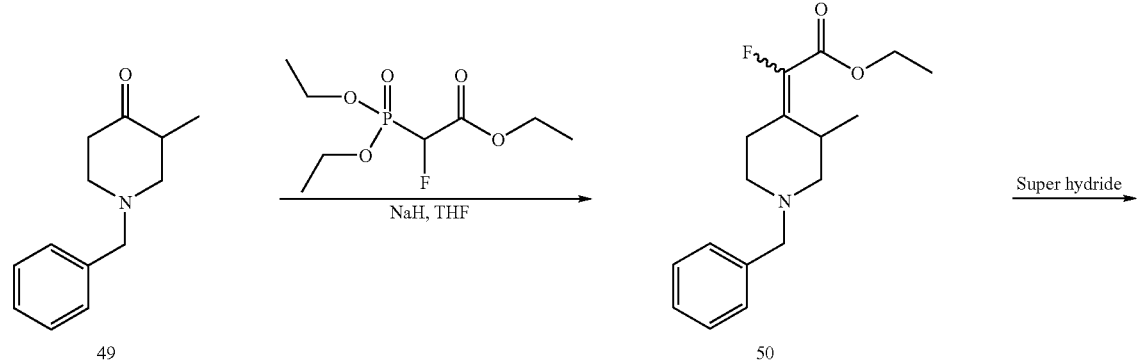

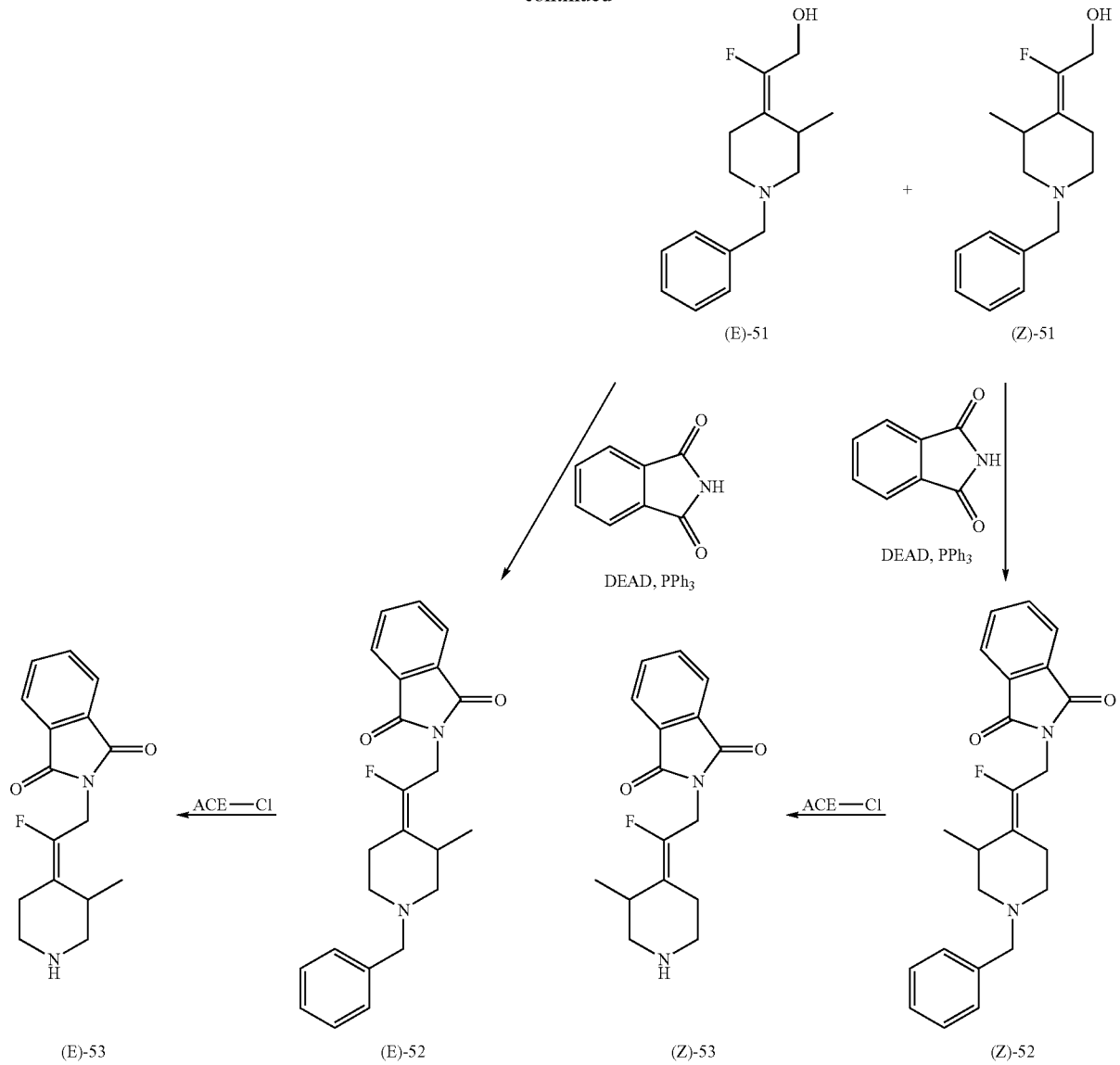

Compounds Z-53 and E-53 of Scheme XIX:

Ethyl 1-[3-methyl-1-(phenylmethyl)-4-piperidinylidenyl]-1-fluoroacetate (50). Prepared by the same procedure as in the synthesis of 24 except that 49 was used in place of 1-(tert-butoxycarbonyl)-4-piperidinone and triethyl 2-fluorophosphonoacetate was used in place of triethyl phosphonoacetate. MS 292 (M+H).

2-[3-methyl-1-(phenylmethyl)-4-piperidinylidenyl]-2-fluoroethanol (E-51 and Z-51). A solution of 50 (2.68 g, 9.19 mmol) in tetrahydrofuran (50 mL) at 0° C. was treated with a solution of Super-Hydride™ (23 mL, 23 mmol, 1.0 M in tetrahydrofuran, Aldrich) under nitrogen. After 1 h, the reaction mixture was carefully treated with methanol (10 mL), diluted with ethyl acetate (50 mL), washed with 10% aqueous NaHCO₃ (3×50 mL), dried (MgSO₄) and concentrated in vacuo. Purification by MPLC (silica gel, 0–50% ethyl acetate/hexanes) afforded the Z-isomer 51 (0.84 g, 37%) (MS 250 (M+H)) as a colorless oil and the E-isomer 51 (0.97 g, 42%) (MS 250 (M+H)) as a colorless oil.

(Z)-2-[2-(3-methyl-1-(Phenylmethyl)-4-piperidinylidenyl)-2-fluoroethyl]-1H-isoindole-1,3(2H)-dione (Z-52). Prepared by the same procedure as in the synthesis of 26 except that Z-51 was used in place of 25. MS 379 (M+H).

(E)-2-[2-(3-methyl-1-(phenylmethyl)-4-piperidinylidenyl)-2-fluoroethyl]-1H-isoindole-1,3(2H)-dione (E-52). Prepared by the same procedure as in the synthesis of 26 except that E-51 was used in place of 25. MS 379 (M+H).

(Z)-2-[2-fluoro-2-(3-methyl-4-piperidinylidenyl)-ethyl]-1H-isoindole-1,3(2H)-dione hydrochloride (Z-53). A mixture of Z-52 (0.550 g, 1.45 mmol) and 1-chloroethyl chloroformate (0.63 mL, 5.8 mmol) in dichloroethane (15 mL) was warmed to reflux temperature for 2 h. The resulting solution was allowed to cool to room temperature, and concentrated in vacuo. The residue was dissolved in methanol (50 mL) and warmed to reflux temperature for 2 h. The reaction mixture was allowed to cool to room temperature and concentrated in vacuo to afford a white solid. The residue was washed with diethyl ether (2×) and dried to afford Z-53 (260 mg, 55%) as a white solid. MS 289 (M+H).

(E)-2-[2-fluoro-2-(3-methyl-4-piperidinylidenyl)-ethyl]-1H-isoindole-1,3(2H)-dione hydrochloride (E-53). Prepared by the same procedure as in the synthesis of Z-52 except that E-52 was used in place of Z-52. MS 289 (M+H).

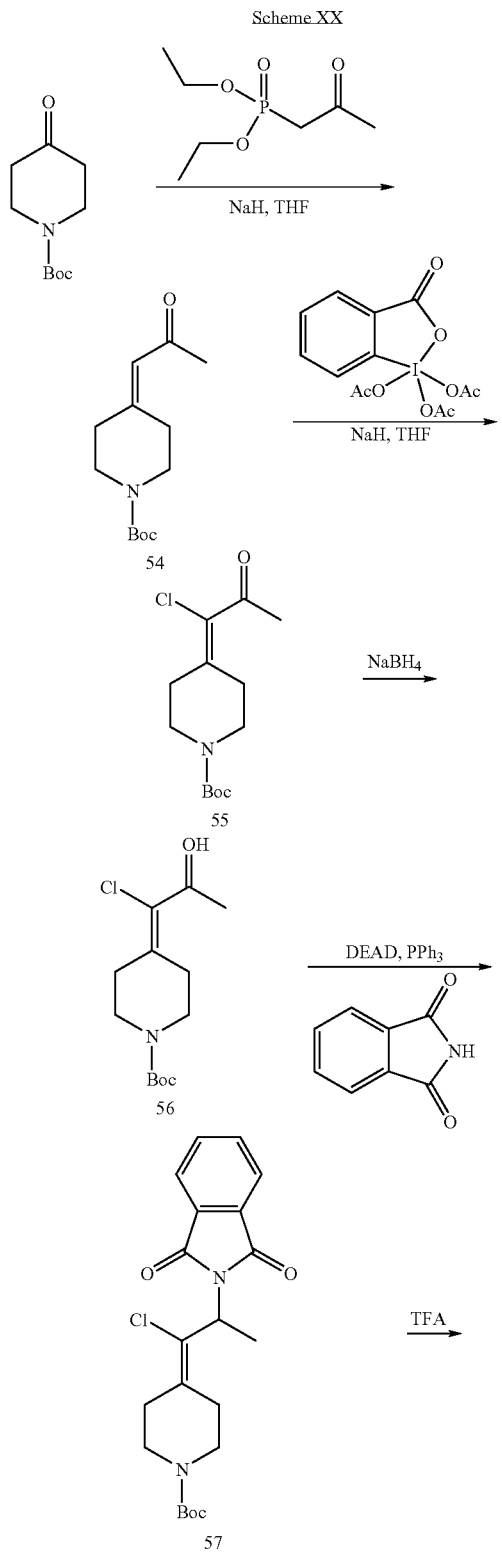

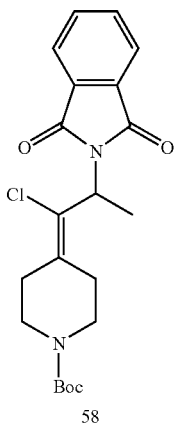

4-(2-Oxo-propylidene)piperidine-1-carboxylic acid tert-butyl ester (54). Prepared by the same procedure as described in International Patent Publication WO0285901.

4-(1-Chloro-2-oxo-propylidene)piperidine-1-carboxylic acid tert-butyl ester (55). A slurry of tetrabutylammonium chloride (11.1 g, 40.1 mmol) in $CH_2Cl_2$ (50 mL) at 25° C. was treated with 1,1,1-tris(acetyloxy)-1,1-dihydro-1,2-benziodoxol-3(1H)-one (17.0 g, 40.1 mmol) and the resulting light yellow solution was allowed to stir for 10 min. The reaction mixture was treated with a solution of 54 in $CH_2Cl_2$ (50 mL) and the resulting solution was allowed to stir for 3 h. The light yellow solution was carefully poured into a 10% aqueous solution of sodium bicarbonate (100 mL), diluted with $CH_2Cl_2$ (50 mL), to induce precipitation, filtered, and the precipitate was discarded. The resulting clear solution was washed with a 10% aqueous solution of sodium bicarbonate (1×100 mL), brine (1×100 mL), dried ($MgSO_4$), and concentrated in vacuo. Purification by MPLC (0–40% ethyl acetate/hexanes) afforded 55 (1.24 g, 34%) as a colorless oil. MS 274 (M+H).

4-(1-Chloro-2-hydroxypropylidene)piperidine-1-carboxylic Acid Tert-Butyl Ester (56)

A solution of 55 (1.24 g, 4.53 mmol) in ethanol (25 mL) was treated with sodium borohydride (102 mg, 2.72 mmol) at 25° C. After 1 h, the reaction mixture was concentrated in vacuo, diluted with ethyl acetate (40 mL), carefully treated with 5% aqueous hydrochloric acid (1×25 mL), the layers separated, and dried ($MgSO_4$). The resulting solution was concentrated in vacuo to afford 56 (902.1 mg, 72%) as a colorless residue that was used without further purification. MS 298 (M+Na).

4-[1-Chloro-2-(1,3-dioxo-1,3-dihydro-isoindol-2-yl)-propylidene]piperidine-1-carboxylic acid tert-butyl ester (57). Prepared by the same procedure as in the synthesis of 26 except that 56 was used in place of 25. MS 427 (M+Na).

2-[(2-Chloro-1-methyl-2-(4-piperidinylidene)ethyl]-1H-isoindole-1,3(2H)-dione (58) Prepared by the same procedure as in the synthesis of 27 except that 56 was used in place of 26. MS 305 (M+H).

Scheme XXXI

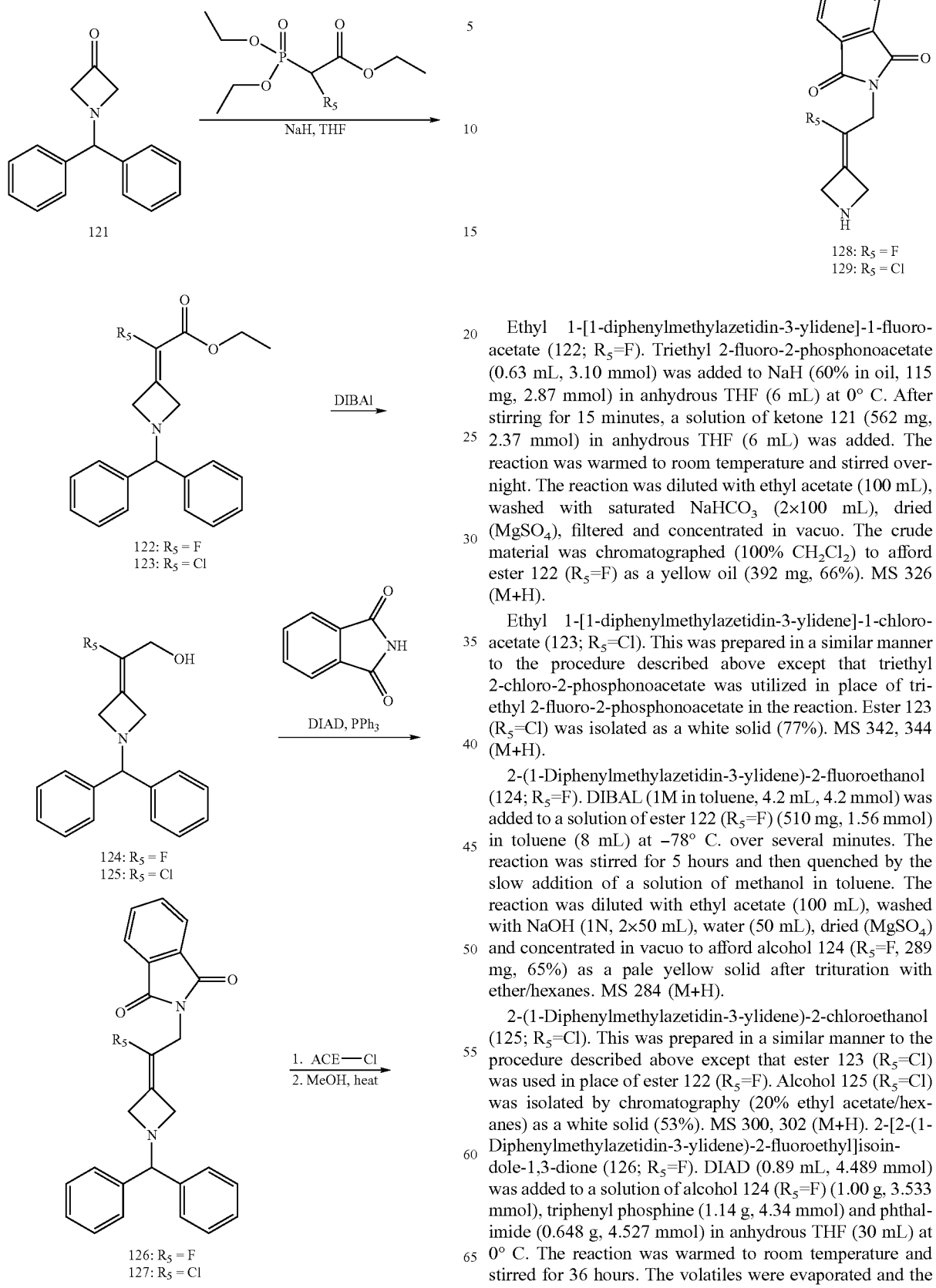

Ethyl 1-[1-diphenylmethylazetidin-3-ylidene]-1-fluoroacetate (122; R₅=F). Triethyl 2-fluoro-2-phosphonoacetate (0.63 mL, 3.10 mmol) was added to NaH (60% in oil, 115 mg, 2.87 mmol) in anhydrous THF (6 mL) at 0° C. After stirring for 15 minutes, a solution of ketone 121 (562 mg, 2.37 mmol) in anhydrous THF (6 mL) was added. The reaction was warmed to room temperature and stirred overnight. The reaction was diluted with ethyl acetate (100 mL), washed with saturated NaHCO₃ (2×100 mL), dried (MgSO₄), filtered and concentrated in vacuo. The crude material was chromatographed (100% CH₂Cl₂) to afford ester 122 (R₅=F) as a yellow oil (392 mg, 66%). MS 326 (M+H).

Ethyl 1-[1-diphenylmethylazetidin-3-ylidene]-1-chloroacetate (123; R₅=Cl). This was prepared in a similar manner to the procedure described above except that triethyl 2-chloro-2-phosphonoacetate was utilized in place of triethyl 2-fluoro-2-phosphonoacetate in the reaction. Ester 123 (R₅=Cl) was isolated as a white solid (77%). MS 342, 344 (M+H).

2-(1-Diphenylmethylazetidin-3-ylidene)-2-fluoroethanol (124; R₅=F). DIBAL (1M in toluene, 4.2 mL, 4.2 mmol) was added to a solution of ester 122 (R₅=F) (510 mg, 1.56 mmol) in toluene (8 mL) at −78° C. over several minutes. The reaction was stirred for 5 hours and then quenched by the slow addition of a solution of methanol in toluene. The reaction was diluted with ethyl acetate (100 mL), washed with NaOH (1N, 2×50 mL), water (50 mL), dried (MgSO₄) and concentrated in vacuo to afford alcohol 124 (R₅=F, 289 mg, 65%) as a pale yellow solid after trituration with ether/hexanes. MS 284 (M+H).

2-(1-Diphenylmethylazetidin-3-ylidene)-2-chloroethanol (125; R₅=Cl). This was prepared in a similar manner to the procedure described above except that ester 123 (R₅=Cl) was used in place of ester 122 (R₅=F). Alcohol 125 (R₅=Cl) was isolated by chromatography (20% ethyl acetate/hexanes) as a white solid (53%). MS 300, 302 (M+H). 2-[2-(1-Diphenylmethylazetidin-3-ylidene)-2-fluoroethyl]isoindole-1,3-dione (126; R₅=F). DIAD (0.89 mL, 4.489 mmol) was added to a solution of alcohol 124 (R₅=F) (1.00 g, 3.533 mmol), triphenyl phosphine (1.14 g, 4.34 mmol) and phthalimide (0.648 g, 4.527 mmol) in anhydrous THF (30 mL) at 0° C. The reaction was warmed to room temperature and stirred for 36 hours. The volatiles were evaporated and the residue chromatographed on silica gel (5% ethyl acetate/ hexanes) to afford phthalimide 126 ($R_5$=F) (952 mg, 65%) as a white solid. MS 413 (M+H).

2-[2-(1-Diphenylmethylazetidin-3-ylidene)-2-chloroethyl]isoindole-1,3-dione (127; $R_5$=Cl). This was prepared in a similar manner to the procedure described above except that alcohol 125 ($R_5$=Cl) was used in place of alcohol 124 ($R_5$=F) in the Mitsunobu reaction. Phthalimide 127 ($R_5$=Cl) was isolated by chromatography (15% ethyl acetate/hexanes) as a white solid (68%). MS 429, 431 (M+H).

2-(2-Azetidin-3-ylidene-2-fluoroethyl)isoindole-1,3-dione Hydrochloride (128; $R_5$=F). Phthalimide 126 ($R_5$=F) (350 mg, 0.8491 mmol) and ACE-Cl (0.50 mL, 4.65 mmol) in 1,2-dichloroethane (20 mL) were heated at reflux temperature under a nitrogen atmosphere for 24 hours. After cooling, the volatiles were evaporated and methanol (25 mL) was added to the resulting residue. This was heated at reflux temperature for 3 hours after which the methanol was evaporated to afford 128 ($R_5$=F) as a beige powder (230 mg, 96%). MS 247 (M+H).

2-(2-Azetidin-3-ylidene-2-chloroethyl)isoindole-1,3-dione Hydrochloride (129: $R_5$=Cl). This was prepared in a similar manner to the procedure described above except that phthalimide 127 ($R_5$=Cl) was used in place of phthalimide 126 ($R_5$=F) in the reaction. The compound was isolated as a white powder (86%). MS 263, 265 (M+H).

Scheme XXXII

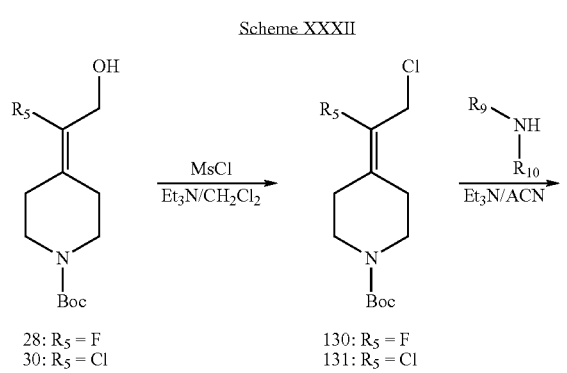

28: $R_5$ = F
30: $R_5$ = Cl

130: $R_5$ = F
131: $R_5$ = Cl

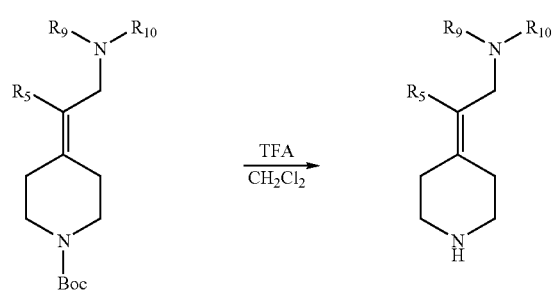

132; 144–147: $R_5$ = F
133; 136–143: $R_5$ = Cl

134; 156–159: $R_5$ = F
135; 148–155: $R_5$ = Cl

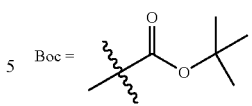

Boc = t-Butyl 4-(1,2-dichloroethylidene)piperidinyl-1-carboxylate (131; $R_5$=Cl). A solution of 30 ($R_5$=Cl) (4.24 g, 16.20 mmol)) and triethylamine (6.8 mL, 48.60 mmol) in $CH_2Cl_2$ (120 mL) was treated with methanesulfonyl chloride (1.9 mL, 24.30 mmol) at 0° C., then warmed to rt and stirred overnight. The resulting mixture was quenched by addition of saturated aq. $NaHCO_3$ (100 mL) and the product was extracted into $CH_2Cl_2$. Purification by flash chromatography (0–20% ethyl acetate/hexanes) afforded the title compound (3.1 g, 68%) as a white solid.

t-Butyl 4-(2-chloro-1-fluoroethylidene)piperidinyl-1-carboxylate (130; $R_5$=F). This was prepared in a similar manner to the procedure described above except that alcohol 28 ($R_5$=F) was used in place of alcohol 30 ($R_5$=Cl).

t-Butyl 4-[2-(N-benzyl-N-methylamino)-1-chloroethylidene]piperidinyl-1-carboxylate (133; $R_5$ Cl, $R_9$=Methyl: $R_{10}$=Benzyl).

A solution of 131 ($R_5$=Cl) (600 mg, 2.14 mmol)) and triethylamine (1.5 mL, 10.71 mmol) in acetonitrile (18 mL) was treated with N-benzylmethylamine (0.45 mL, 3.43 mmol) at rt and stirred overnight. The resulting mixture was concentrated in vacuo, and the residue was diluted with ethyl acetate (20 mL), washed with water (2×10 mL), and dried ($MgSO_4$). Purification by flash chromatography (0–15% ethyl acetate/hexanes) afforded the title compound (690 mg, 88%) as a white solid. MS 365 (M+H).

t-Butyl 4-[2-(N-benzyl-N-methylamino)-1-fluoroethylidene]piperidinyl-1-carboxylate (132; $R_5$=F: $R_9$=Methyl: $R_{10}$=Benzyl).

This was prepared in a similar manner to the procedure described above except that chloride 130 ($R_5$=F) was used in place of chloride 131 ($R_5$=Cl). MS 349 (M+H).

N-Benzyl-N-methyl-(2-chloro-2-piperidin-4-ylidene) ethylamine (135; $R_5$=Cl). A solution of 133 ($R_5$=Cl) (690 mg, 1.89 mmol) was dissolved in $CH_2Cl_2$ (15 mL) and was treated with trifluoroacetic acid (1.5 mL) at rt. After 5 h, the reaction mixture was concentrated in vacuo to afford the title compound (quant.) as an oil, which was used in the next step without further purification. MS 265 (M+H).

N-Benzyl-N-methyl-(2-fluoro-2-piperidin-4-ylidene) ethylamine (134; $R_5$=F). This was prepared in a similar manner to the procedure described above except that amine 132 ($R_5$=F) was used in place of amine 133 ($R_5$=Cl). MS 249 (M+H).

Table 9 lists the Boc-protected amines (136–147) and the derived amines (148–159) prepared by analogous procedures to those detailed above.

TABLE XX

| NHR₉R₁₀ | Cmpd. Number | Boc-protected Amine | (M + H) | Cmpd. Number | Amine | (M + H) |
|---|---|---|---|---|---|---|
| ethyl(benzyl)amine | 136 | (structure) | 379 | 148 | (structure) | 279 |
| dimethylamine | 137 | (structure) | 289 | 149 | (structure) | 189 |
| diethylamine | 138 | (structure) | 317 | 150 | (structure) | 217 |
| pyrrolidine | 139 | (structure) | 315 | 151 | (structure) | 215 |

TABLE XX-continued

| NHR$_9$R$_{10}$ | Cmpd. Number | Boc-protected Amine | (M + H) | Cmpd. Number | Amine | (M + H) |
|---|---|---|---|---|---|---|
| piperidine | 140 | (structure) | 329 | 152 | (structure) | 229 |
| morpholine | 141 | (structure) | 331 | 153 | (structure) | 231 |
| isopropylamine | 142 | (structure) | 303 | 154 | (structure) | 203 |
| N,N-dimethylethylenediamine | 143 | (structure) | 332 | 155 | (structure) | 232 |

TABLE XX-continued

| NHR₉R₁₀ | Cmpd. Number | Boc-protected Amine | (M + H) | Cmpd. Number | Amine | (M + H) |
|---|---|---|---|---|---|---|
| ethyl(benzyl)amine | 144 | Boc-piperidinylidene-fluoro-ethyl-N(ethyl)(benzyl) | 363 | 156 | piperidinylidene-fluoro-ethyl-N(ethyl)(benzyl) | 263 |
| N,N-dimethylamine | 145 | Boc-piperidinylidene-fluoro-ethyl-N(methyl)₂ | 373 | 157 | piperidinylidene-fluoro-ethyl-N(methyl)₂ | 273 |
| diethylamine | 146 | Boc-piperidinylidene-fluoro-ethyl-N(ethyl)₂ | 301 | 158 | piperidinylidene-fluoro-ethyl-N(ethyl)₂ | 201 |
| 1-benzylpiperazine | 147 | Boc-piperidinylidene-fluoro-ethyl-(4-benzylpiperazin-1-yl) | 404 | 159 | piperidinylidene-fluoro-ethyl-(4-benzylpiperazin-1-yl) | 304 |

Final Product Preparation

7-[4-(2-Amino-1-fluoro-ethylidene)piperidin-1-yl]-1-cyclopropyl-6-fluoro-4-oxo-1,4-dihydronaphthyridine-3-carboxylic acid (1) A solution of amine 31 (612 mg, 1.57 mmol) and triethylamine (0.7 mL, 5.0 mmol) in acetonitrile (4 mL) was treated with 7-chloro-1-cyclopropyl-6-fluoro-4-oxo-1, 4-dihydro-naphthpyridine-3-carboxylic acid (222 mg, 0.787 mmol) under nitrogen and the reaction mixture was allowed to stir for 12 h. The resulting mixture was concentrated in vacuo, and the residue was washed with water (3×10 mL). The residue was allowed to dry for 15 min. The solid was collected, resuspended in methanol (5 mL) and the reaction mixture was treated with hydrazine (1 mL). After 5 min, the reaction mixture was warmed to reflux and the resulting mixture was allowed to stir for 1 h. The reaction mixture was concentrated in vacuo, diluted with water and the solids were collected by filtration. The off white product was washed with water (3×20 mL), allowed to dry overnight to afford the title compound 1 (40.4 mg, 13%). MS 391 (M+H).

7-[4-(2-Amino-1-fluoro-ethylidene)piperidin-1-yl]-1-cyclopropyl-6-fluoro-4-oxo-1,4-dihydroquinoline-3-carboxylic acid trifluoroacetic acid salt (5) A solution of amine 31 (311 mg, 0.80 mmol) and triethylamine (0.55 mL, 4.0 mmol) in acetonitrile (4 mL) was treated with diacetyl quinolinyl borate 17 (300 mg, 0.60 mmol) under nitrogen. After 5 min, the reaction mixture was warmed to reflux and the reaction mixture was allowed to stir for 12 h. The resulting mixture was allowed to cool to room temperature, concentrated in vacuo, and the residue was washed with water (3×10 mL). The residue was dissolved in tetrahydrofuran (3 mL) and treated with 10% aqueous hydrochloric acid (5 mL) at room temperature. After 30 min, the reaction mixture was concentrated in vacuo, diluted with water (10 min) and the solid collected by filtration. The solid residue was washed with water (3×5 mL) and allowed to dry for 15 min. The solid was collected and resuspended in methanol (5 mL) and the reaction mixture was treated with hydrazine (1 mL). After 5 min, the reaction mixture was warmed to reflux temperature and the resulting mixture was allowed to stir for 1 h. The reaction mixture was concentrated in vacuo and the residue purified by HPLC (reverse phase C-18 column, 0–55% acetonitrile/water containing 0.1% trifluoroacetic acid) to afford the trifluoroacetic acid salt of 5 (61.3 mg, 20%) as a light yellow solid. MS 390 (M+H).

7-[3-(2-Amino-1-fluoro-ethylidene)azetidin-1-yl]-1-cyclopropyl-6-fluoro-4-oxo-1,4-dihydro-[1,8]naphthyridine-3-carboxylic acid (80). 7-Chloro-1-cyclopropyl-6-fluoro-4-oxo-1,4-dihydronaphthyridine-3-carboxylic acid (57 mg, 0.2016 mmol), amine 128 ($R_5$=F) (67 mg, 0.2389 mmol) and triethylamine (0.5 mL) in acetonitrile (10 mL) were heated at reflux temperature overnight. After cooling, the volatiles were evaporated and the residue suspended in water (25 mL). The resulting solid was collected by filtration and dried. Ethanol (5 mL) was added to the solid followed by hydrazine (0.01 mL, 0.3138 mmol). The reaction mixture was heated at reflux temperature for 1 hour after which the volatiles were evaporated. Water (15 mL) was added to the residue and the resulting solid collected by filtration, washed with additional water and dried to afford 87 (49.1 mg, 69%) as an off-white powder. MS 363 (M+H).

7-[3-(2-Amino-1-fluoro-ethylidene)azetidin-1-yl]-1-cyclopropyl-8-difluoromethoxy-6-fluoro-4-oxo-1,4-dihydroquinoline-3-carboxylic acid (160). A solution of amine 128 ($R_5$=F) (83 mg, 0.2923 mmol), diacetyl quinolinyl borate 83 (111 mg, 0.2413 mmol) and triethylamine (0.5 mL) in acetonitrile (10 mL) were heated at reflux temperature overnight. The volatiles were evaporated and then THF (5 mL) and 10% aqueous HCl (4 mL) were added to the residue. This mixture was stirred for approximately 1 hour. The resulting solid was collected by filtration, washed with water and dried. Ethanol (4 mL) and hydrazine (0.01 mL) were added to the solid and the reaction heated at reflux temperature for 1.5 hours. The ethanol was evaporated in vacuo and water (20 mL) added to the remaining material. The solid was collected and dried to afford 160 as a yellow solid (20%). MS 428 (M+H).

7-[4-[2-(N-Benzyl-N-methylamino)-1-chloroethylidene] piperidin-1-yl]-1-cyclopropyl-6-fluoro-8-methoxy-4-oxo-1, 4-dihydro-quinoline-3-carboxylic Acid Trifluoroacetic Acid Salt (161)

A solution of amine 135 (1.89 mmol) and triethylamine (1.2 mL, 8.59 mmol) in acetonitrile (15 mL) was treated with diacetyl quinolinyl borate 19 (727 mg, 1.72 mmol) under nitrogen. After 5 min, the reaction mixture was warmed to reflux temperature and the reaction mixture was allowed to stir for 24 h. The resulting mixture was allowed to cool to room temperature, and then concentrated in vacuo. The residue was dissolved in tetrahydrofuran (5 mL), treated with 10% aqueous hydrochloric acid (5 mL) at room temperature and stirred overnight. The resulting mixture was concentrated in vacuo and the residue purified by HPLC (reverse phase C-18 column, 30–90% acetonitrile/water containing 0.1% trifluoroacetic acid) to afford the trifluoroacetic acid salt of 161 (632 mg, 56%) as a yellow solid. MS 540 (M+H).

7-{4-[2-(N-Benzyl-N-methylamino)-1-chloroethylidene] piperidin-1-yl}-1-cyclopropyl-6-fluoro-4-oxo-1,4-dihydro-[1,8]naphthyridine-3-carboxylic Acid (162)

A solution of amine 135 (0.48 mmol) and triethylamine (0.28 mL, 2.0 mmol) in acetonitrile (7 mL) was treated with 7-chloro-1-cyclopropyl-6-fluoro-4-oxo-1,4-dihydro-[1,8] naphthyridine-3-carboxylic acid (113 mg, 0.40 mmol) under nitrogen. After 5 min, the reaction mixture was warmed to reflux temperature and the reaction mixture was allowed to stir for 24 h. The resulting mixture was allowed to cool to room temperature, concentrated in vacuo and the residue was diluted with water. The product was collected by filtration, and then washed with water and a small amount of methanol to afford the title compound (178 mg, 87%) as a white solid. MS 511 (M+H).

7-[4-(2-Hydroxyethylidene)piperidin-1-yl]-1-cyclopropyl-6-fluoro-4-oxo-1,4-dihydronaphthyridine-3-carboxylic acid (163) A solution of amine 103 (256 mg, 1.06 mmol) and triethylamine (0.5 mL, 3.55 mmol) in acetonitrile (4 mL) was treated with 7-chloro-1-cyclopropyl-6-fluoro-4-oxo-1, 4-dihydro-naphthyridine-3-carboxylic acid (200 mg, 0.71 mmol) under nitrogen and the reaction mixture was allowed to stir for 16 h. The resulting mixture was concentrated in vacuo, and the residue was washed with water (3×10 mL) and allowed to dry overnight to afford the title compound 163 (105 mg, 40%). MS 374 (M+H).

7-[4-(Hydroxyethylidene)piperidin-1-yl]-1-cyclopropyl-6-fluoro-4-oxo-1,4-dihydroquinoline-3-carboxylic acid (164) A solution of amine 103 (146 mg, 0.61 mmol) and triethylamine (0.55 mL, 4.0 mmol) in acetonitrile (4 mL) was treated with diacetyl quinolinyl borate 17 (125 mg, 0.60 mmol) under nitrogen. After 5 min, the reaction mixture was warmed to reflux temperature and the reaction mixture was allowed to stir for 12 h. The resulting mixture was allowed to cool to room temperature, concentrated in vacuo, and the residue was washed with water (3×10 mL). The residue was dissolved in tetrahydrofuran (3 mL) and treated with 10% aqueous hydrochloric acid (5 mL) at room temperature. After 30 min, the reaction mixture was concentrated in vacuo, diluted with water (10 min) and the solid collected by filtration. The solid residue was washed with water (3×5 mL) and allowed to dry for 15 min. The solid was collected to afford 157 (5.1 mg, 2.2%) as a light yellow solid. MS 373 (M+H).

Table 4 lists the additional compounds of the instant invention prepared by the experimental procedures detailed above. In the case of the naphthyridines 2–4, 59–63, 69, and 173–176 an analogous experimental procedure to that for compound 1 was used in their preparation. For the naphthyridines 171, 172, and 185, an analogous procedure to that for 163 was used. For the naphthyridines 81, 183 and 184, an analogous experimental procedure to that for 80 was used. For the naphthyridines 165–170, 177–182, and 186 a similar procedure to that for 162 was used in their preparation. For the quinolones 6–15, 64–66, 70, 71, 73, 78, 187, 188, 201–204, 206–208, and 210, an analogous experimental procedure to that for compound 5 was used in their preparation. For the quinolones 76, 77, 189, 205, and 209, an analogous procedure to that for 160 was used in their preparation. For the quinolones 190–200 an analogous procedure to that for 161 was used. For the quinolone 211 a similar procedure to that for 163 was used in its preparation.

TABLE 4

| Structure | Amine | Compound Number |
|---|---|---|
| Naphthyridine (cyclopropyl N-substituent) | 27 | 59 (M + H) = 373 |
| | 32 | 2 (M + H) = 387 |
| | 33 | 3 (M + H) = 407 |
| | 39 | 60 (M + H) = 389 |
| | 41 | 61 (M + H) = 416 |
| | 43 | 62 (M + H) = 403 |
| | 48 | 63 (M + H) = 391 |
| | 129 | 81 (M + H) = 379, 381 |
| | 148 | 165 (M + H) = 525 |
| | 154 | 166 (M + H) = 449 |
| | 134 | 167 (M + H) = 495 |
| | 156 | 168 (M + H) = 509 |
| | 158 | 169 (M + H) = 447 |
| | 159 | 170 (M + H) = 550 |
| | 105 | 171 (M + H) = 388 |
| | 104 | 172 (M + H) = 392 |
| | 85 | 69 (M + H) = 401 |
| | 118 | 173 (M + H) = 413 |
| | 119 | 174 (M + H) = 427 |
| | 117 | 175 (M + H) = 419 |
| | 120 | 176 (M + H) = 452 |
| | 155 | 177 (M + H) = 478 |
| | 110 | 178 (M + H) = 404 |
| | 107 | 179 (M + H) = 464 |
| | 149 | 180 (M + H) = 435 |
| | 152 | 181 (M + H) = 475 |
| | 157 | 182 (M + H) = 419 |
| Naphthyridine (2,4-difluorophenyl N-substituent) | 31 | 4 (M + H) = 463 |
| | 128 | 183 (M + H) = 435 |
| | 129 | 184 (M + H) = 451, 453 |
| | 103 | 185 (M + H) = 446 |
| | 157 | 186 (M + H) = 491 |
| Quinolone (cyclopropyl N-substituent) | 32 | 64 (M + H) = 386 |
| | 33 | 65 (M + H) = 406 |
| | 129 | 76 (M + H) = 378, 380 |
| | 135 | 187 (M + H) = 510 |
| | 134 | 188 (M + H) = 494 |

TABLE 4-continued

| Structure | Amine | Compound Number |
|---|---|---|
| [Quinolone structure with Amine, OMe, cyclopropyl substituents] | 31 | 6 (M + H) = 420 |
| | 33 | 7 (M + H) = 436 |
| | Z-53 | 11 (M + H) = 434 |
| | E-53 | 12 (M + H) = 434 |
| | Z-37 | 13 (M + H) = 422 |
| | E-37 | 14 (M + H) = 422 |
| | 58 | 15 (M + H) = 450 |
| | 129 | 189 (M + H) = 408, 410 |
| | 148 | 190 (M + H) = 554 |
| | 149 | 191 (M + H) = 464 |
| | 150 | 192 (M + H) = 492 |
| | 151 | 193 (M + H) = 490 |
| | 152 | 194 (M + H) = 504 |
| | 153 | 195 (M + H) = 506 |
| | 154 | 196 (M + H) = 478 |
| | 134 | 197 (M + H) = 524 |
| | 156 | 198 (M + H) = 538 |
| | 157 | 199 (M + H) = 448 |
| | 158 | 200 (M + H) = 476 |
| | 32 | 70 (M + H) = 402 |
| | 85 | 71 (M + H) = 430 |
| | 116 | 201 (M + H) = 446 |
| | 119 | 202 (M + H) = 456 |
| | 118 | 203 (M + H) = 442 |
| | 117 | 78 (M + H) = 448 |
| | 120 | 204 (M + H) = 481 |
| | 27 | 212 (M + H) = 402 |
| [Quinolone structure with F, Amine, OCF2H, cyclopropyl] | 129 | 205 (M + H) = 444, 446 |
| | 135 | 106 (M + H) = 576 |
| | 134 | 207 (M + H) = 560 |
| | 31 | 208 (M + H) = 456 |
| | 33 | 73 (M + H) = 472 |
| [Quinolone structure with Amine, OMe, cyclopropyl] | 31 | 10 (M + H) = 402 |
| | 129 | 209 (M + H) = 390, 392 |
| [Tricyclic structure with F, Amine, O, methyl] | 31 | 8 (M + H) = 406 |
| | 32 | 9 (M + H) = 402 |
| | 43 | 66 (M + H) = 416 |
| | 129 | 77 (M + H) = 394, 396 |
| | 39 | 210 (M + H) = 404 |
| | 105 | 211 (M + H) = 427 |

7-[4-(1-Chloro-2-methylaminoethylidene)piperidin-1-yl]-1-cyclopropyl-6-fluoro-8-methoxy-4-oxo-1,4-dihydroquinoline-3-carboxylic Acid Trifluoroacetic Acid Salt (72)

A solution of 154 (160 mg, 0.24 mmol) was dissolved in 1,2-dichloroethane (4 mL) and was treated with 1-chloroethyl chloroformate (0.8 mL, 7.3 mmol) under nitrogen. After 5 min, the reaction mixture was warmed to reflux temperature and the reaction mixture was allowed to stir for 3 h. The resulting mixture was allowed to cool to room temperature, and then it was concentrated in vacuo. The residue was dissolved in tetrahydrofuran (5 mL), adjusted to pH>7 by the addition of $NaHCO_3$ and water at room temperature and stirred overnight. The resulting mixture was concentrated in vacuo and the residue purified by HPLC (reverse phase C-18 column, 35–90% acetonitrile/water containing 0.1% trifluoroacetic acid) to afford the trifluoroacetic acid salt of 72 (37 mg, 27%) as a yellow solid. MS 450 (M+H).

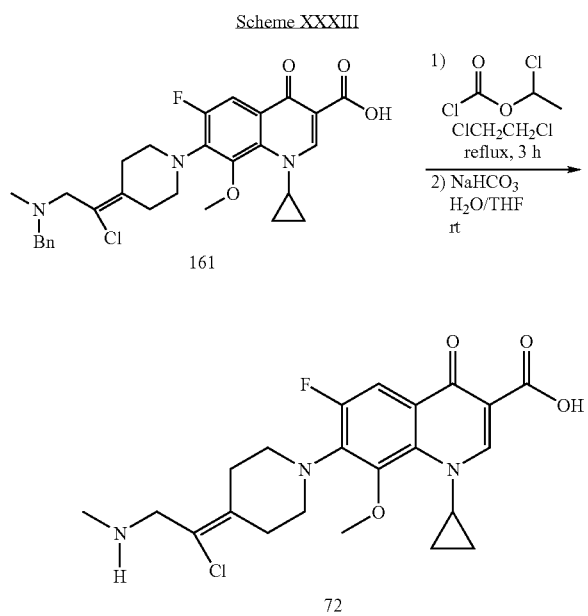

Scheme XXXIII

Table 10 lists the final products (74, 75, 79, 213–220) prepared by an analogous procedure to that above.

TABLE 10

| Structure | $R_5$ | $R_9$ | Compound Number | (M + H) |
|---|---|---|---|---|
| (quinoline with 8-OMe) | Cl | Et | 75 | 464 |
|  | F | Me | 213 | 434 |
|  | F | Et | 214 | 448 |
| (naphthyridine) | Cl | Me | 215 | 421 |
|  | Cl | Et | 216 | 435 |
|  | F | Me | 79 | 405 |
|  | F | Et | 217 | 419 |
| (quinoline, no 8-substituent) | Cl | Me | 218 | 420 |
|  | F | Me | 219 | 404 |

TABLE 10-continued

| Structure | $R_5$ | $R_9$ | Compound Number | (M + H) |
|---|---|---|---|---|
| 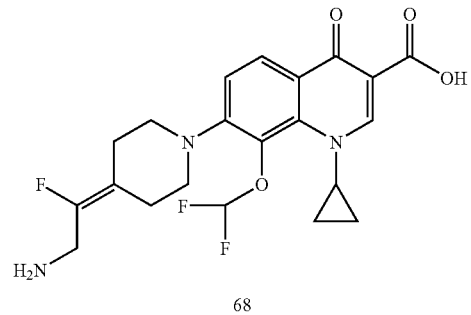 | Cl | Me | 74 | 486 |
| | F | Me | 220 | 470 |

Scheme XXXIV

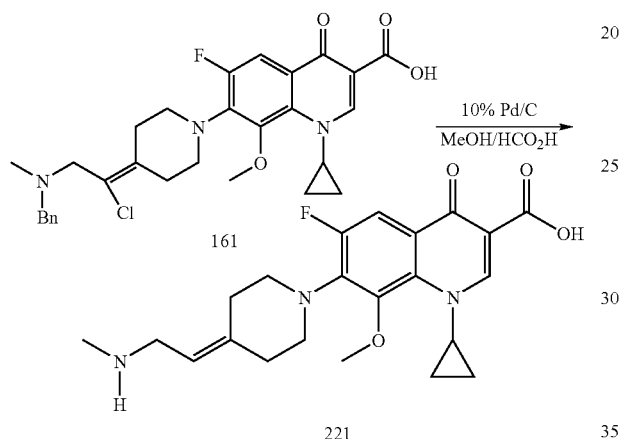

1-Cyclopropyl-6-fluoro-8-methoxy-7-[4-(2-methylaminoethylidene)piperidin-1-yl]-4-oxo-1,4-dihydroquinoline-3-carboxylic acid trifluoroacetic acid salt (221). A solution of 161 (70 mg, 0.11 mmol) in methanol/formic acid (v/v=20/1) (14 mL) was treated with 10% Pd/C (35 mg, 7.3 mmol) under nitrogen at rt and stirred for 3 h. The resulting mixture was filtered and concentrated in vacuo. The residue was purified by HPLC (reverse phase C-18 column, 35–90% acetonitrile/water containing 0.1% trifluoroacetic acid) to afford the trifluoroacetic acid salt of 221 (8.3 mg, 15%) as a yellow solid. MS 416 (M+H).

Scheme XXI

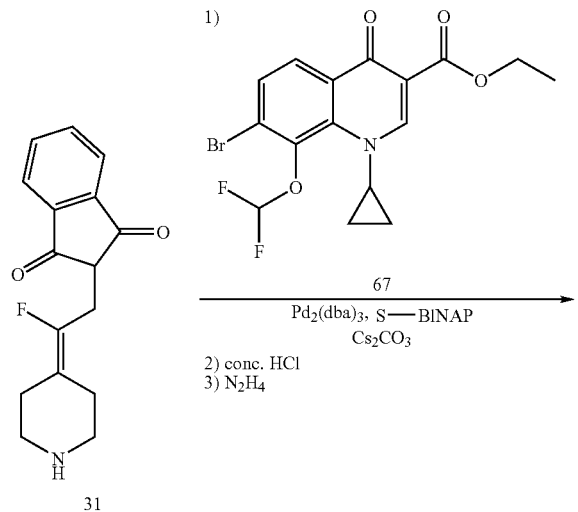

7-[4-(2-Amino-1-fluoroethylidene)-piperidin-1-yl]-1-cyclopropyl-8-difluoromethoxy-4-oxo-1,4-dihydro-quinoline-3-carboxylic acid (68). A solution of amine 31 (534 mg, 1.94 mmol) quinolone 67 (587 mg, 1.46 mmol) (prepared as described in EP1031569), cesium carbonate (717 mg, 2.2 mmol), (1S)-[1,1'-binaphthalene]-2,2'-diylbis[diphenylphosphine] (137 mg, 0.22 mmol) in toluene (75 mL) was treated with $Pd_2(dba)_3$ (66 mg, 0.072 mmol) and the reaction mixture was warmed to reflux. After 12 h, the resulting mixture was allowed to cool to room temperature, concentrated in vacuo, and the residue was washed with water (3×10 mL). Purification by MPLC (0–100% ethyl acetate/hexanes) afforded a yellow residue. The residue was dissolved in concentrated hydrochloric acid (5 mL) and warmed to reflux. After 3 h, the reaction mixture was concentrated in vacuo, diluted with water (10 min) and the solid collected by filtration. The solid residue was washed with water (3×5 mL) and allowed to dry for 15 min. The solid was collected and resuspended in methanol (5 mL) and the reaction mixture was treated with hydrazine (1 mL). After 5 min, the reaction mixture was warmed to reflux and the resulting mixture was allowed to stir for 1 h. The reaction mixture was concentrated in vacuo and purified by HPLC (reverse phase C-18 column, 0–55% acetonitrile/water containing 0.1% trifluoroacetic acid) to afford the trifluoroacetic acid salt of the title compound 68 (75 mg, 12%) as a light yellow solid. MS 438 (M+H).

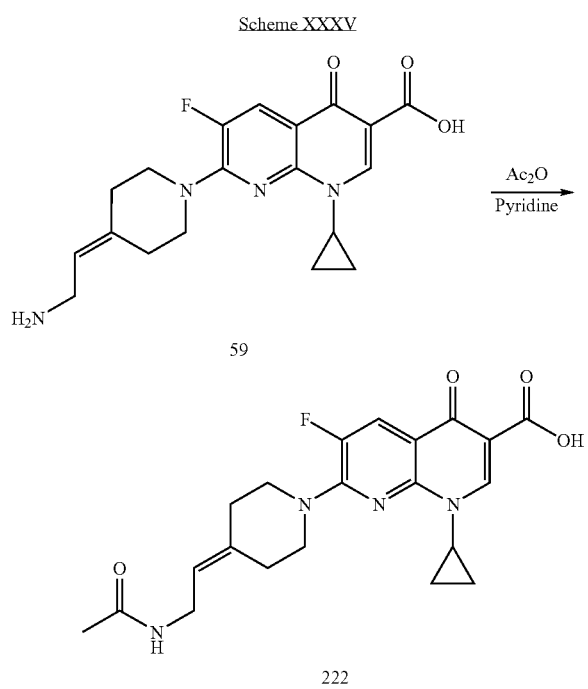

Scheme XXXV

59

222

7-[4-(2-Acetylamino-ethylidene)-piperidin-1-yl]-1-cyclopropyl-6-fluoro-4-oxo-1,4-dihydro-[1,8]naphthyridine-3-carboxylic acid (222). A mixture of 59 (25 mg, 0.067 mmol) and acetic anhydride (94 μL, 0.100 mmol) in pyridine (1 mL) was allowed to stir for 12 h at 25° C. The resulting mixture was concentrated in vacuo, and the residue was washed with water (3×10 mL) and allowed to dry overnight to afford the title compound 222 (15 mg, 54%). MS 415 (M+H).

Biological Activity

The compounds described in the present invention possess antibacterial activity due to their novel structure, and are useful as antibacterial agents for the treatment of bacterial infections in humans and animals.

Minimal inhibitory concentration (MIC) has been an indicator of in vitro antibacterial activity widely used in the art. The in vitro antimicrobial activity of the compounds was determined by the microdilution broth method following the test method from the National Committee for Clinical Laboratory Standards (NCCLS). This method is described in the NCCLS Document M7-A4, Vol.17, No.2, "Methods for Dilution Antimicrobial Susceptibility Test for Bacteria that Grow Aerobically—Fourth Edition", which is incorporated herein by reference.

In this method two-fold serial dilutions of drug in cation adjusted Mueller-Hinton broth are added to wells in microdilution trays. The test organisms are prepared by adjusting the turbidity of actively growing broth cultures so that the final concentration of test organism after it is added to the wells is approximately $5 \times 10^4$ CFU/well.

Following inoculation of the microdilution trays, the trays are incubated at 35° C. for 16–20 hours and then read. The MIC is the lowest concentration of test compound that completely inhibits growth of the test organism. The amount of growth in the wells containing the test compound is compared with the amount of growth in the growth-control wells (no test compound) used in each tray. As set forth in Table 5, compounds of the present invention were tested against a variety of pathogenic bacteria resulting in a range of activities depending on the organism tested.

TABLE 5

MIC Values (μg/mL) of Some Compounds of the Present Invention
(A: *Staphylococcus aureus* OC4172; strains B, C, and D are fluoroquinolone-resistant clinical isolates of *Streptococcus pneumnoniae* that contain different constellations of amino acid substitutions in the QRDR region; E: *Streptococcus pneumoniae* ATCC 49619)

| Compound/Organism | MIC (μg/mL) | | | | |
|---|---|---|---|---|---|
| | A | B | C | D | E |
| 1 | 0.03 | 2 | 0.5 | 1 | 0.12 |
| 2 | 0.06 | 0.25 | 1 | 1 | 0.12 |
| 3 | 0.06 | 1 | 0.25 | 1 | 0.12 |
| 4 | 0.06 | ND* | 1 | 2 | 0.25 |
| 5 | 0.03 | ND | 1 | ND | 0.06 |
| 6 | 0.03 | ND | 0.5 | ND | 0.06 |
| 7 | 0.015 | 0.06 | 0.12 | 0.12 | 0.06 |
| 8 | 0.25 | 2 | 8 | 8 | 0.5 |
| 9 | 0.5 | 4 | >16 | >16 | 1 |
| 10 | 0.03 | ND | 0.5 | 1 | 0.12 |
| 11 | 0.03 | ND | 0.5 | 1 | 0.12 |
| 12 | 0.12 | 2 | 4 | 4 | 0.5 |
| 189 | <0.12 | 4 | 2 | 4 | 2 |
| 76 | 0.03 | 2 | 1 | 2 | 0.25 |
| 77 | 0.12 | 8 | 16 | 16 | 1 |
| 80 | 0.06 | 0.5 | 2 | 1 | 0.12 |
| 205 | 0.25 | 2 | 8 | 4 | 0.5 |
| 81 | 0.06 | 1 | 2 | 2 | 0.25 |
| 160 | 0.06 | 2 | 2 | 1 | 0.12 |
| 183 | 0.12 | ND | 2 | 2 | 0.25 |
| 182 | 0.06 | ND | 1 | 2 | 0.25 |
| 209 | 0.12 | ND | 8 | 16 | 2 |
| 166 | 0.5 | ND | 4 | 4 | 1 |
| 191 | 0.25 | 8 | 8 | 2 | 0.5 |
| 193 | 0.12 | 8 | 8 | 2 | 0.5 |
| 194 | 0.12 | 2 | 4 | 1 | 0.5 |
| 195 | 0.12 | 8 | 8 | 2 | 1 |
| 196 | 0.12 | ND | 4 | 2 | 0.5 |
| 199 | 0.06 | 1 | 2 | 1 | 0.25 |
| 206 | 1 | ND | 4 | 4 | 4 |
| 207 | 1 | 8 | 8 | 2 | 4 |
| 72 | 0.03 | 0.25 | 0.5 | 0.25 | 0.12 |
| 75 | 0.12 | 1 | 1 | 1 | 0.25 |
| 213 | 0.12 | ND | 2 | 2 | 0.5 |
| 214 | 0.06 | ND | 1 | 1 | 0.25 |
| 215 | 0.25 | 2 | 2 | 2 | 0.25 |
| 216 | 0.06 | 0.12 | 2 | 1 | 0.25 |
| 79 | 0.06 | ND | 2 | 1 | 0.25 |
| 217 | 0.25 | ND | 2 | 2 | 0.25 |
| 218 | 0.12 | ND | 2 | 2 | 0.25 |
| 219 | 0.5 | 8 | 8 | 4 | 0.5 |
| 74 | 0.06 | ND | 1 | 0.25 | 0.12 |
| 220 | 0.12 | 2 | 4 | 0.5 | 0.5 |
| 221 | 0.12 | 2 | 4 | 4 | 0.5 |
| 201 | 0.12 | ND | 2 | 8 | 0.5 |
| 208 | 0.06 | 0.25 | 2 | 0.25 | 0.25 |
| 73 | 0.06 | 0.5 | 1 | 0.25 | 0.12 |
| 202 | 0.5 | 16 | 16 | 8 | 2 |
| 173 | 0.5 | 8 | 16 | 8 | 1 |
| 70 | 0.03 | ND | 0.25 | 0.25 | 0.12 |
| 69 | 0.06 | ND | 1 | 2 | 0.25 |
| 71 | 0.03 | ND | 0.25 | 0.5 | 0.12 |
| 65 | 0.03 | ND | 0.5 | 1 | 0.12 |
| 14 | 0.03 | 2 | 1 | 1 | 0.25 |
| 64 | 0.12 | 8 | 2 | 8 | 1 |
| 163 | 0.12 | 4 | 4 | ND | 1 |
| 185 | 0.12 | 16 | 16 | ND | 1 |
| 59 | 0.06 | 8 | 8 | ND | 0.5 |
| 164 | 0.12 | 32 | >32 | ND | 2 |
| 172 | 0.06 | 32 | 16 | ND | 1 |
| 211 | 0.03 | 4 | 4 | ND | 0.5 |
| 60 | 2 | ND | 16 | ND | 16 |
| 61 | 0.12 | ND | 16 | ND | 1 |

TABLE 5-continued

MIC Values (μg/mL) of Some Compounds of the Present Invention
(A: *Staphylococcus aureus* OC4172; strains B, C, and D are fluoroquinolone-resistant clinical isolates of *Streptococcus pneumnoniae* that contain different constellations of amino acid substitutions in the QRDR region; E: *Streptococcus pneumoniae* ATCC 49619)

| Compound/Organism | MIC (μg/mL) | | | | |
|---|---|---|---|---|---|
| | A | B | C | D | E |
| 210 | 8 | 16 | 16 | ND | >16 |
| 62 | 2 | >16 | >16 | ND | 8 |
| 204 | 0.25 | 0.5 | 0.5 | 0.5 | 0.12 |
| 176 | 0.25 | 0.5 | 1 | 1 | 0.12 |
| 175 | 0.5 | 2 | 2 | 1 | 0.25 |
| 78 | 1 | 2 | 1 | ND | 0.25 |
| 173 | 0.06 | 1 | 2 | 2 | 0.25 |
| 203 | 0.06 | 0.06 | 1 | 0.5 | 0.12 |
| 212 | 0.06 | 1 | 2 | 2 | 0.12 |
| 177 | 1 | 8 | >16 | >16 | 4 |
| 178 | 0.5 | 1 | 8 | 4 | 4 |
| 179 | 0.5 | >16 | >16 | >16 | 2 |
| 180 | 0.5 | ND | 8 | 2 | 0.5 |
| 181 | 1 | ND | >16 | 8 | 2 |

*ND = not determined

What is claimed is:

1. A compound having a structure according to Formula I

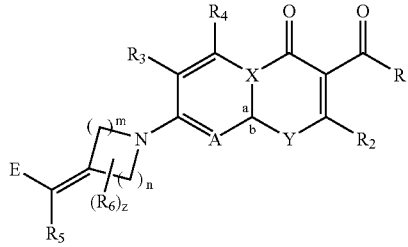

Formula I wherein:
n is an integer from 1 to 3;
m is an integer from 1 to 3;
z is an integer from 0 to 3;
R is selected from hydrogen, hydroxy, and alkoxy;
$R_2$ is hydrogen;
$R_3$ and $R_4$ are independently selected from hydrogen, halogen, amino, hydroxy, alkoxy, alkylthio, alkyl, alkenyl and alkynyl;
$R_5$ is selected from hydrogen, hydroxy, halogen, alkyl, aryl, alkoxy, and alkylthio;
$R_6$ is independently selected from alkyl, hydroxy, alkoxy, alkylthio, alkenyl, alkynyl, aryl, alkoxyimino, and halogen; or $R_5$ and $R_6$ join to form a 4- to 7-membered carbocyclic ring wherein each carbon atom of the ring can be optionally substituted with $R_{12}$, wherein $R_{12}$ is selected from the group consisting of halogen, amino, hydroxy, alkoxy, alkylthio, alkyl, alkenyl, alkynyl, oxo, alkoxyimino and hydroxyimino;

E is selected from the group consisting of:

1) 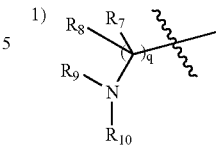

wherein,
q is an integer from 1 to 3;
$R_7$ and $R_8$ are each independently selected from hydrogen and alkyl, or $R_7$ and $R_8$ join to form a 3 to 6 membered carbocyclic ring, or either of $R_7$ or $R_8$ can be joined independently to either of $R_9$ or $R_{10}$ to form a heterocyclic ring containing the nitrogen atom to which $R_9$ or $R_{10}$ are bonded, wherein
$R_9$ and $R_{10}$ are each independently selected from hydrogen, alkyl, acyl, alkoxycarbonyl, or sulfonyl, or alternatively $R_9$ and $R_{10}$ join to form a heterocyclic ring containing the nitrogen atom to which they are bonded;

2) 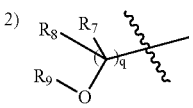

wherein,
q is as defined above;
$R_7$ and $R_8$ are each independenly selected from hydrogen and alkyl, or $R_7$ and $R_8$ join to form a 3- to 6-membered carbocyclic ring, and $R_9$ is selected from hydrogen, alkyl, acyl, alkoxycarbonyl, or sulfonyl; and 3) alkenyl;

A is selected from N and C ($R_{11}$), wherein $R_{11}$ is selected from hydrogen, alkyl, halogen, hydroxy, alkoxy, alkylthio, and cyano;

X is selected from C and N, where if X is C, a is a double bond and b is a single bond, and if X is N, a is a single bond and b is a double bond; and Y is selected from N($R_1$) and C($R_1$), with the proviso that when Y is N($R_1$), X is C and when Y is C($R_1$), X is N, wherein $R_1$ is selected from C3 to C6 cycloalkyl, C4 to C6 heterocycloalkyl, alkyl, alkene, a 6-membered aryl and a 6-membered heteroaryl; provided that if A is C($R_{11}$), X is C and Y is N($R_1$), then $R_{11}$ and $R_1$ can join to form a 6-membered heterocyclic ring, or if A is C($R_{11}$), X is C and Y is N($R_1$), then $R_2$ and $R_1$ can join to form a monocyclic or bicyclic heterocyclic ring, or if A is C($R_{11}$), X is C and Y is N($R_1$), then $R_2$ and R can join to form a 5-membered heterocyclic ring,;

or an optical isomer, diastereomer or enantiomer thereof; a pharmaceutically acceptable salt, hydrate, or prodrug thereof.

2. The compound of claim 1, wherein A is C(OCH$_3$), C(OCHF$_2$), or N.

3. The compound of claim 1, wherein Y is N($R_1$) and $R_1$ is selected from C3 to C6 cycloalkyl.

4. The compound of claim 1, wherein E is

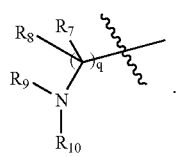

5. The compound of claim 1, wherein m is 1 and n is 1 or m is 2 and n is 2.

6. The compound of claim 1, wherein z is 0 or $R_6$ is methyl and z is 1.

7. The compound of claim 4, wherein $R_7$ and $R_8$ are hydrogen.

8. The compound of claim 7, wherein q is 1.

9. The compound of claim 8, wherein $R_9$ is hydrogen, methyl, or ethyl and $R_{10}$ is hydrogen.

10. A compound of claim 1 selected from the group consisting of:

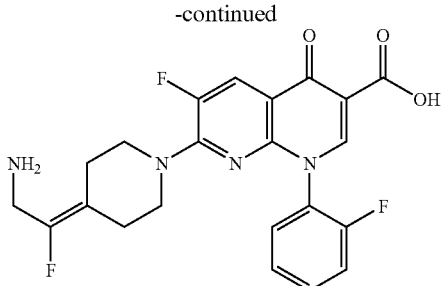

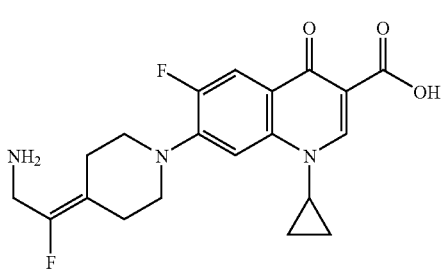

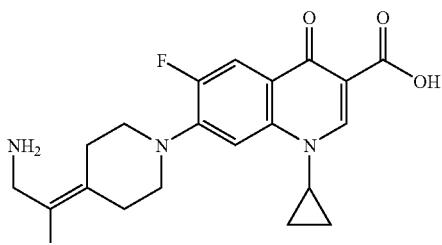

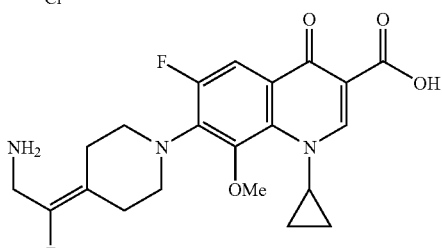

-continued

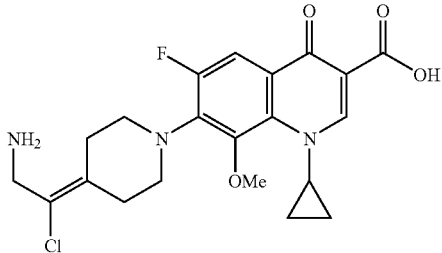

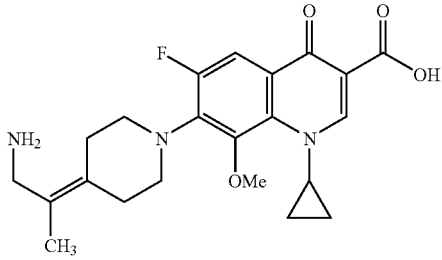

-continued
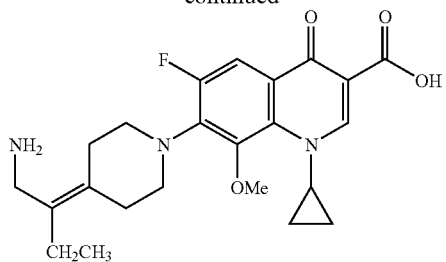
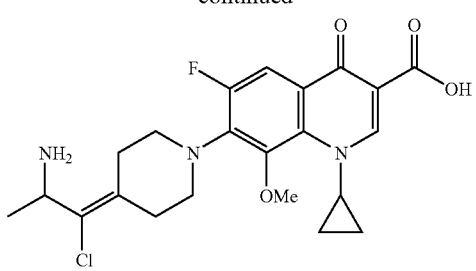
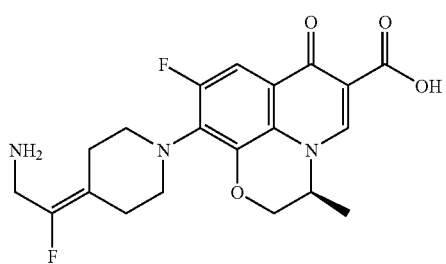
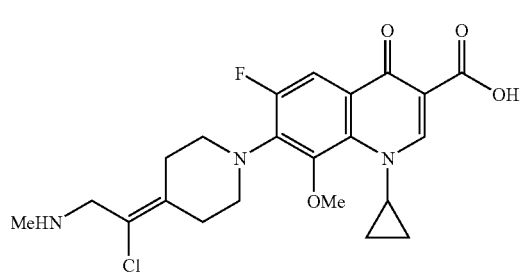
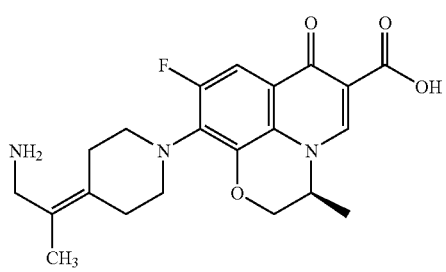
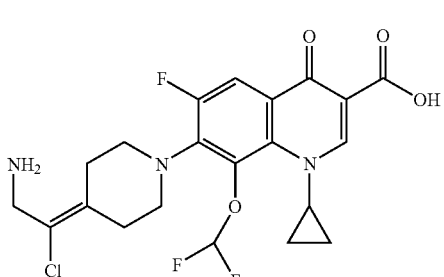
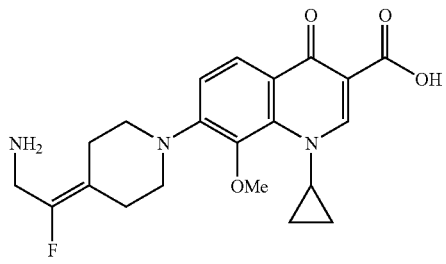
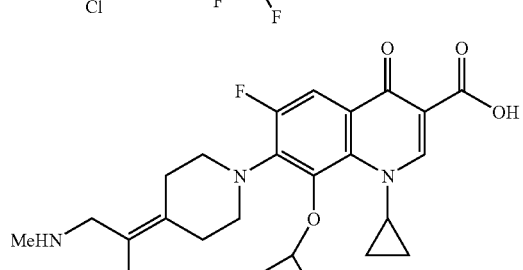
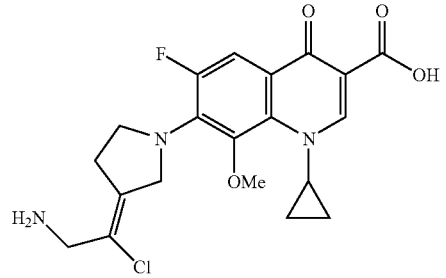
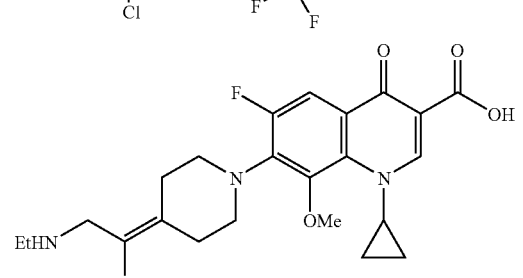
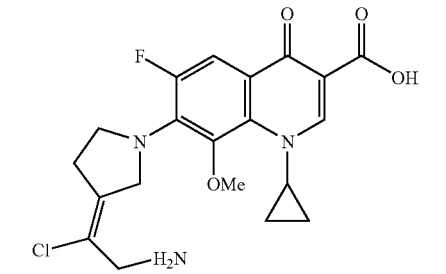
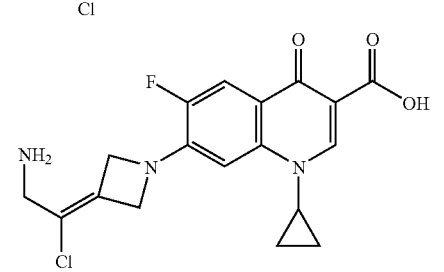

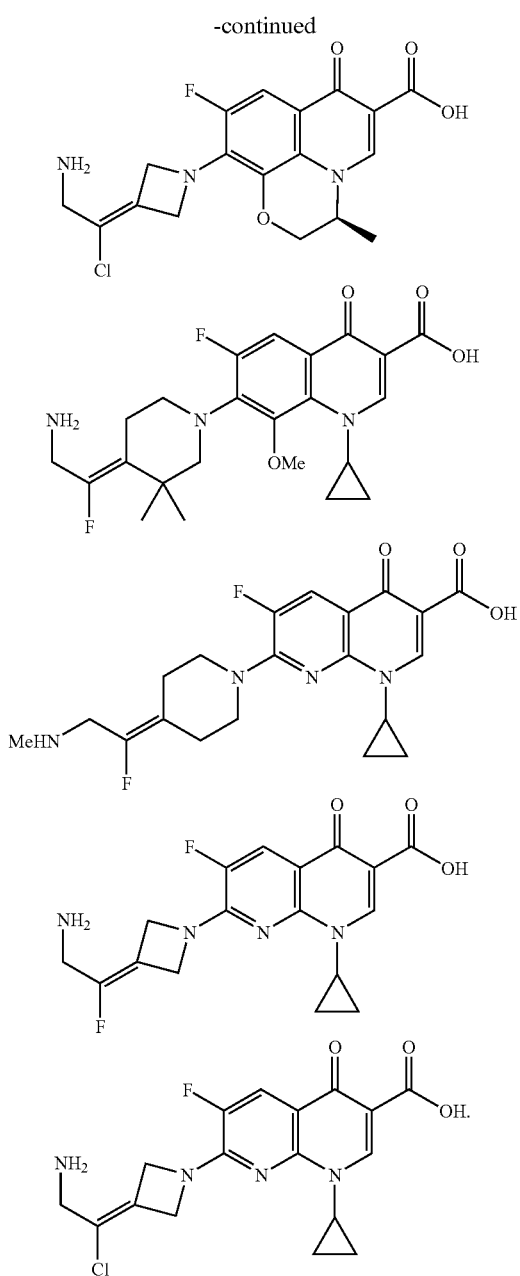
11. The compound of claim 1 having the formula:
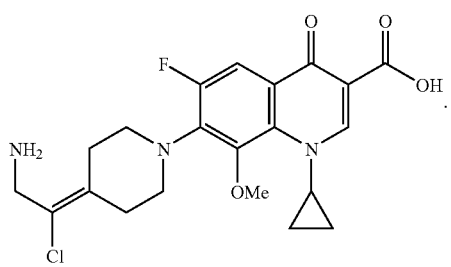
12. The compound of claim 1 having the formula:
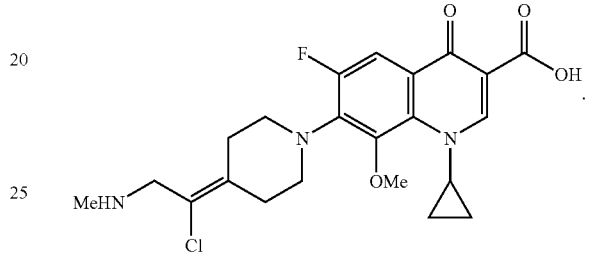
13. The compound of claim 1 having the formula:
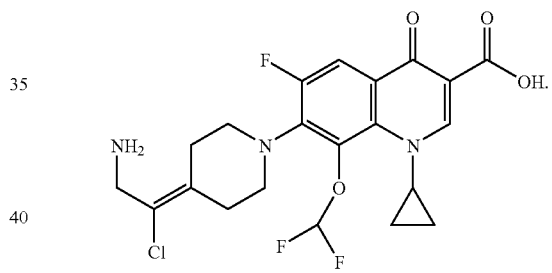
14. A method of treating a mammalian subject having a condition caused by or contributed to by bacterial infection, which comprises administering to the mammalian subject a therapeutically effective amount of the compound of claim 1.
* * * * *